US007813887B2

(12) United States Patent
Vock et al.

(10) Patent No.: US 7,813,887 B2
(45) Date of Patent: Oct. 12, 2010

(54) LOCATION DETERMINING SYSTEM

(75) Inventors: Curtis A. Vock, Niwot, CO (US);
Dennis Darcy, Tyngsboro, MA (US);
Peter Flentov, Carlisle, MA (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 11/601,406

(22) Filed: Nov. 17, 2006

(65) Prior Publication Data
US 2007/0067128 A1    Mar. 22, 2007

Related U.S. Application Data

(60) Division of application No. 11/484,199, filed on Jul. 10, 2006, now Pat. No. 7,158,912, which is a continuation of application No. 10/921,743, filed on Aug. 19, 2004, now Pat. No. 7,092,846, which is a division of application No. 10/283,642, filed on Oct. 30, 2002, now Pat. No. 6,959,259, which is a continuation of application No. 09/089,232, filed on Jun. 2, 1998, now Pat. No. 6,539,336, and a continuation-in-part of application No. 08/867,083, filed on Jun. 2, 1997, now Pat. No. 6,266,623, which is a continuation-in-part of application No. 08/764,758, filed on Dec. 12, 1996, now Pat. No. 5,960,380, and a continuation of application No. 08/344,485, filed on Nov. 21, 1994, now Pat. No. 5,636,146.

(60) Provisional application No. 60/077,251, filed on Mar. 9, 1998.

(51) Int. Cl.
*G01C 17/38* (2006.01)

(52) U.S. Cl. ........................................ 702/94

(58) Field of Classification Search ............... 702/94, 702/1, 127, 150, 155, 158, 166, 182; 202/158; 342/357, 357.06, 357.08, 357.14; 340/988, 340/995.1, 995.14, 995.27, 995.28; 701/200, 701/201, 206, 207, 208, 213
See application file for complete search history.

(56) References Cited

U.S. PATENT DOCUMENTS

| 3,978,725 | A |   | 9/1976 | Hadtke |         |
|-----------|---|---|--------|--------|---------|
| 4,089,057 | A | * | 5/1978 | Eriksson | ... 702/158 |
| 4,220,996 | A |   | 9/1980 | Searcy |         |

(Continued)

FOREIGN PATENT DOCUMENTS

GB        2137363        10/1984

(Continued)

OTHER PUBLICATIONS

Complaint, Civil Action 06-CV-02122-REB-MJW, Oct. 24, 2006.

(Continued)

*Primary Examiner*—Tung S Lau
*Assistant Examiner*—Xiuquin Sun
(74) *Attorney, Agent, or Firm*—Banner & Witcoff Ltd.

(57) ABSTRACT

A location measurement system comprises: a GPS receiver for attachment to a person and for determining earth location of the person; a display for attachment to the person; memory for storing map data; a processor configured to process earth location and the map data to instruct display the person's current location with a map on the display.

16 Claims, 49 Drawing Sheets

U.S. PATENT DOCUMENTS

| | | | |
|---|---|---|---|
| 4,223,211 A | 9/1980 | Allsen et al. | |
| 4,371,945 A | 2/1983 | Karr et al. | |
| 4,402,147 A | 9/1983 | Wu | |
| 4,510,704 A | 4/1985 | Johnson | |
| 4,578,769 A | 3/1986 | Frederick | |
| 4,694,694 A | 9/1987 | Vlakancic et al. | |
| 4,699,379 A | 10/1987 | Chateau et al. | |
| 4,703,445 A | 10/1987 | Dassler | |
| 4,722,222 A | 2/1988 | Purdy et al. | |
| 4,736,312 A | 4/1988 | Dassler et al. | |
| 4,757,714 A | 7/1988 | Purdy et al. | |
| 4,759,219 A | 7/1988 | Cobb et al. | |
| 4,763,284 A | 8/1988 | Carlin | |
| 4,763,287 A | 8/1988 | Gerhaeuser et al. | |
| 4,771,394 A | 9/1988 | Cavanagh | |
| 4,774,679 A | 9/1988 | Carlin | |
| 4,821,218 A | 4/1989 | Potsch | |
| 4,824,107 A | 4/1989 | French | |
| 4,883,271 A | 11/1989 | French | |
| 4,935,887 A | 6/1990 | Abdalah et al. | |
| 4,956,628 A | 9/1990 | Furlong | |
| 4,991,126 A | 2/1991 | Reiter | |
| 5,023,727 A | 6/1991 | Boyd et al. | |
| 5,033,013 A | 7/1991 | Kato et al. | |
| 5,148,002 A | 9/1992 | Kuo et al. | |
| 5,272,483 A * | 12/1993 | Kato | 342/357.14 |
| 5,295,085 A | 3/1994 | Hoffacker | |
| 5,343,445 A | 8/1994 | Cherdak | |
| 5,357,696 A | 10/1994 | Gray et al. | |
| 5,382,972 A | 1/1995 | Kannes | |
| 5,396,429 A | 3/1995 | Hanchett | |
| 5,420,828 A | 5/1995 | Geiger | |
| 5,446,775 A | 8/1995 | Wright et al. | |
| 5,452,269 A | 9/1995 | Cherdak | |
| 5,471,405 A | 11/1995 | Marsh | |
| 5,485,402 A | 1/1996 | Smith et al. | |
| 5,500,635 A | 3/1996 | Mott | |
| 5,509,082 A | 4/1996 | Toyama et al. | |
| 5,513,854 A | 5/1996 | Daver | |
| 5,524,637 A | 6/1996 | Erickson | |
| 5,526,290 A | 6/1996 | Kanzaki | |
| 5,590,908 A | 1/1997 | Carr | |
| 5,605,336 A | 2/1997 | Gaoiran et al. | |
| 5,636,146 A | 6/1997 | Flentov et al. | |
| 5,696,481 A | 12/1997 | Pejas et al. | |
| 5,702,323 A | 12/1997 | Poulton | |
| 5,721,539 A | 2/1998 | Goetzl | |
| 5,723,786 A | 3/1998 | Klapman | |
| 5,724,265 A | 3/1998 | Hutchings | |
| 5,734,337 A | 3/1998 | Kupersmit | |
| 5,749,615 A | 5/1998 | Itson | |
| 5,771,485 A | 6/1998 | Echigo | |
| 5,798,733 A * | 8/1998 | Ethridge | 342/357.08 |
| 5,899,963 A | 5/1999 | Hutchings | |
| 5,925,001 A | 7/1999 | Hoyt et al. | |
| 5,926,131 A * | 7/1999 | Sakumoto et al. | 342/357.06 |
| 5,929,335 A | 7/1999 | Carter | |
| 5,947,868 A | 9/1999 | Dugan | |
| 5,955,667 A | 9/1999 | Fyfe | |
| 5,978,972 A | 11/1999 | Stewart et al. | |
| 5,993,335 A | 11/1999 | Eden et al. | |
| 6,002,455 A | 12/1999 | Enomoto et al. | |
| 6,013,007 A | 1/2000 | Root et al. | |
| 6,018,705 A | 1/2000 | Gaudet et al. | |
| 6,028,625 A | 2/2000 | Cannon | |
| 6,028,627 A | 2/2000 | Helmsderfer | |
| 6,074,271 A | 6/2000 | Derrah | |
| 6,083,353 A * | 7/2000 | Alexander, Jr. | 202/158 |
| 6,111,571 A | 8/2000 | Summers | |
| 6,148,271 A | 11/2000 | Marinelli | |
| 6,163,021 A | 12/2000 | Mickelson | |
| 6,196,932 B1 | 3/2001 | Marsh et al. | |
| 6,204,813 B1 | 3/2001 | Wadell et al. | |
| 6,292,213 B1 | 9/2001 | Jones | |
| 6,305,221 B1 | 10/2001 | Hutchings | |
| 6,430,453 B1 | 8/2002 | Shea | |
| 6,450,953 B1 | 9/2002 | Place et al. | |
| 6,456,261 B1 | 9/2002 | Zhang | |
| 6,459,881 B1 | 10/2002 | Hoder et al. | |
| 6,633,743 B1 | 10/2003 | Berlinsky | |
| 6,751,164 B1 | 6/2004 | Sekiguchi | |
| 6,862,525 B1 | 3/2005 | Beason et al. | |
| 6,885,971 B2 * | 4/2005 | Vock et al. | 702/182 |
| 2002/0077784 A1 | 6/2002 | Vock et al. | |
| 2004/0102931 A1 | 5/2004 | Ellis et al. | |
| 2006/0195050 A1 | 8/2006 | Alwan et al. | |

FOREIGN PATENT DOCUMENTS

| | | |
|---|---|---|
| WO | 9854581 | 12/1998 |
| WO | 0051259 | 8/2000 |

OTHER PUBLICATIONS

Complaint, Civil Action 06-CV-02122-REB-MJW; Oct. 24, 2006.
Complaint, Civil Action 05-CV-02323; Dec. 29, 2005.
Complaint, Civil Action 06-CV-01100-WDM-PAC; Jun. 8, 2006.
Defendants Polar Electro Inc.'s and Polar Oy's Oy's Answer and Affirmative Defenses; Polar Electro Inc's Counterclaim and Demand for Jury Trial, Civil Action 06-CV-01100-WDM-PAC; Jul. 26, 2006.
Complaint, CMI Action 06-CV-01447 MSK-SNB; Jul. 26, 2006.
First Amended Complaint, Civil Action 06-CV-01447 MSK-BNB; Aug. 16, 2006.
Answer, Affirmative Defenses, Counterclaims and Demand for Jury Trial, Civil Action 06-CV-01447 MSK-BNB; Sep. 26, 2006.
Bedi, "A Simplified Optical Arrangement for the Laser Doppler Velocimeter," Oct. 1970, UOS Publication, vol. 4, pp. 27-28.
"Nike, Inc.'s Answer and Affirmative Defenses to Complaint"—from Civil Action No. 1:07-cv-00238-REB (a non-verified pleading filed by Nike, Inc. in the Civil Action, with reference to Patent No. 7,171,331); Mar. 19, 2007.
"Apple Inc.'s Answer to Complaint Counterclaims and Jury Demand"—from Civil Action No. 1:07-cv-00238-REB (a non-verified pleading filed by Apple, Inc. in the Civil Action, with reference to Patent No. 7,171,331); Mar. 19, 2007.
"Nike, Inc.'s First Supplemental Statement Pursuant to Section 8.7.5.4 of the Settlement Agreement"— from JAMS Arbitration No. 1220035678 (filed by Nike, Inc. in the Arbitration proceeding, with reference to related Patent Nos. 6,499,000; 6,885,971; 7,072,789; and 7,092,846); Mar. 29, 2007.
Nobbe, Thomas A., "Olympic Athletes Get a Boost From Technology," Machine Design, Aug. 25, 1988.
Wrigley, et al.; Gyroscopic Theory, Design, and Instrumentation, MIT Press (1969).
Herceg, et al.; Handbook of Measurement and Control, Schaevitz Engineering, Pensauker, NJ, Library of Congress 76-24971 (1976).
Broxmeyer; Inertial Navigation Systems, McGraw-Hill (1964).

* cited by examiner

TYPICAL CROSS-CORRELATION FUNCTION

TYPICAL AUTO-CORRELATION FUNCTION

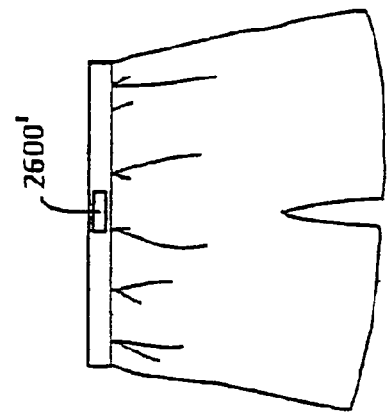
FIG. 78
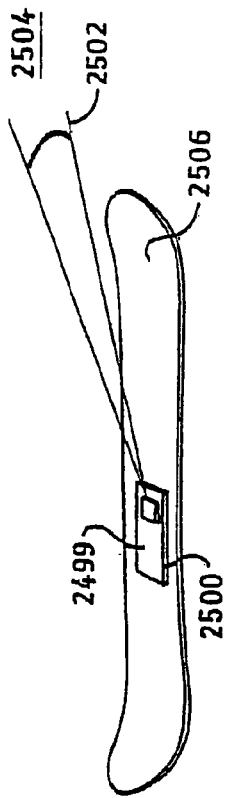
FIG. 79
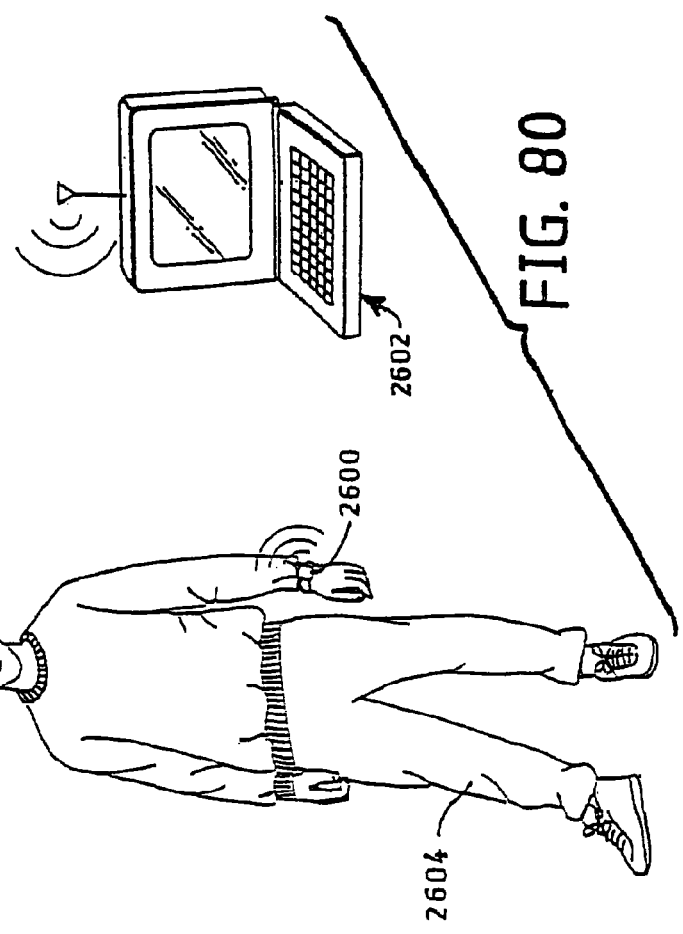
FIG. 81
FIG. 80
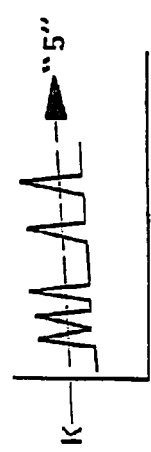

FIG. 84A
FIG. 84B
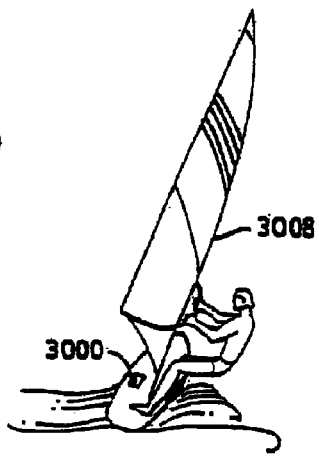
FIG. 84C
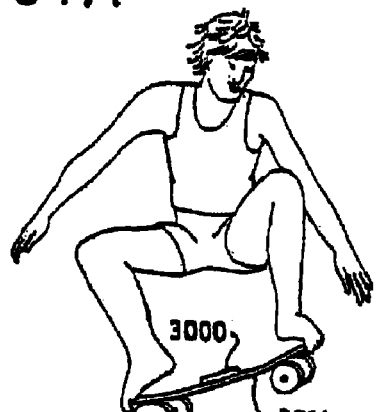
FIG. 84D
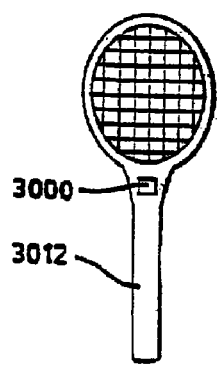
FIG. 84E
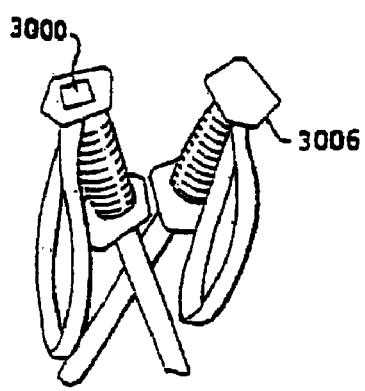
FIG. 84F
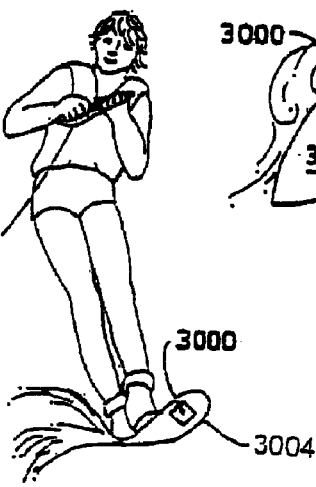
FIG. 84G
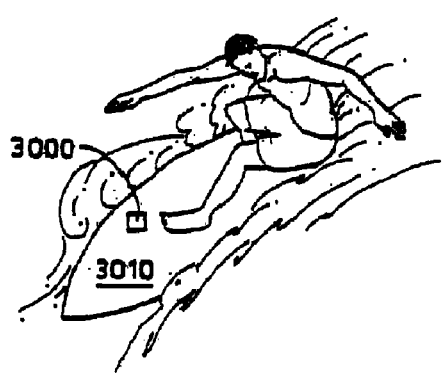
FIG. 84H

LOCATION DETERMINING SYSTEM

RELATED APPLICATIONS

This application is a divisional of U.S. patent application Ser. No. 11/484,199 (now U.S. Pat. No. 7,158,912), filed Jul. 10, 2006, which is a continuation of U.S. patent application Ser. No. 10/921,743 (now U.S. Pat. No. 7,092,846), filed Aug. 19, 2004, which is a divisional of U.S. patent application Ser. No. 10/283,642 (now U.S. Pat. No. 6,959,259), filed Oct. 30, 2002, which is a continuation of U.S. patent application Ser. No. 09/089,232 (now U.S. Pat. No. 6,539,336), filed Jun. 2, 1998, which is a continuation-in-art of U.S. application Ser. No. 08/764,758 (now U.S. Pat. No. 5,960,380), field Dec. 12, 1996, and U.S. application Ser. No. 08/867,083 (now U.S. Pat. No. 6,266,623), filed on Jun. 2, 1997, and which claims priority to U.S. Provisional Application No. 60/077,251, filed Mar. 9, 1998; U.S. Pat. No. 5,960,380 is also a continuation of U.S. application Ser. No. 08/344,485 (now U.S. Pat. No. 5,636,146), filed Nov. 21, 1994; each of the foregoing applications being expressly incorporated herein by reference.

FIELD OF THE INVENTION

The invention relates generally to monitoring and quantifying sport movement (associated either with the person or with the vehicle used or ridden by the person), including the specific parameters of "air" time, power, speed, and drop distance. The invention also has "gaming" aspects for connecting users across the Internet. The invention is particularly useful in sporting activities such as skiing, snowboarding, mountain biking, wind-surfing, skate-boarding, roller-blading, kayaking, racing, and running, in which sporting persons expend energy, catch "air", move at varying speeds, and perform jumps.

BACKGROUND OF THE INVENTION

It is well known that many skiers enjoy high speeds and jumping motions while traveling down the slope. High speeds refer to the greater and greater velocities which skiers attempt in navigating the slope successfully (and sometimes unsuccessfully). The jumping motions, on the other hand, include movements which loft the skier into the air. Generally, the greater the skier's speed, the higher the skier's loft into the air.

The interest in high speed skiing is apparent simply by observing the velocity of skiers descending the mountain. The interest in the loft motion is less apparent; although it is known that certain enthusiastic snowboarders regularly exclaim "let's catch some air" and other assorted remarks when referring to the amount and altitude of the lofting motion.

The sensations of speed and jumping are also readily achieved in other sporting activities, such as in mountain biking, skating, roller-blading, wind-surfing, and skate-boarding. Many mountain bikers and roller-bladers, like the aforementioned skiers, also crave greater speeds and "air" time.

However, persons in such sporting activities only have a qualitative sense as to speed and loft or "air" time. For example, a typical snowboarder might regularly exclaim after a jump that she "caught" some "big sky," "big air" or "phat air" without ever quantitatively knowing how much time really elapsed in the air.

Speed or velocity also remain unquantified. Generally, a person such as a skier can only assess whether they went "fast", "slow" or "average", based on their perception of motion and speed (which can be grossly different from actual speed such as measured with a speedometer or radar gun).

There are also other factors that sport persons sometimes assess qualitatively. For example, suppose a snowboarder skis a double-diamond ski slope while a friend skis a green, easy slope. When they both reach the bottom, the "double-diamond" snowboarder will have expended more energy than the other, generally, and will have worked up a sweat; while the "green" snowboarder will have had a relatively inactive ride down the slope. Currently, they cannot quantitatively compare how rough their journeys were relative to one another.

OBJECTS OF THE INVENTION

It is, accordingly, an object of the invention to provide systems and methods for determining "air" time associated with sport movements.

It is another object of the invention to provide systems and methods for determining the speed of participants and/or vehicles associated with sport movements.

It is yet another object of the invention to provide improvements to sporting vehicles which are ridden by sporting participants, and which provide a determination of speed, airtime, drop distance and/or power of the vehicle.

Still another object of the invention is to provide systems and methods for determining the amount of "power" or energy absorbed by a person during sporting activities. One specific object is to provide a gauge of energy spent by a sporting participant as compared to others in the same sport, to provide a quantitative comparison between two or more participants.

Yet another object of the invention is to provide the "drop distance" associated with a jump; and particularly the drop distance which occurs within "airtime".

Still another object of the invention is to provide a gaming system to quantitatively compare airtime, drop distance, power, and/or speed between several participants, regardless of their location.

These and other objects of the invention will become apparent in the description which follows.

SUMMARY OF THE INVENTION

As discussed herein, "air" or "loft" time (or "airtime") refer to the time spent off the ground during a sporting movement. For example, airtime according to the invention can include a snowboarder catching air off of a mogul or a ledge. Typically, airtime is greater than one-half (or one-third) second and less than six seconds. In "extreme" sporting events, the maximum airtime can increase up to about ten or fifteen seconds.

In most cases, it is useful to specify the lower and upper limits of airtime—e.g., from one second to five seconds—so as to reduce processing requirements and to logic out false airtime data. More particularly, the following description provides several techniques and methods for determining airtime. One technique, for example, monitors the vibration of the user's vehicle (e.g., a ski or snowboard) moving on the ground; and senses when the vibration is greatly reduced, indicating that the vehicle is off the ground. However, when such a user stands in line for the chair-lift, she might remain motionless for thirty seconds or more. By restricting the upper limit to five seconds, a system of the invention can be made to ignore conditions such as standing in line. Similarly, when a user walks slowly, there are cyclical periods of relatively small vibration (e.g., when the user lifts his foot off the ground). Therefore, a lower limit of one-half second or one second are appropriate; so that any detected "airtime" that falls below that lower limit is ignored and not stored.

In another aspect of the invention, the measurement of airtime is used to quantify the efficiency by which a person or sport vehicle remain on the ground. By way of example, speed skiers desire to remain on the ground; and the invention thus provides a system which monitors the person and/or vehicle (e.g., the slalom ski) to detect airtime. This information is fed back to the person (in real time or in connection with a later review of video) so that he or she can improve their posture to reduce unwanted airtime. In such applications, airtime is typically less than about three or four seconds; and the lower limit is essentially zero (that is, providing miniscule airtime data can be appropriate for training purposes).

As used herein, "power" refers to the amount of energy expended by a person or vehicle during a sporting activity, typically over a period such as one ski run. The following description provides several systems, techniques and methods for determining power. Power need not correspond to actual energy units; but does provide a measure of energy expended by the person or vehicle as compared to other persons and vehicles in the same sporting activity. Power can be used to quantify "bragging rights" between sport enthusiasts: e.g., one user can quantify that he expended more energy, or received more "punishment", as compared to a friend. Power can refer to the amount of "G's" absorbed during a given period of activity. Power is typically quantified over a period that is selectable by the user. For example, power can be determined over successive one-second periods, or successive five second periods, or successive one minute periods, or successive five minute periods, or other periods. Power can also be measured over a manually selected period. For example, two snowboarders can initialize the period at the beginning of a run down a ski slope and can stop their period at the end of the run.

"Speed" refers the magnitude of velocity as measured during a sport activity. Speed generally refers to the forward direction of the moving sportsman.

"Drop distance" refers to the height above the ground as experienced by a user or vehicle during a sport activity. Drop distance preferably corresponds to a measured airtime period. For example, a snowboarder who takes a jump off of a ledge might drop thirty feet (drop distance) in three seconds (airtime). Drop distance can also specifically refer to maximum height above the ground for a given jump (for example, a user on a flat surface can first launch upwards off a jump and return to the same level but experience a five foot drop distance).

The invention thus provides systems and methods for quantifying airtime, power, speed and/or drop distance to quantify a user's sport movement within one or more of the following activities: skiing, snowboarding, wind-surfing, skate-boarding, roller-blading, kayaking, white water racing, water skiing, wake-boarding, surfing, racing, running, and mountain biking. The invention can also be used to quantify the performance of vehicles upon which users ride, e.g., a snowboard or ski or mountain bike.

The following U.S. patents provide useful background for the invention and are herein incorporated by reference: U.S. Pat. No. 5,343,445; U.S. Pat. No. 4,371,945; U.S. Pat. No. 4,757,714; U.S. Pat. No. 4,089,057; U.S. Pat. No. 4,722,222; U.S. Pat. No. 5,452,269; U.S. Pat. No. 3,978,725; and U.S. Pat. No. 5,295,085.

In one aspect, the invention provides a sensing unit which includes a controller subsystem connected with one or more of the following sensors (each of which is described herein): an airtime sensor, a speed sensor, a power sensor, and a drop distance sensor. The controller subsystem includes a microprocessor or microcontroller and can include preamplifiers and A/D converters to interface with the sensor(s) (alternatively, the sensor contains such circuitry). The controller subsystem can further include logic circuitry and/or software modules to logic out unwanted data from the sensors (e.g., airtime data that does not correspond to reasonable loft times). Preferably, the controller subsystem also includes digital memory to store parameters for the sensors and to store data such as power, airtime, speed and drop distance (collectively "performance data") for later retrieval. A battery typically is used to power the controller subsystem. The battery can also be used for the sensors, if required. However, one preferred sensor which can function for any of the sensors is the piezoelectric foils such as made from AMP SENSORS™. These foils do not require power and rather generate a voltage in response to input forces such as sound. A display can be integrated with the sensing unit to provide direct feedback to the performance data. In one aspect, a user interface is also integrated with the sensing unit to provide user control of the sensing unit, e.g., to include an ON/OFF switch and buttons to select for acquisition or display of certain performance data.

The sensing unit of one aspect is a stand-alone unit, and thus includes a housing. The housing is rugged to survive rigorous sporting activity. Preferably, the housing provides a universal interface which permits mounting of the unit to a variety of vehicle platforms, e.g., onto a ski, snowboard, mountain bike, windsurfer, roller blades, etc. The universal interface is preferably a conformal surface which conveniently permits mounting of the sensing unit to a plurality of surfaces, e.g., a flat surface such as a snowboard, and a round bar such as on a mountain bike.

Alternatively, the sensing unit can be integrated into objects already associated with the sporting activity. In one aspect, the sensing unit is integrated into the ski boot or other boot. In another aspect, the sensing unit is integrated into the binding for a ski boot or snowboarder boot. In still another aspect, the sensing unit is integrated into a ski, snowboard, mountain bike, windsurfer, windsurfer mast, roller blade boot, skate-board, kayak, or other sport vehicle. Collectively, the sport objects such as the ski boot and the variety of sport vehicles are denoted as "sport implements". Accordingly, when the sensing unit is not "stand alone", the housing which integrates the controller subsystem with one or more sensors and battery can be made from the material of the associated sport implement, in whole or in part, such that the sensing unit becomes integral with the sport implement. The universal interface is therefore not desired in this aspect.

In one preferred aspect, the sensing unit provides for the measurement of power entirely within a watch. Manufacturers such as CASIO™, TIMEX™, SEIKO™, FILA™, and SWATCH™ make sport wrist-watches with certain digital electronics disposed therein. In accord with the invention, power measurement capability is added within such a watch so that "power" data can be provided to sport enthusiasts in all sports, e.g., volleyball, soccer, football, karate, and similar common sports.

In one preferred aspect, the performance data is transmitted via radiofrequencies (or other data transfer technique, including infrared light or inductively-coupled electronics) from the sensing unit to a data unit which is ergonomically compatible with the user. Accordingly, the sensing unit in this aspect does not require a display as performance data is made available to the user through the data unit. For example, the data unit of one aspect is a watch that the user wears on her wrist. The data unit can alternatively be made into a "pager-like" module such as known fully in the art (MOTOROLA™ is one well-known manufacturer that makes pager modules). In either case, the sensing unit and the data unit cooperate to provide a complete system for the user.

The data unit can take other forms, in other aspects. For example, the performance data can be transmitted directly to a radio receiver connected to headphones worn by the user or to a small speaker worn in the user's ear. The radio receiver is for example similar to the SONY® WALKMAN®, used by plenty of sports enthusiasts. In accord with this aspect of the invention, the sensing unit transmits performance data directly into the receiver so that the user can listen—in real time—to the results of his sports performance. Specifically, the radio receiver includes a data conversion unit which responds to the receipt of performance data from the sensing unit and which converts the performance data into sound, via the headphones, so that the user listens to the performance data. After a jump, for example, the data conversion unit transmits airtime and drop distance data to the user so that the user hears "1.8 seconds of air, 5 feet drop distance".

The data unit can also be made into the pole of a skier, such that a display at the end of the pole provides performance data to the user.

In still another aspect, the data unit is not required. Rather, performance data is transmitted such as by RF directly from the sensing unit to a base station associated with the sporting area. For example, the base station can be a computer in the lodge of a ski area. The sensing unit of this aspect transmits performance data tagged to a particular user to the base station where performance data from all users is collated, stored, compared and/or printed for various purposes. Preferably, the base station includes processing capability and storage whereby performance data can be assessed and processed. For example, a user at the end of the day can receive a print-out (or computer disk) of his performance data; and the report can include a comparison to other performers within the sporting activity. If the activity is snowboarding, for example, the user can see his performance data as compared to other snowboarders on a particular mountain. Performance data can also be catalogued according to age, date, and performance data type (e.g., airtime, power, speed and/or drop distance).

In one aspect, the base station augments the sensing units by providing processing power to calculate and quantify the performance data. For example, in this aspect, raw sensor data such as from a microphone is transmitted from the sensing unit to the base station, which thereafter calculates the appropriate performance data. The sensing unit "tags" the transmitted data so as to identify a particular user. The base station of this aspect then calculates and stores the appropriate performance data for that particular user.

The base station can further include a Web Site server that connects the base station to other such base stations via the Internet so that performance data from users can be collated, stored, compared and/or printed for a variety of purposes. One or more servers thus function as the primary servers from which users can obtain their performance data from their own computers, via the Internet (or via a LAN or WAN). In one aspect, the primary servers also function as a gaming network where performance data from all users is integrated in a recreational manner, and made available to all or selected users.

In one aspect, sensing units (or sensing units and data units) are rented by the owners of a particular sporting area (e.g., a ski area) such as in connection with the rental of a snowboard, or even as a stand-alone device that mounts to the user's board. The sensing unit can provide real-time performance data to the user, via a connected display or via a data unit. Alternatively, the sensing unit transmits data to the rental facility (or to the base station connected via a LAN to the rental facility) so that the user retrieves his or her performance data at the end of the day.

In one aspect of the invention, performance data is sensed through one or more sensors connected with the sensing unit. It is not desirable to provide all performance data for all sporting activities. For example, for white water rafting or kayaking, a "power sensing unit" is useful—to quantify the roughness of the ride—but airtime data is practically useless since typically such vehicles do not catch air. In addition, for any given system (i.e., sensing units or sensing units and data units combined), more sensors add cost and require added processing capability, requiring more power draw and reducing battery lifetime. Therefore, certain aspects of the invention provide sensing units that provide only that portion of the performance data that is useful and/or desirable for a given sporting function, such as the following sensing units:

Airtime Sensing Unit

One sensing unit of the invention measures "air" time, i.e. the time a person such as a snowboarder or skier is off the ground during a jump. This airtime sensing unit is preferably battery-powered and includes a microprocessor (or microcontroller). The airtime sensing unit either connects to a data unit; or can include a low-powered liquid crystal display (LCD) to communicate the "air" time to the user. The components for this airtime sensing unit can include one or more microphones or accelerometers to detect vibration (i.e., caused by friction and scraping along the ground) of the user's vehicle along the ground, so that "airtime" is measured when an appropriate absence of vibration is detected. Preferably, the electronics for the airtime sensing unit are conveniently packaged within a single integrated circuit such as an ASIC. A digital memory stores airtime data; or alternatively, the airtime sensing unit transmits airtime performance data to a data unit or to a base station.

The airtime sensing unit preferably provides several facets of airtime performance data, such as any of the following information data and features:

(1) Total and peak air time for the day. In this aspect, the airtime sensing unit provides at least the peak airtime for the day. The sensing unit can also integrate all airtimes for the day to provide a total airtime.

(2) Total dead time for the day. In this aspect, the airtime sensing unit includes an internal clock that also integrates the time for which no sporting activity is made such as over a given day. For example, dead time can include that time within which the user is at the bar, rather than skiing.

(3) Air time for any particular jump. As discussed above, briefly, this aspect of the airtime sensing unit provides substantially real-time data to the user such as the amount of airtime for a recent jump. By way of example, a data unit with headphones, in one aspect, provide this data to the user immediately after the jump. Alternatively, the airtime data for the jump is stored within memory (either within the data unit or in the sensing unit) so that the user can retrieve the data at his convenience. For example, data for a particular jump can be retrieved from a watch data unit on the chairlift after a particular run which included at least one jump. In this manner, the user can have substantially real-time feedback for the airtime event.

(4) Successive jump records of air time. In this aspect, jump records over a selected period (e.g., one day) are stored in memory either in the data unit or in the airtime sensing unit. These airtime "records" are retrieved from the memory at the user's convenience. The system can also store such records until the memory is full, at which time the oldest record is over-written to provide room for newer airtime data. The data can also be transmitted to a base station which includes its own memory storage for retrieval by the user.

(5) Averages and totals, selectable by the user. In this aspect, the sensing unit or data unit (or the base station) saves airtime data within memory for later retrieval by the user. The period for which the data is valid is preferably selectable by the user. The data of this aspect includes airtime averages, over that period, or airtime totals, corresponding to the summation of those airtimes over that period.

(6) Rankings of records. In this aspect, the sensing unit or data unit (or base station) saves airtime data within memory for later retrieval by the user. For example, the user obtains airtime data through the data unit while on the chairlift or later obtains the data in print-out form at the base station, or a combination of the two. The period for which the data is valid is preferably selectable by the user. The data of this aspect includes airtime records, over that period, and the airtime records are preferably ranked by airtime size, the biggest "air" to the smallest.

(7) Logic to reject activities which represents false "air" time. As discussed above, the preferred airtime sensing unit includes logic circuitry to reject false data, such as standing in line. Typically, the logic sets outer time limits on acceptable data, such as one half second to five seconds for snowboarding, one quarter second to three seconds for roller-blading, and user selected limits, targeted to a particular user's interest or activity. The logic circuitry of the airtime sensing unit preferably also works with a speed sensor, as discussed herein; and the logic operates to measure airtime only when the sensing unit is moving above a minimum speed. For example, when the sensing unit includes an airtime sensor and a speed sensor, the logic ensures that airtime data is measured only if there is motion. Such logic then ensures that false data corresponding to standing in line is not recorded as performance data. The speed limits tied to the logic are preferably selectable by the user; though certain default speeds are set for certain activities. For example, for skiing and snowboarding, 5 mph is a reasonable lower speed limit, such that all airtime, drop distance and/or power measurements are ignored at lower speeds. For roller-blading, the lower limit of speed is reasonably 1 mph, as for wind-surfing.

(8) Toggle to other device functionality. Although this section describes an airtime sensing unit, many sensing units of the invention incorporate at least two sensors, such as: airtime sensor and speed sensor; airtime sensor and power sensor; airtime sensor and drop distance sensor; a combination of airtime, power, and drop distance sensors; a combination of airtime, drop distance and speed sensors; a combination of airtime, power and speed sensors; and a full sensing unit of airtime, speed, power and drop distance sensors. Accordingly, a toggle button is usually included with the sensing unit (or alternatively with the data unit) such that the user can toggle to data corresponding to the desired performance data. Similar toggle buttons can be included with the sensing unit or data unit (which transmits data to the sensing unit) to activate only certain portions of the sensing unit, e.g., to turn off speed sensing. Alternatively, data from any given sensor can be acquired according to user-specified requirements.

Those skilled in the art should appreciate that a sensing unit with multiple sensors can simply acquire all the data, and that the data is sorted according to user needs and requests by toggle functionality at the data unit or at the base station (i.e., such as entering a request for the desired information at the computer keyboard).

(9) User interface to control parameters. As discussed above, the sensing unit and/or data unit preferably include buttons or toggle switches for the user to interact with the unit. For example, one of the units should include an ON/OFF switch, and at least one button to command the display of performance data.

In other aspects, the airtime data of above paragraphs (1)-(6) can be shown on a display connected with the sensing unit, or they can be transmitted to an associated data unit, or to a base station.

Speed Sensing Unit

One sensing unit of the invention measures "speed." This speed sensing unit is preferably battery-powered and includes a microprocessor (or microcontroller). The speed sensing unit either connects to a data unit; or can include a low-powered liquid crystal display (LCD) to communicate the "speed" to the user. Certain sporting activities also benefit by the measurement of speed, including skiing, snowboarding, mountain biking, wind-surfing, roller-blading, and others. To detect user motion, the sensing unit includes a speed sensor such as a Doppler module, as described in U.S. Pat. Nos. 5,636,146, 4,722,222, and 4,757,714, incorporated herein by reference. Alternatively, the speed sensor can include a microphone subsystem that detects and bins (as a function of frequency) certain sound spectra; and this data is correlated to known speed frequency data. A speed sensor can also include a microphone which, when coupled with the controller subsystem, detects a "pitch" of the vehicle; and that pitch is used to determine speed to a defined accuracy (typically at least 5 mph). The speed sensor can alternatively include a Faraday effect sensor (which interacts a magnetic field with an electric field to create a voltage proportional to speed). Specifically, the Faraday effect sensor sets up a current that runs orthogonal to the speed direction. In one aspect, the current is created between two electrodes formed by the two metal edges of a ski or snowboard (in circuit with the snow). When the Faraday effect sensor moves, a voltage is created proportional to velocity. The magnetic field is formed by a magnet that creates a flux substantially perpendicular to the current flow (those skilled in the art should appreciate that the orthogonality of the respective quantities can be compensated by a sine function if the quantities are not orthogonal, to retrieve the speed data).

In another aspect, a sensing unit with a microphone, for example, can benefit by using an electrical filter with a variable bandpass that tracks the dominant spectral content, denoted herein as a "tracking filter."

This speed sensing unit can be stand-alone, or a speed sensor can be integrated into a sensing unit with multiple sensors, such as described above. For example, one speed sensing unit provides both "air" time and speed to the user of the device.

Preferably, the electronics for the speed sensing unit are conveniently packaged within a single integrated circuit such as an ASIC. A digital memory stores speed data; or alternatively, the speed sensing unit transmits speed performance data to a data unit or to the base station.

The speed sensing unit preferably provides several facets of speed performance data, such as any of the following information data and features:

(1) Average and peak speed for the day. In this aspect, the speed sensing unit provides at least the peak speed for the day. The sensing unit can also integrate all speeds for the day to provide an average speed.

(2) Speed for any particular period or run. This aspect of the speed sensing unit provides substantially real-time data to the user such as the speed reached in a recent run. By way of example, a data unit with headphones can provide this data immediately (e.g., continually informing the user of data such as "25 mph" or "15 mph"). Alternatively, the speed data for the run or period is stored within memory (either within the data unit or in the sensing unit) so that the user can retrieve the data at his convenience. For example, data for a particular run or period can be retrieved from a watch data unit on the chairlift after a particular run. In this manner, the user can have substantially real-time feedback for recent periods.

(3) Successive records of speed. In this aspect, peak or average speed records over a selected period (e.g., one day) are stored in memory either in the data unit or in the speed sensing unit. These speed "records" are retrieved from the memory at the user's convenience. The system can also store such records until the memory is full, at which time the oldest record is over-written to provide room for newer speed data. The data can also be transmitted to a base station which includes its own memory storage for retrieval by the user.

(4) Averages and totals, selectable by the user. In this aspect, the sensing unit or data unit (or the base station) saves speed data within memory for later retrieval by the user. The period for which the data is valid is preferably selectable by the user. The data of this aspect preferably includes speed averages over that period.

(5) Rankings of records. In this aspect, the sensing unit or data unit (or base station) saves speed data within memory for later retrieval by the user. For example, the user obtains speed data through the data unit while on the chairlift or later obtains the data in print-out form at the base station, or a combination of the two. The period for which the data is valid is preferably selectable by the user. One record can include peak and/or average speed, over that period. The records are preferably ranked by velocity, the fastest to the slowest speeds.

(6) Logic to reject data representing contaminated speed data. The preferred speed sensing unit includes logic circuitry to reject false data, such as data corresponding to two hundred miles per hour. Typically, therefore, the logic sets outer speed limits on acceptable data, such as seventy miles per hour for a skier, as an upper limit, to one or five miles per hour as a lower limit (data that is slower than this rate is not, generally, of interest to skiers). Other reasonable limits are 70 mph to 5 mph for snowboarding, and 40 mph to 5 mph for rollerblading. User selected limits can also be used within the speed sensing unit and targeted to a particular user's interest or activity.

(7) Toggle to other device functionality. Although this section describes a speed sensing unit, many sensing units of the invention incorporate at least two sensors, such as: speed sensor and power sensor; speed sensor and drop distance sensor; and a combination of speed, power, and drop distance sensors. Accordingly, a toggle button is usually included with the speed sensing unit (or alternatively with the data unit) such that the user can toggle to data corresponding to the desired performance data. Similar toggle buttons can be included with the sensing unit or data unit (which transmits data to the sensing unit) to activate only certain portions of the sensing unit, e.g., to turn off airtime or drop distance sensing. Alternatively, data from any given sensor can be acquired according to user-specified requirements.

(8) User interface to control parameters. As discussed above, the speed sensing unit and/or data unit preferably include buttons or toggle switches for the user to interact with the unit. For example, one of the units should include an ON/OFF switch, and at least one button to command the display of performance data.

In one aspect, a sensing unit with multiple sensors simply acquires all the data, and that data is sorted according to user needs and requests by toggle functionality at the data unit or at the base station (i.e., such as entering a request for the desired information at the computer keyboard).

Power Sensing Unit

One sensing unit of the invention measures "power", a measure of the amount of energy absorbed or experienced by a user during a period such as a day. The power sensing unit thus provides a measure of the intensity or how "hard" the user played during a particular activity. The components for this power distance sensing unit can include one or more microphones or accelerometers to sense vibration or "jerk" of the user or the user's vehicle relative to the ground. For example, one power sensing unit provides a kayaker with the ability to assess and quantify the power or forces experienced during a white-water ride. The power sensing unit is preferably battery-powered and includes a microprocessor (or microcontroller). In one aspect, "power" is measured through an accelerometer. In another aspect, the power sensor includes a microphone, as discussed below. As before, the power sensing unit is stand-alone, or it can be incorporated with other units discussed herein. Preferably, the electronics for the power sensing unit are conveniently packaged within a single integrated circuit such as an ASIC. A digital memory stores power data; or alternatively, the power sensing unit transmits power performance data to a data unit. One power sensor according to the invention is an accelerometer, oriented in the direction most indicative of expended energy (e.g., for skiing, the accelerometer is preferably oriented perpendicular to the ski surface). Another power sensor is a microphone, preferably mounted within an enclosure which generates sound in response to user activity.

The power sensing unit preferably provides several facets of power performance data, such as any of the following information data and features:

(1) Peak and average power for the day. In one aspect, a power sensor is an accelerometer which generates analog data that is digitally sampled by the controller subsystem at a rate such as 1000 Hz, 100 Hz or 10 Hz. This digitally sampled data is integrated over a "power period" such as one-half second, one second, five seconds, ten seconds, fifteen seconds, twenty seconds, thirty seconds, one minute, or five minutes (depending on the sporting activity)—to specify a power "value". In another aspect, a peak power is determined for power values over a given user-selected period, e.g., one minute, one day, or other user-selected period, and stored within memory (in the sensing unit, in the data unit, and/or in the base station) for subsequent retrieval by the user. The power sensing unit can also provide an average power value over that period. By way of example, for snowboarding, a user might experience very high power activity over a period of fifteen seconds, such as within a mogul run. By determining power values over one second intervals (i.e., the "power period"), the mogul run power activity will clearly stand out as a power event in subsequent data analysis. The power period can be user selected, such as over a run down a slope on a mountain. For example, snowboarders over a run down a slope can integrate power values over that period to determine a total value, which can be compared amongst users. Alternatively, the integrated value can be divided by the total number of samples to determine an average power over that run.

(2) Successive power records. In this aspect, peak power records are stored in memory either in the data unit or in the power sensing unit. These power "records" are retrieved from the memory at the user's convenience. The system can also store such records until the memory is full, at which time the oldest record is over-written to provide room for newer power data. The data can also be transmitted to a base station which includes its own memory storage for retrieval by the user.

(3) Rankings of records. In this aspect, the power sensing unit or data unit (or base station) saves power data within memory for later retrieval by the user. For example, the user obtains power data through the data unit while on the chair-lift or later obtains the data in print-out form at the base station, or a combination of the two. The period for which the data is valid is preferably selectable by the user. The data of this aspect includes power records, over that period, and the power records are preferably ranked by the largest to the smallest.

(4) Logic to ignore data that contaminates power data. By way of example, data from sensors such as accelerometers can provide noise spikes that correspond to unreasonable power values; and the logic operates to delete such noise spikes.

(5) Toggle to other device functionality. Although this section describes a power sensing unit, many sensing units of the invention incorporate at least two sensors, such as a power sensor and drop distance sensor. Accordingly, a toggle button is usually included with the sensing unit (or alternatively with the data unit) such that the user can toggle to data corresponding to the desired performance data. Similar toggle buttons can be included with the sensing unit or data unit (which transmits data to the sensing unit) to activate only certain portions of the sensing unit, e.g., to turn off drop distance sensing. Alternatively, data from any given sensor can be acquired according to user-specified requirements.

(6) User interface to control parameters. As discussed above, the sensing unit and/or data unit preferably include buttons or toggle switches for the user to interact with the unit. For example, a sensing unit of one aspect includes an ON/OFF switch and at least one button to command the display of performance data. Since power can be scaled to correspond to real data, such as "g's" or "joules", one button can be used to change the units of the power values.

Drop Distance Sensing Unit

One sensing unit of the invention measures "drop distance". This drop distance sensing unit is preferably battery-powered and includes a microprocessor (or microcontroller). The drop distance sensing unit either connects to a data unit; or can include a low-powered liquid crystal display (LCD) to communicate the "drop distance" to the user. The components for a drop distance sensing unit of one aspect includes a pressure sensor or altimeter. Preferably, the electronics for the drop distance sensing unit are conveniently packaged within a single integrated circuit such as an ASIC. A digital memory unit stores drop distance data; or alternatively, the drop distance sensing unit transmits drop distance performance data to a data unit.

The drop distance sensing unit preferably provides several facets of drop distance performance data, such as any of the following information data and features:

(1) Total and peak drop distance for the day. In this aspect, the drop distance sensing unit provides at least the peak drop distance for the day. The sensing unit can also integrate all drop distances for the day to provide a total drop distance.

(2) Drop distance for any particular jump. This aspect of the drop distance sensing unit provides substantially real-time data to the user such as the drop distance for a recent jump. By way of example, in one aspect, a data unit with headphones provides this data immediately after the jump. Alternatively, the drop distance data for the jump is stored within memory (either within the data unit or in the sensing unit) so that the user can retrieve the data at his convenience. For example, data for a particular jump can be retrieved from a watch data unit on the chairlift after a particular run which included at least one jump. In this manner, the user can have substantially real-time feedback for the drop distance event.

(3) Successive jump records of drop distance. In this aspect, jump records over a selected period (e.g., one day) are stored in memory either in the data unit or in the drop distance sensing unit (or at the base station). These drop distance "records" are retrieved from the memory at the user's convenience. The system can also store such records until the memory is full, at which time the oldest record is over-written to provide room for newer drop distance data. The data can also be transmitted to a base station which includes its own memory storage for retrieval by the user.

(4) Averages and totals, selectable by the user. In this aspect, the sensing unit or data unit (or the base station) saves drop distance data within memory for later retrieval by the user. The period for which the data is valid is preferably selectable by the user. The data of this aspect includes drop distance averages, over that period, or drop distance time totals, corresponding to the summation of those drop distances over that period.

(5) Rankings of records. In this aspect, the sensing unit or data unit (or base station) saves drop distance data within memory for later retrieval by the user. For example, the user obtains drop distance data through the data unit while on the chair-lift or later obtains the data in print-out form at the base station, or a combination of the two. The period for which the data is valid is preferably selectable by the user. The data of this aspect includes drop distance records, over that period, and the drop distance records are preferably ranked by size, the largest distance to the smallest.

(6) Logic to reject activities which represents false drop distance. The preferred drop distance sensing unit includes logic circuitry to reject false data. Typically, the logic sets outer drop distance limits on acceptable data, such as three feet to one hundred feet for snowboarding and skiing (or up to 150 feet for extreme sports), and user selected limits, targeted to a particular user's interest. The logic circuitry of the drop distance sensing unit preferably also works with an airtime sensor, as discussed above; and the logic operates to measure drop distance only when there is a detected airtime. For example, when the sensing unit includes an airtime sensor and a drop distance sensor, the logic ensures that drop distance data is measured only if there is an airtime event, which can include its own logic as discussed above. The limits for other sports varies. In roller-blading, for example, the drop distance limits can be set to one foot minimum to ten or fifteen feet maximum.

(7) Toggle to other device functionality. Although this section describes a drop distance sensing unit, many sensing units of the invention incorporate at least two sensors, such as: drop distance sensor and speed sensor; drop distance sensor and power sensor; drop distance sensor and airtime sensor; and combinations. Accordingly, a toggle button is usually included with the sensing unit (or alternatively with the data unit) such that the user can toggle to data corresponding to the desired performance data. Similar toggle buttons can be included with the sensing unit or data unit (which transmits data to the sensing unit) to activate only certain portions of the sensing unit, e.g., to turn off speed sensing. Alternatively, data from any given sensor can be acquired according to user-specified requirements.

(8) User interface to control parameters. As discussed above, the sensing unit and/or data unit preferably include buttons or toggle switches for the user to interact with the unit. For example, the sensing unit of one aspect includes an ON/OFF switch, and at least one button to command the display of performance data such as drop distance.

In one aspect, the invention incorporates a pair of power meters that measure and quantify a competitor's performance during mogul competitions. In this application, one device is mounted to the ski (or lower body, such as the lower leg), and another to the upper body. An RF signal unit communicates readings from both devices to a signal controller at the judge's table. The combined signals determine the force differential between the lower legs and the upper body, giving an actual assessment of a competitor's performance. The device starts transmitting data at the starting gate. The device of this aspect can also be coupled to the user via a data unit with headphones to provide a hum or pitch which tells the user how effective his/her approach is.

In another aspect, the invention provides a performance system which gauges the negative airtime aspects of speed skiers. For example, it is undesirable for skiers such as Tommy Moe to lift off of the ground during training, and certainly during a speed event, which slows the skier's speed. In this aspect, the system informs the user (in real time, via a data unit) of instances of air time so that the skier can adjust and improve his competitive position. Airtime in this aspect is thus typically less than three seconds and can be as small as one tenth of a second or less. The data is preferably also communicated to a base station so that the data can be replayed together with a video of the run, so that the skier can get feedback of airtime (unwanted in speed skiing) while watching his technique.

In another aspect, the invention provides a speed and airtime sensing unit such as described above, and additionally provides a height sensor integrated with the sensing unit. In one aspect—identified herein as the "default" height measure—the height sensor detects speed and converts that speed data to height. Many jumps performed in sporting events such as snowboarding occur off of a ledge, such that "height" is determined solely by the force of gravity. In one aspect, therefore, drop distance height is determined by ½ at where a is the acceleration due to gravity (9.81 meters per second squared, at sea level) and where t is airtime, as determined by an airtime sensor as described herein. By way of example, for a one second airtime, a drop distance of 4.9 meters is measured. This result is approximately true even if the airtime occurs on a slope down a mountain. However, this calculation will be in error if there is an upward or downward motion at the start of the airtime. For example, if a jump occurs off of a mogul and the user is launching upwards into the air, then this calculation will produce an incorrect number. Accordingly, the height sensor preferably includes a level sensor which senses and measures the angle of motion relative to a plane perpendicular to the force of gravity. This angle determines the distance which should be added or subtracted from the default measure. By way of example, if at the beginning of a two second airtime the user moves at a speed of 10 mph (about 4.47 m/s), at an angle of 15 degrees upwards (such as off a mogul), then the velocity vector in the vertical direction, $V_v$, is $\sin(15°)*10$ mph; and the distance added to the default measure is approximately $\sin(15°)*2(V_v^2)/a$, or 1.05 m. The time for this upward-traveled distance is $\sin(15°)*2V_v/a$, or 0.24 s. The default time in this example is thus total airtime—0.24 s; and the default measure is 15.2 m. The total drop distance is then 15.2 m plus 1.05 m, or 16.25 m.

In one aspect, the invention provides a system for determining the loft time of a moving vehicle off of a surface. A loft sensor senses a first condition that is indicative of the vehicle leaving the surface, and further senses a second condition indicative of the vehicle returning to the surface. A controller subsystem, e.g., typically including a microprocessor or microcontroller, determines a loft time that is based upon the first and second conditions, and the loft time is preferably displayed to a user of the system by a display, e.g., a LCD or LED display. In another aspect, a power module such as a battery is included in the system to power the several components. In addition, a housing preferably connects and protects the controller subsystem and the user interface; and further includes an interface (possibly including velcro) that facilitates attaching the housing to the vehicle.

One preferred aspect of the invention includes a speed sensor, connected to the controller subsystem, which senses a third condition that is indicative of a velocity of the vehicle (or at least indicates that the vehicle is in forward motion). In this aspect, the controller subsystem includes means for converting the third condition to information representative of a speed of the vehicle. Alternatively, the speed sensor is used as logic for the airtime sensor to switch off the collection of data when there is no forward motion. According to one aspect, the system provides a user with airtime and speed of the vehicle.

In yet another aspect, a display of the invention displays selective information, including one or more of the following: the loft time; a speed of the vehicle; a peak loft time; an average loft time; a total loft time; a dead time; a real activity time; an average speed; successive records of loft information; successive records of speed information; a distance traveled by the vehicle; and a height achieved by the vehicle off of the surface.

In still another aspect, the invention includes a user interface for providing external inputs to the sensing and/or data units, including one or more of the following: a start/stop button for selectively starting and stopping the acquisition of data; a display-operate button for activating the display selectively; a speed/loft/power/drop distance toggle button for alternatively commanding a display of different performance data; means for commanding a display of successive records of performance data selectively; means for commanding a display of information corresponding to average performance data; means for commanding a display of dead time; means for commanding a display of distance traveled by the vehicle upon which the user rides; means for commanding a display of height achieved by the vehicle off of the surface; and means for commanding a display of real activity time.

Preferably, the controller subsystem of the invention includes a clock element, e.g., a 24-hour clock, for providing information convertible to an elapsed time. Accordingly, the subsystem can perform various calculations, e.g., dead time, on the data acquired for display to a user. The clock can also be incorporated into a data unit, as a matter of design choice.

In another aspect, the airtime sensor is constructed with one of the following technologies: (i) an accelerometer that senses a vibrational spectrum; (ii) a microphone that senses a noise spectrum; (iii) a switch that is responsive to a weight of a user of the vehicle; (iv) a voltage-resistance sensor that generates a voltage indicative of a speed of the vehicle; and (v) a plurality of accelerometers connected for evaluating a speed of the vehicle.

In another aspect, induced-strain sensors, such as a piezoceramics (e.g., PZT, or lead zirconate), piezopolymer (e.g., PVDF), or shape memory (e.g., NiTiNOL) elements can be used in sensors discussed herein. An "induced strain" sensor provides a measurable output such as a voltage in response to an applied strain, generally a compressive strain. Also, strain gages and load cells (which are usually made using strain gage bridges) can also be incorporated into sensors herein: the former for measuring bending strains, the latter for forces and compressive strains. In still another aspect, FSRs (force sensing resistors), such as those manufactured by IEE Interlink, can be used. The FSRs are pads consisting of inter-digitated electrodes over a semi-conductive polymer ink, wherein the resistance between the electrodes decreases nonlinearly as a function of applied compressive load, with high sensitivity and low cost.

In a preferred aspect, the airtime sensor of the invention senses a spectrum of information, e.g., a vibrational or sound spectrum, and the controller subsystem determines the first and second conditions relative to a change in the spectrum of information. Further, the controller subsystem interprets the change in the spectrum to determine the loft time.

For example, one aspect of an airtime sensor according to the invention includes one or more accelerometers that generate a vibrational spectrum of the vehicle. In such an aspect, the first and second conditions correspond to a change in the vibrational spectrum. By way of another example, one airtime sensor of the invention includes a microphone subassembly that generates voltages corresponding to a noise spectrum of the vehicle; and, in this aspect, the first and second conditions correspond to a change in the detected noise spectrum. Because these spectrums are influenced by the particular activity of a user, e.g., standing in a ski line, a controller subsystem of the invention preferably includes logic for assessing boundary conditions of the spectrum and for excluding certain conditions from the determination of airtime. Accordingly, if a skier is in a lift line, such conditions are effectively ignored. One boundary condition, therefore, according to an aspect of the invention, includes an elapsed time between the first condition and the second condition that is less than approximately 500 ms; such that events that are within this boundary condition are excluded from the determination of airtime. One other boundary condition, in another aspect, includes an elapsed time between the first condition and the second condition that is greater than approximately five seconds; such that events that are outside this boundary condition are excluded from the determination of airtime. Because these boundary conditions are important in the aspects of the invention which utilize a spectrum of information, the sensing and/or data units preferably utilize a user interface to provide selective external inputs to the controller subsystem and for adjusting the boundary conditions selectively.

In one aspect, the change in a vibration or sound spectrum is detected through waveform "enveloping" of the time domain signal, and then by passing the output of this envelop to a threshold-measuring circuit. Pre-filtering of the signal, especially to remove low-frequency content beyond high pass filtering, can also be included.

In still another aspect, the controller subsystem determines a pitch of the spectrum by isolating a best-fit sine wave to a primary frequency of at least part of the spectrum and by correlating the pitch to a vehicle speed. Accordingly, the invention of this aspect detects spectrum information and correlates that information to a speed of the vehicle. Typically, a higher pitch frequency corresponds to a higher vehicle speed and a lower pitch frequency corresponds to a lower vehicle speed. However, in another aspect, the selected pitch frequency is calibrated relative to a selected vehicle and speed.

In still another aspect, speed is inferred by the amount of energy at different vibrational frequencies, as discussed herein.

The invention also provides, in another aspect, means for storing information including look-up tables with pitch-to-speed conversions for a plurality of vehicles. This is useful because different vehicles have different associated noise and/or sound spectrums associated with the vehicle. Accordingly, the invention in this aspect includes memory for storing the respective calibration information of the different vehicles (typically in a look-up table format) so that a user can utilize the invention on different vehicles and still accurately determine speed. Specifically, a particular pitch is associated with a particular speed for a particular vehicle; and that association is selectively made by the user.

In several aspects of the invention, the controller subsystem includes one or more of the following: means for selectively starting and stopping the acquisition of data by the sensing unit; means for responding to an external request to activate a display for the display of performance data; means for responding to an external request to alternatively display airtime, drop distance, speed and/or power; and/or means for responding to an external request to display successive records of performance data.

The invention also provides certain methodologies. For example, in one aspect, the invention provides a method for determining the loft time of a moving vehicle off of a surface, comprising the steps of: (1) sensing the vehicle leaving the surface at a first time; (2) sensing the vehicle returning to the surface at a second time; and (3) determining a loft time from the first and second times. Preferably, the loft time is provided to the user who performed the jump via one of the following methods: through a display located with the user, either in a data unit or within a sensing unit; through a real time feedback heads-up display or headphones; through a report available at a base station located at the area where the jump occurred, such as after a day of skiing; and/or through a computer linked to a network like the Internet, where the airtime data is stored on a server on the network, such as a server located at the area where the jump occurred.

In still another aspect, the invention provides a method of measuring the amount of "power" a user absorbs during the day. A motion sensor, e.g., a microphone or accelerometer, attaches to the vehicle, preferably pointing perpendicular to the top of the vehicle (e.g., perpendicular to the top surface of the snowboard) so that a measure of acceleration, "force", jerk or jar associated with the user is made. The data from the motion sensor is integrated over a selected time—e.g., over the time of the skiing day, or over power periods such as one minute intervals—so that an integrated measure of motion is acquired. By way of example, if the motion sensor is an accelerometer positioned with a sensitive axis arranged perpendicular to the top snowboard surface, then, through integration over the power period, an integrated measure of "power" is obtained.

Those skilled in the art should appreciate that power can be converted to actual power or similar units—e.g., watts or joules or ergs or Newtons—though real units are not as important as having a constant, calibrated measure of "power" for each user. That is, suppose two snowboarders have power sensors on their respective snowboards. If one person skis a green slope and another skis a double-diamond, then the integrated value out of the double-diamond snowboarder will be greater. The units are therefore set to a reasonably useful value, e.g., generic power "UNITS". In one aspect, the power units are set such that a value of "100" indicates a typical snowboarder who skies eight hours per day and on maximum difficult terrain. At the same time, a snowboarder who rides nothing but green beginner slopes, all day, achieves something far less, e.g., a value of "1". In this manner, average skiers on blue, intermediate slops will achieve intermediate values, e.g., "20" to "50". Other scales and units are of course within the scope of the invention, and should be set to the particular activity.

Units for airtime are preferably set to seconds, such as "1.2 s". Units for speed are preferably set to miles per hour, kilometers per hour, meters per second, feet per second, inches per second, or centimeters per second. Units for drop distance are preferably set to feet, meters, inches, or centimeters.

In one aspect, the sensing unit (and/or the data unit) has a user interface. The interface can include a display and/or audible feedback such as through headphones. In one aspect, the audible feedback informs the user of big "air" words such as "awesome" if for example a snowboarder hit really big air (e.g., over five seconds). In another aspect, the interface electronics include a low-power piezo "buzzer" or headphone "bud" speaker that sounds whenever an "air" condition is sensed. This provides immediate feedback to the user. Further, in another aspect a varying pitch is used to give a speed indication. For instance, the ear can readily distinguish an octave pitch change, which can for example correspond to each 5 mph change in speed.

The measure of power according to the invention thus provides significant usefulness in comparing how strenuous one user's activity is as compared to another. For example, suppose two users ski only blue, intermediate slopes with the exact same skill and aggressiveness except that one user chooses to sit in the bar for three hours having a couple of cocktails. At the end of an eight hour day—providing the power period is set for the whole day—the skier who skied all eight hours will have a power measurement that is 8/5 that of his cocktail-drinking companion. They can thereafter quantitatively talk about how easy or how difficult their ski day was. As for another example, suppose a third friend skis only double-diamond slopes and he takes four hours out to drink beer. At the end of the day, his power measure may still be greater than his friends depending upon how hard he skied during his active time. He could therefore boast—with quantitative power data to back him up—that he had more exercise than either of his friends even though he was drinking half the day.

In one aspect, the invention incorporates a breathalyzer—used to measure a user's consumption (i.e., a blood alcohol level)—and the level is stored such as within the memory within the controller subsystem. A base station can upload the data to the memory, as desired.

The measure of air time, according to the invention, can also be used in a negative sense. That is, speed skiers try to maintain contact with the ground as air time decreases their speed. By monitoring their air time with the invention, they are better able to assess their maneuvers through certain terrain so as to better maintain ground contact, thereby increasing their speed.

The measurement of air, speed and power, and drop distance, in accord with the invention, are preferably made through one or more sensors located with the vehicle, e.g., on the snowboard or ski, upon which the person rides. As such, it is difficult to see the sensor; so one aspect the invention provides an RF transmitter in the sensing unit. A data unit coupled to the RF transmitter—e.g., in the form of a watch, paging unit, or radio receiver with headphones, is located at a convenient location with the person. The performance data—e.g., air, power, drop distance and speed—is transmitted to the person for convenient viewing, or listening. In still other aspects, a memory element in the data unit (or alternatively in the sensing unit) provides for storing selected parameters such as successive records of speed, air, drop distance and power, or averages for the performance data. Data can also be transmitted from the sensing unit to a base station, as discussed above. Those skilled in the art should appreciate that other data transfer techniques can be used instead of RF, including IR data transfer between the units.

In one aspect, the sensing unit internally resets (i.e., shuts off) when the unit senses no reasonable or useful performance data for a preselected period of time. By way of example, through a clock within the microprocessor, the unit automatic time-outs after that period, saving battery power.

In one aspect, a temperature sensor is included with the sensing unit (or data unit). A temperature profile is taken over the course of a activity day and is later displayed so that the user may boast that he or she skied in the most arduous situations.

Preferably, performance data is accumulated and then transmitted to a base station such as a ski lodge. For mountain biking, data can be telemetered back to a club house. Through the use of Internet connectivity, these data sets can also be downloaded off a Web site so that the user can compare different slopes or areas, together with performance. The data can also be evaluated and figures of merit can be applied to each run so that a skier can look at his or her performance and see how they did relative to other users. A skier may find for example that he skied better on that trail than any one else all month, year or ever. A handicap can also be applied to other mountains and trails so that a national or world competition is achieved. This interconnectivity is permitted by use of the World Wide Web or simply by using bulletin boards that are called up and updated, as known in the art. Telenet or FTP sites can also contact each other or be contacted by a home site that will assimilate the data and prepare it for display. Security could be ensured so that a user has confidence that only he or she can access their own data.

The invention thus provides, in one aspect, a national or regional game to be played so that the many users can compare and store performance data. Ski areas may use this data, for example, with the participant's knowledge and consent so that it will lure skiers to their lifts in the hope that they will win an award. Awards for the highest vertical drop, most air time, greatest speed or most power may also be awarded. The prizes could simply be free lift tickets.

In one aspect, power for the sensing units (or data units) may be saved during times of inactivity by powering off most of the electronics with a solid state switch such as a MOSFET. The processor or some minimum electronics can remain powered so that when activity is detected, the remaining electronics are powered as needed. Further, to save power, sensors such as accelerometers are duty cycled.

In another aspect, downward velocity is determined by knowing the rate of descent such as through a pressure sensor. Pressure sensing and airtime can thus be used to determine vertical drop, where loft is determined by the absence of a vibratory noise floor, for example.

In another aspect, the GPS is used to determine speed down a slope. With updates as frequent as one second, there is more than enough bandwidth to acquire changing GPS data. GPS however can have large errors associated with uncertainty of positioning calculations. This may be remedied by using differential GPS. Differential GPS makes use of a fixed GPS receiver with a known position, such as at the base station. When functioning as a sensor, therefore, the GPS receiver receives updates from the base station to maintain accurate position. When large errors are received, they are rejected because the fixed receiver is at a known position, resulting in a data correction that is also applied to the moving receiver on the slope. In some areas of the United States, the correction codes for differential GPS are broadcast for general use.

In still another aspect, when using a GPS receiver, individual ski maps for each trail are downloaded into memory so that the skier may see where they are on the display. Also, 3D topographical information is also preferably downloaded so that features can be attached to these maps and to aid in performance data determination. By knowing the height in 3D space of the receiver, and with the stored height of the slope in memory, the distance off the ground is determined. Loft time is also thus determined in addition to vertical drop. Loft detection with a GPS system may thus return the value of drop distance.

In another aspect, speed is determined by use of neural network synthesis. A neural network extracts speed information from a sensor such as a microphone or an accelerometer. This is accomplished, for example, by recording microphone data on a ski or snowboard along with a true speed sensor, such as a Doppler microwave sensor. Two data sets are thus generated: the first data set contains data acquired from the microphone that will be used in the final system; and the second data set corresponds to the true device that is used as a reliable speed detector. These two data sets are fed into a neural network, and the output of the neural filter is then compared with known good speed data. The various weights of the neural network are adjusted until a match is determined. At this point, the neural network is used to process the first data set to reliably determine speed. In the event that a match is not found, a more complex but powerful network is developed. The first data set is then fed into the new net and a match is developed by adjusting the weights of the nodes. This process is repeated constantly until a match is determined. Each failure results in a larger neural network but increases the probability that the next filter will achieve a match.

In areas where the ski run is visible, the speed and trajectory of a skier may be achieved by the use of a digital imaging system, in accord with another aspect. The imaging system can thus include a CCD camera that looks at the slope and watches skiers traverse down the slope. By knowing the distances along the slope, and the fact that the camera is stationary, the distance moved is determined frame to frame, corresponding to position in time that correlates to speed. Skiers can be identified by signs they wear, including a distinctive pattern which allows identification of individual skiers.

The invention is next described further in connection with preferred embodiments, and it will be apparent that various additions, subtractions, and modifications can be made by those skilled in the art without departing from the scope of the invention

BRIEF DESCRIPTION OF THE DRAWINGS

A more complete understanding of the invention may be obtained by reference to the drawings, in which:

FIG. 78 illustrates data signals representative of sensing power in accord with the invention;

FIG. 79 illustrates a Doppler sensing system constructed according to the invention;

FIG. 80 illustrates a watch-based sensing system constructed according to the invention;

FIG. 81 illustrates a clothing-integrated sensor constructed according to the invention;

FIGS. 84A-84H illustrate integration of a sensing unit of the invention integrated into various implements, in accord with the invention.

DETAILED DESCRIPTION OF ILLUSTRATED EMBODIMENTS

Figure 1A:
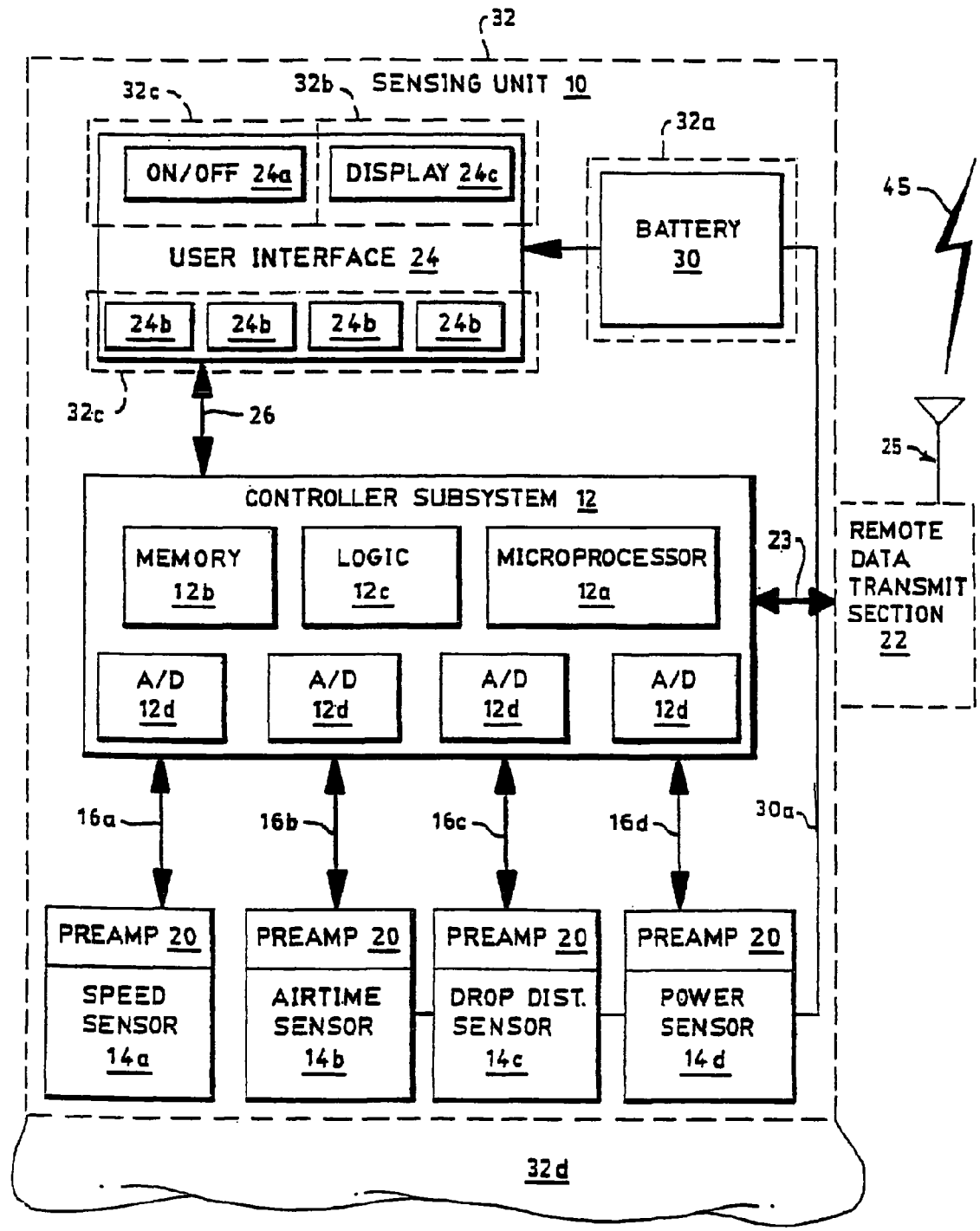
FIGS. 1A and 1B show a schematic layout of a sensing unit, data unit and base station, each constructed according to the invention, for providing performance data to participants in sporting activities.

FIG. 1A illustrates a sensing unit 10 constructed according to the invention. A controller subsystem 12 controls the unit 10 and is connected to one or more sensors 14a-14d. Typically, the subsystem 12 receives data from the sensors 14a-d through data line 16a-d; though certain sensors 14 require or permit control signals, so data lines 16a-d are preferably bi-directional. It is not necessary that the unit 10 incorporate all sensors 14a-14d and only one of the sensors 14a, 14b, 14c or 14d is required so as to provide performance data. In one preferred embodiment, however, the unit 10 includes all four sensors 14a-14d. In another preferred embodiment, only the airtime sensor 14b is included within the unit 10.

The sensors 14a-14d take a variety of forms, as discussed herein. Generally, the speed sensor 14a provides data indicative of speed to the controller subsystem 12 along data line 16a. One exemplary speed sensor 14a utilizes a microwave Doppler module such as made by C&K Electronics. The airtime sensor 14b provides data indicative of airtime to the controller subsystem 12 along data line 16b. One exemplary airtime sensor 14b utilizes a microphone such as a piezo foil by AMP Sensors, Inc. The drop distance sensor 14c provides data indicative of drop distance to the controller subsystem 12 along data line 16c. One exemplary drop distance sensor 14c utilizes a surface mount altimeter such as made by Sensym, Inc. The power sensor 14d provides data indicative of power to the controller subsystem 12 along data line 16d. One exemplary power sensor 14d utilizes an accelerometer such as made by AMP Sensors, Inc. or Analog Devices, Inc.

In certain embodiments, one sensor 14 functions to provide data that is sufficient for two or more sensors 14. By way of example, in one embodiment, the airtime sensor 14b incorporates a microphone or piezo-foil which senses noise vibration of the unit 10. This noise vibration data is used to sense motion (and/or coarse speed) and power; and thus a single sensor 14b functions to provide data for sensors 14a and 14d. Those skilled in the art should thus appreciate that the number of sensors 14 is variable depending upon the type of sensing transducer and upon the processing capability of the subsystem 12 (e.g., a DSP chip within the subsystem 12 can provide flexible processing of data from the sensors 14 to limit the number of sensors 14 required to provide performance data); and that the number of sensors 14 is made for illustrative purposes.

The controller subsystem 12 preferably includes a microprocessor or microcontroller 12a to process data from the sensors 14 and to provide overall control of the unit 10. The microprocessor 12a can include a 24 hr. clock to provide certain performance data features as described herein. The subsystem 12 also preferably includes digital memory 12b to store parameters used to process data from the sensors 14 and to store performance data for later retrieval. The subsystem 12 also preferably includes logic 12c to restrict data from the sensors 14 to reasonable data compatible with certain limits such as stored within memory 12b. For example, the memory 12b can store speed limits for the speed sensor 14a, and the logic 12c operates such that any data received from data line 16a is ignored if above or below a pre-set range (typically, one to five seconds for sport activities such as snowboarding).

Figure 1B:
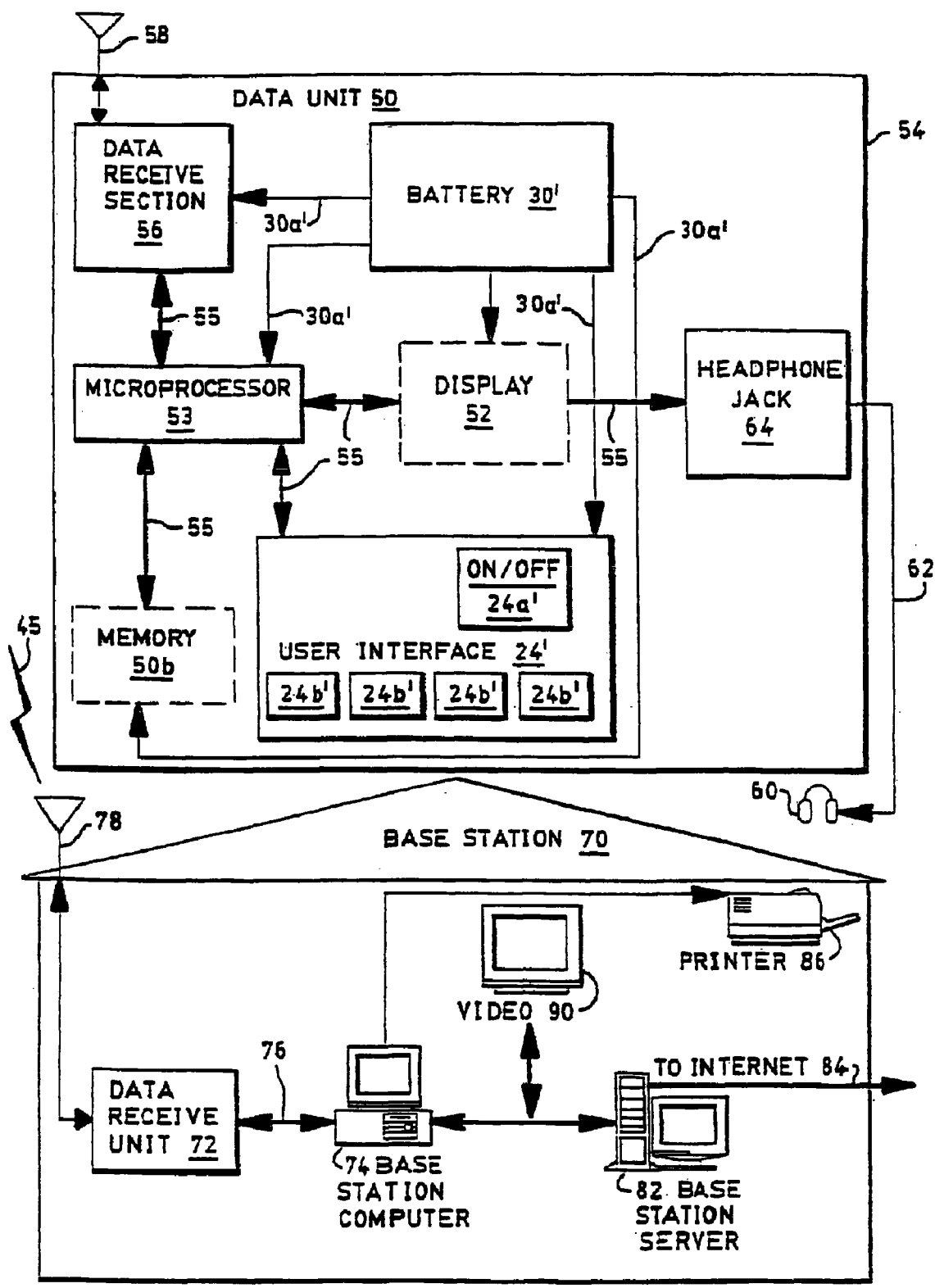

Those skilled in the art should appreciate that alternate configurations of memory 12b and logic 12c are possible. By way of example, these elements 12b and 12c can be incorporated entirely within the microprocessor 12a; and thus the configuration of the subsystem 12 is illustrative and not limiting. In addition, in certain embodiments of the invention as described herein, memory 12b and/or logic 12c are not required, since relatively raw data is acquired by the unit 10 and transmitted "off board" through an optional remote data transmit section 22 (e.g., an RF transmitter) and to a data unit 50 or to a base station 70, as shown in FIG. 1B. In such embodiments, the raw data is processed within the data unit 50 or the base station 70 so that a user of the unit 10 can obtain performance data from the data unit 50 and/or base station 70.

To acquire signals from the sensors 14, the controller subsystem 12 typically includes A/D converters 12d, such as known in the art. Each sensor 14 also typically includes a preamplifier 20 which amplifies the signal from the transducer within the sensor 14 prior to transmission along the associated data line 16. Those skilled in the art should however appreciate that the exact configuration of the preamplifier 20, microprocessor 12a and the A/D converters 12d depend upon specifics of the sensor 14 and the subsystem 12. For example, certain sensors 14 available in the marketplace—such as an accelerometer subsystem—include pre-amplification and A/D conversion; so the data line 16 and subsystem 12 associated with such a sensor should support digital transmission without redundant A/D conversion.

In one embodiment, the sensing unit 10 is "stand alone" and thus includes a user interface 24 that connects to the controller subsystem 12 via a data line 26. The interface 24 includes an ON/OFF switch 24a, to manually turn the unit 10 ON and OFF, and one or more buttons 24b (preferably including at least one toggle button to other unit functionality) to command various actions of the unit 10, e.g., the display of different performance data on the display 24c. Those skilled in the art should appreciate that the interface 24 is illustrative, rather than limiting, and that elements such as the display 24c can reside in other areas of the unit 10. The data line 26 is preferably bi-directional so that user commands at the interface 24 are recognized and implemented by the subsystem 12 and so that performance data stored in the memory 12b is displayed, upon command, at the display 24c.

A battery 30 is generally used to power the unit 10, including the user interface 24, controller subsystem 12 and sensors 14, if power is required. As such, back-plane power lines 30a are shown to connect the battery 30 to the various elements 24, 12, 14. One preferred sensor however is a piezo-foil that does not require power, and thus such a connection 30a may not be required for a sensor with a foil (note that the preamplifier 20 may still require power).

The unit 10 is generally enclosed by an appropriate housing 32, such as a plastic injected molded housing known in the art. The housing 32 is rugged to withstand the elements such as snow, water and dirt. A water-tight access port 32a permits for the removal and replacement of the battery 30 within the housing 32, as required, and as known in the art.

When the unit 10 is stand alone, the housing 32 also includes a window 32b (possibly the surface of the display 24c integrated substantially flush with the housing surface) in order to see the display 24c. When stand alone, the housing 32 also includes access 32c to the buttons 24a, 24b. The access 32c is for example provided through pliant rubber coverings; or the buttons 24a, 24b are made as keypads, as known in the art, that integrate directly with the surface of the housing 32. Other techniques are available; and in each case the buttons 24b, 24a and housing 32 cooperate so as to provide an environmentally secure enclosure for the electronics such as the microprocessor 12a while providing an operable interface to communicate with the subsystem 12.

The housing 32 preferably includes a universal interface 32d which provides flexible and conformal mounting to a variety of surfaces, such as to the relatively flat surface of a snowboard or to a round bar on a mountain bike. The universal interface 32d is designed to permit stand alone units 10 to be sold in stores regardless of how or where a user mounts the unit, to determine performance data for his or her particular activity.

In certain aspects, the sensing unit 10 is not "stand alone." In particular, it is sometimes desirable to mount the sensing unit 10 in an obscure location that is hard to see and reach, such as on a ski, or with a binding for a ski or snowboarding boot. In such locations, it is preferable that the unit 10 is a "black box" that is rugged to withstand abuse and environmental conditions such as water, snow and ice. Therefore, in such a configuration, the user interface 24 is not included within the unit 10 (since snow and dirt can cover the unit 10), but rather data from the unit 10 is communicated "off board" such as to the data unit 50. In this configuration, a data transmit section 22 receives data from the subsystem 12 via data bus 23; and transmits the data to a remote receiver, e.g., the data receive section 56 of the data unit 50 and/or to the data receive unit 72 of the base station 70.

The communication between unit 10 and the data unit 50, or base station 70, is preferably via RF signals 45, known in the art, which utilize antennas 25, 58 and 78. However, those skilled in the art should appreciate that other data communication techniques are available, including infrared transmission, inductively coupled data transmission, and similar remote (i.e., non-wired) techniques. The data transmit section 22 and antennas 25, 58 and 78 are thus shown illustratively, whereas those skilled in the art should appreciate that other techniques can replace such elements, as desired, to perform the same function.

FIG. 1B thus also shows a schematic view of a data unit 50 constructed according to the invention. As mentioned above, the data unit 50 cooperates with the unit 10 to provide performance data to a user of the unit 10. In one preferred embodiment, the unit 50 is sized and shaped much like a portable beeper, known in the art, and can include a display 52 to inform the user of performance data. In another preferred embodiment, the unit 50 is incorporated within a watch such as provided by manufacturers like TIMEX™ or CASIO™. A battery 30' provides power to the elements of the unit 50 through power lines 30a' (in the watch configuration, the existing battery replaces battery 30'). A user interface 24' operates as described above (with like numerals) to, for example, provide a display of performance data, upon command. The unit 50 includes a housing 54 that is also preferably plastic injected molded and rugged to protect the elements of the unit 50. Although not illustrated, the housing 54 incorporates access ports and windows, as known in the art, to permit access to the buttons 24b' (preferably including at least one toggle button to other unit functionality), to view the display 24a' (as similarly described in connection with the sensing unit 10), and/or to replace the battery 30'. The antenna 58 represents one technique through which data 45 is communicated between the units 10, 50; although those skilled in the art should appreciate that other communication forms are within the scope of the invention, including communication by infrared light.

The data unit 50 generally requires a controller such as a microprocessor 53 to control the unit 50 and the elements therein. Data buses 55 provide data interface by and between the microprocessor 53 and the elements. Accordingly, data entered at the user interface 24' is bidirectional through data bus 55 so that user commands are received and implemented by the microprocessor 53. A memory 50b is typically included within the data unit 50 (or within the processor 53) so as to store parameters and/or performance data, much like the memory 12b.

In a preferred embodiment, performance data is thus made available to a user via the display 52. However, in another embodiment, performance data is transmitted to a headphones assembly 60 connected, datawise, to the microprocessor 53 so that performance data is relayed in near real time, as the user performs the associated stunt. The headphones 60 connect to the unit 50 by standard wiring 62 and into a jack 64 in the unit 50. For example, through the user interface 24', the user can command the microprocessor 53 to provide airtime data to the headphones 60 immediately after an airtime is detected. Other performance data can similarly be set, such as continual speed playback, through the headphones 60.

Performance data can thus be viewed on the display 52 and/or "heard" with the headphones assembly 60. In either case, a user commands the unit 50 to provide performance data for any memory stored within memory 12b or 50b. Accordingly, data communication between the units 10 and 50 is preferably bi-directional, so that a user's command at interface 24' is understood and implemented by the processor 12a.

Those skilled in the art should appreciate that the microprocessor 53 need not be a complex or expensive microprocessor as the majority of the processing for performance data is done within the sensing unit 10. As such, the microprocessor 53 can be a microcontroller which operates with basic functionality, e.g., to display performance data corresponding to user inputs at the interface 24'. How processing is apportioned between the units 50, 10 is, however, a matter of design choice. That is, for example, most of the processing can be done within the unit 50, wherein the unit 10 can then have reduced processing capability, if desired. These choices extend to elements such as the memories 12b, 50b, as they can have redundant capability. When the unit 10 is stand alone, a user interface 24 is generally included (unless data is transmitted directly to the base station 70 for later retrieval). When the system of the invention includes both units 10, 50, then the user interface 24 is generally not included since the interface 24' sufficiently controls the system. In this latter case, the functionality and configuration of the microprocessors 12a, 53, memory 12b, 50b and logic 12c are a matter of design choice; and some elements might be eliminated to save cost. For example, the memory 50b can be designed to support all memory requirements of a system incorporating both units 10, 50 to eliminate redundancy; and thus memory 12b would not be required.

Other configurations of a system combining units 10 and 50 exist. For example, one configuration eliminates the display 52 so that performance data is only available via the headphones assembly 60. In another configuration, the sensing unit 10 works only with the base station 70 and without a data unit 50. Further, such a configuration need not include a user interface 24 or a display 24c, since all data collected by the unit 10 can be stored and processed at the base station 70.

The base station 70 thus includes an antenna 78 and a data receive unit 72 (or alternatively other wireless communication technology, as known in the art) to collect data signals 45. Typically, the base station 70 corresponds to a well known facility located at the sporting area, such as a ski lodge. A base station computer 74 connects to the base station data receiver unit 72, via the bus 76, to collect and process data. As such, one sensing unit 10 of the invention simply includes one or more sensors 14 and enough control logic and processing capability to transmit data signals 45 to the base station 70, so that substantially all processing is done at the base station 70. This configuration is particularly useful for aspects of the invention such as speed skiing, where the sensing unit 10 is mounted with the speed skier's ski, but where that user has no requirement to view the data until later, after the run (or where instructors or judges primarily use the data). However, as discussed above, that speed skier can also use a data unit 50 with headphones 60 to acquire a real-time feedback of unwanted airtime, such as through an audible sound, so as to correct his or her form while skiing. In one aspect, the base station 70 preferably has the capability to collect, analyze and store performance data on a server 82 for later review.

Accordingly, the base station 70 includes a computer 74 to collect, analyze and process data signals to provide performance data to users and individuals at the base station 70. The performance data is generally stored on a server 82, which can have an Internet connection 84 so that performance data can be collected from remote locations. If there are multiple users, which typically is the case, then the sensing unit 10 associated with each user "tags" the data with a code identifying a particular person or unit 10, such as known in the art. The server 82 then stores performance data tagged to a particular individual or unit so that the correct information is provided, upon request (such as through the Internet or through the computer 74). Performance data can also be printed through printer 86 for users and persons at the base station 70.

Although the base station 70 can be configured to process substantially raw data signals from units 10 (and particularly from the sensors 14), the base station typically collects performance data directly from the sensing unit 10 for each of a plurality of users and stores all the data, tagged to the particular user, in the server 82. The stored data can then reviewed as required. By way of example, a video station 90 can be included with the base station 70 and users, instructors or judges can review the performance data in conjunction with video data collected during the run by known video systems (or television systems).

With further reference to FIGS. 1A and 1B, the displays 24c, 52 can be one of any assortment of displays known to those skilled in the art. For example, liquid crystal displays (LCDs) are preferred because of their low power consumption (for example, LCDs utilized in digital watches, portable computers and paging units are appropriate for use with the invention). Other suitable displays can include an array of light emitting diodes (LEDs) arranged to display numbers.

The headphones assembly 60 can also be replaced with a heads-up display unit, known in the art, such as described in connection with U.S. Pat. No. 5,162,828, incorporated herein by reference.

Figure 2:
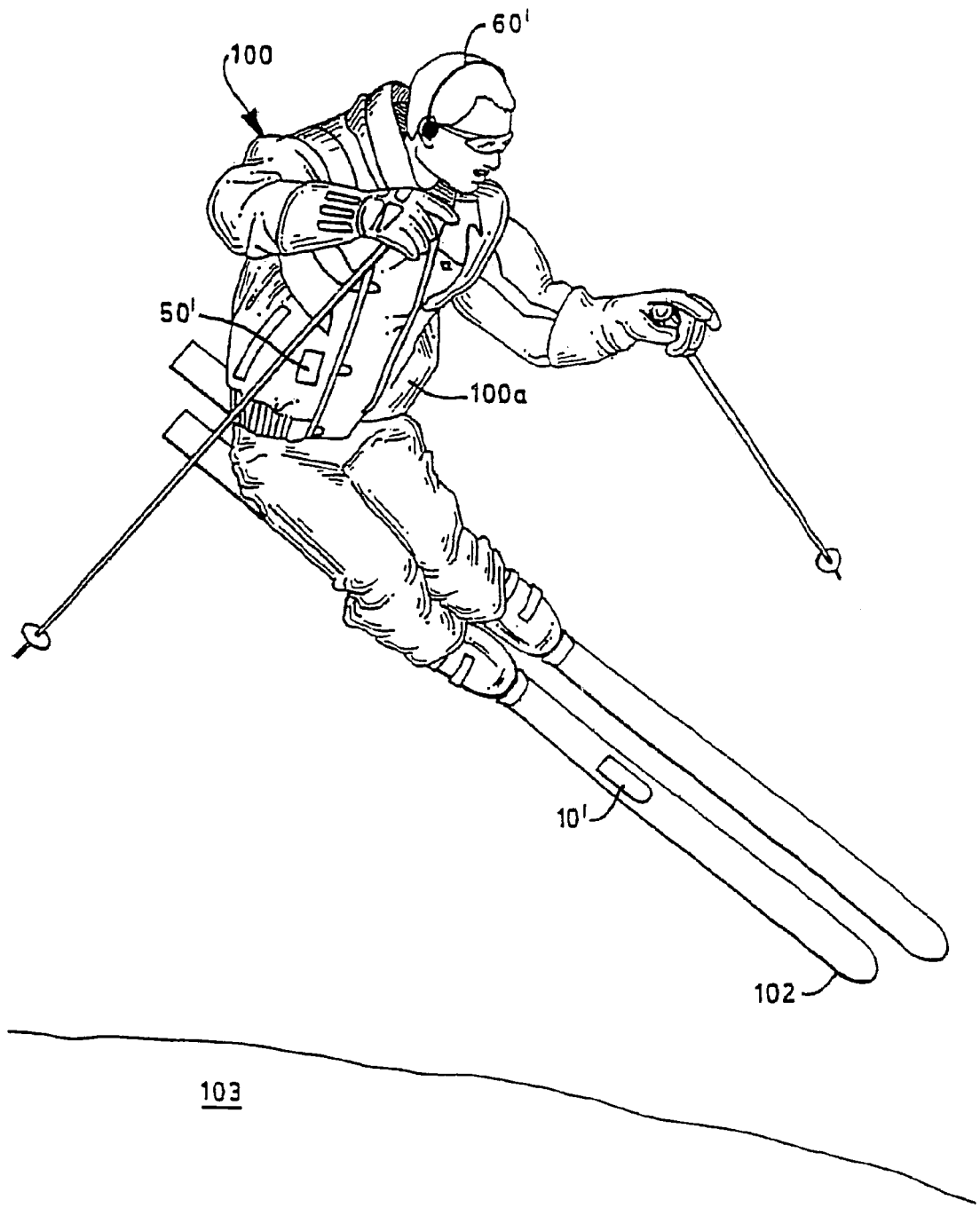
FIGS. 2, 3, 4 and 5 illustrative certain operational uses of the units of FIG. 1.

As illustrated in FIG. 2, the invention in one embodiment operates as follows. The sensing unit 10' is mounted via its housing 32 to a sporting vehicle, such as a snowboard or mountain bike, or such as the ski 102 of FIG. 2. As illustrated, the skier 100 is catching air during a jump off the ground 103. The skier 100 can obtain instantaneous airtime data via headphones 60', discussed above, or he can later retrieve the airtime data through a data unit 50' (shown illustratively on the skier's jacket 100a when typically the unit 50' would be within a pocket or connected to a belt of the skier 100) or at a base station 70' (FIG. 1B).

Figure 3:
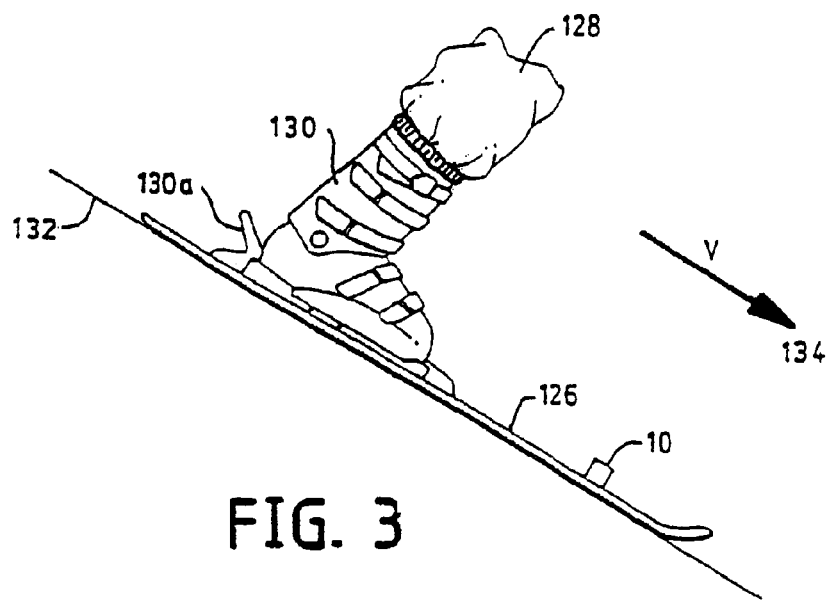

FIG. 3 shows another typical use of the unit 10 of FIG. 1A. In particular, FIG. 3 shows the sensing unit 10 mounted onto a ski 126. As is normal, the ski 126 is mounted to a skier 128 (for illustrative purposes, the skier 128 is only partially illustrated), via a ski boot 130 and binding 130a, and generally descends down a ski slope 132 with a velocity 134. Accordingly, one use of a unit 10 with a speed sensor is to calculate the peak speed of the ski 126 (and hence the skier 128) over a selectable period of time, e.g., during the time of descent down the slope 132. However, the unit 10 also provides information such as drop distance, airtime and power, as described herein, provided the associated sensors are included with the unit 10.

Figure 4:
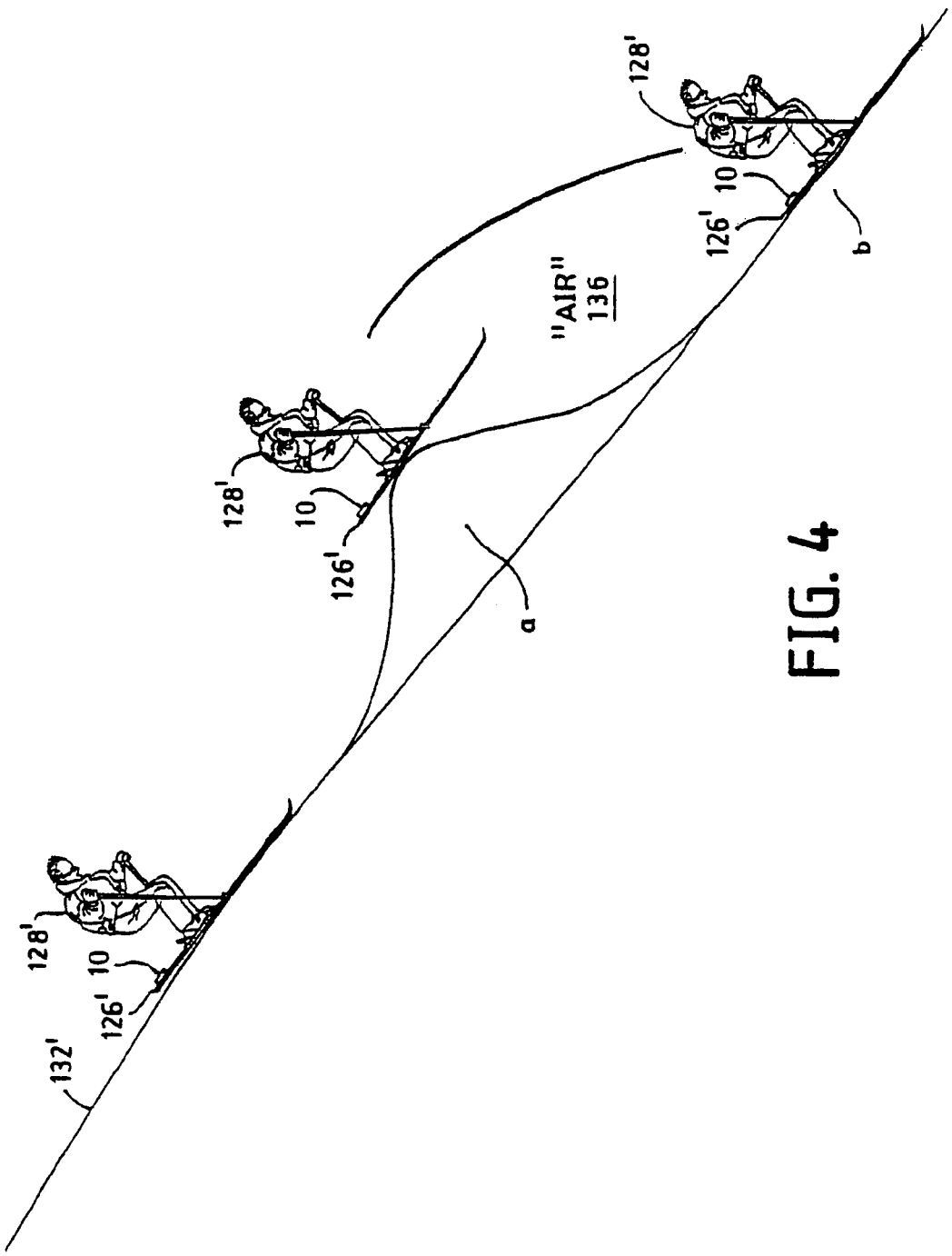

Another use of the unit 10 of FIG. 1A is to calculate the airtime of a vehicle such as the ski 126 (and hence the user 128) during the descent down the slope 132. Consider, for example, FIG. 4, which illustrates the positions of the ski 126' and skier 128' during a lofting maneuver on the slope 132'. The ski 126' and skier 128' speed down the slope 132' and launch into the air 136 at position "a," and later land at position "b" in accord with the well-known Newtonian laws of physics. With an airtime sensor, described above, the unit

10 calculates and stores the total airtime that the ski 126' (and hence the skier 128') experiences between the positions "a" and "b" so that the skier 128' can access and assess the "air" time information.

Figure 5:
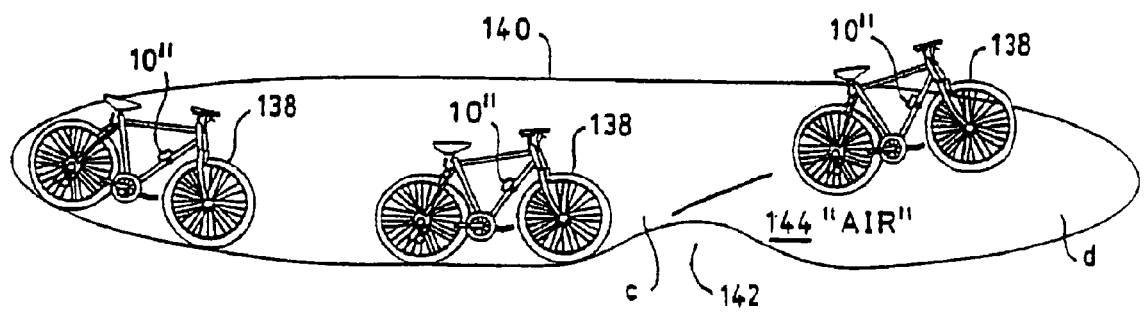

FIG. 5 illustrates a sensing unit 10" mounted onto a mountain bike 138. FIG. 5 also shows the mountain bike 138 in various positions during movement along a mountain bike race course 140 (for illustrative purposes, the bike 138 is shown without a rider). At one location "c" on the race course 140, the bike 138 hits a dirt mound 142 and catapults into the air 144. The bike 138 thereafter lands at location "d". As above, with speed and airtime sensors, the unit 10 provides information to a rider of the bike 138 about the speed attained during the ride around the race course 140; as well as information about the airtime between location "c" and "d".

Airtime sensors such as the sensor 14b of FIG. 1A may be constructed with known components. Preferably, the sensor 14b incorporates either an accelerometer or a microphone. Alternatively, the sensor 14b may be constructed as a mechanical switch that detects the presence and absence of weight onto the switch. Other airtime sensors 14b will become apparent in the description which follows. For background, consider U.S. Pat. No. 5,636,146.

An accelerometer, well known to those skilled in the art, detects acceleration and provides a voltage output that is proportional to detected acceleration. Accordingly, the accelerometer senses vibration—particularly the vibration of a vehicle such as a ski or mountain bike—moving along a surface, e.g., a ski slope or mountain bike trail. This voltage output provides an acceleration spectrum over time; and information about airtime can be ascertained by performing calculations on that spectrum. Specifically, the controller subsystem 12 of FIG. 1A stores the spectrum into memory 12b and processes the spectrum information to determine airtime.

Figure 6A:
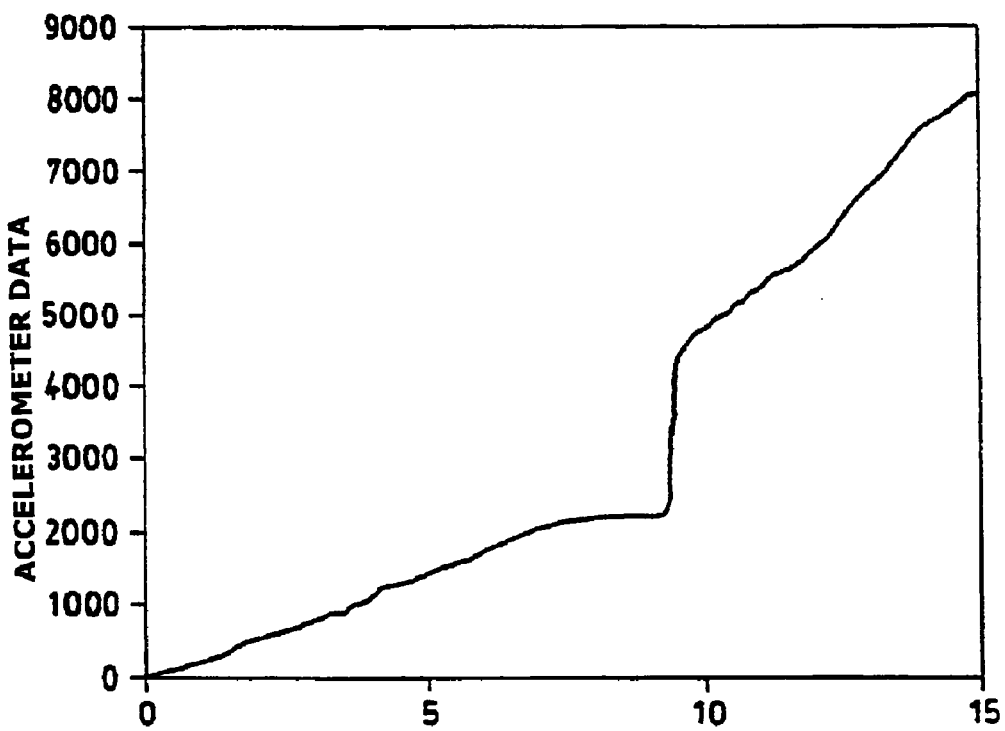
FIGS. 6A and 6B represent processed versions of the data of FIG. 6.
Figure 6B:
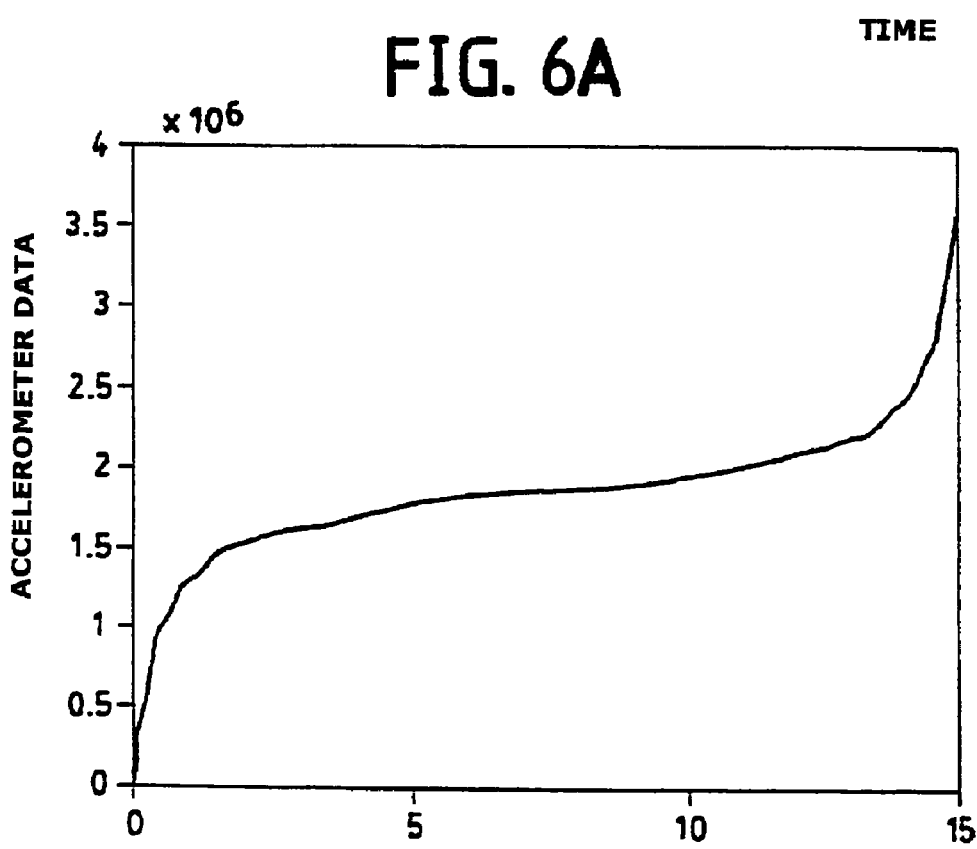
Figure 6:
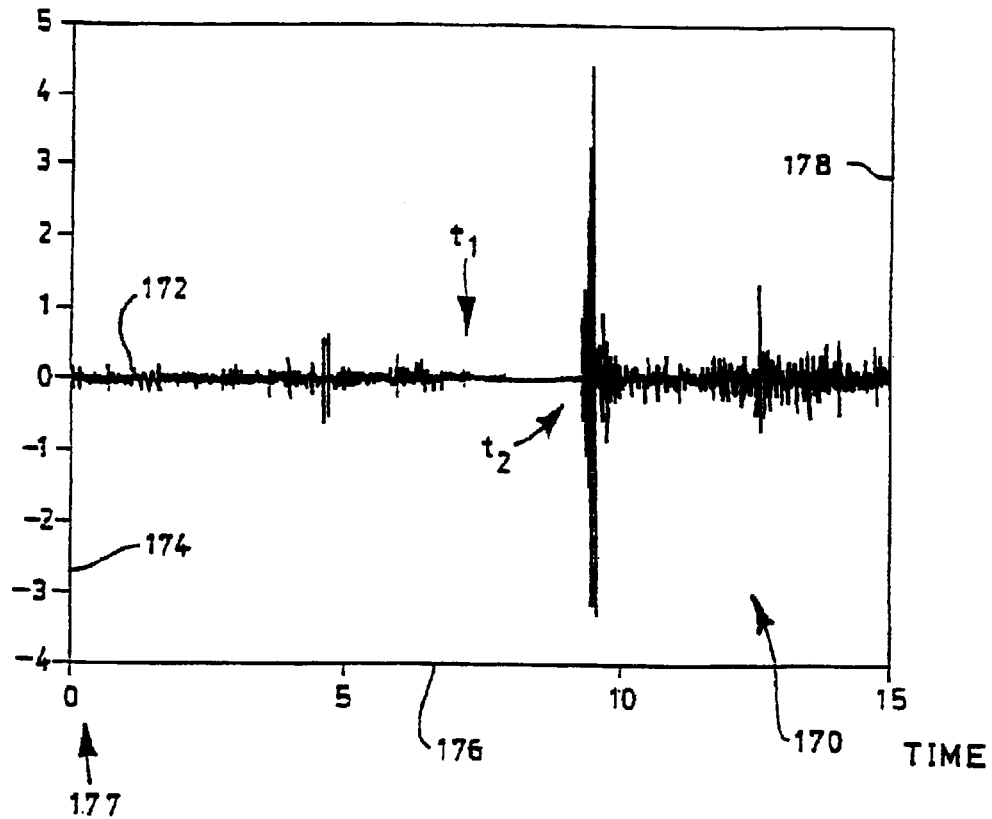
FIG. 6 graphically illustrates actual vibration data taken during a ski jump with an airtime sensor utilizing an accelerometer, in accord with the invention.

FIG. 6 shows a graph 170 of an actual vibrational spectrum 172 acquired by an airtime sensor 14b (utilizing an accelerometer) during a ski jump and stored in memory 12b, in accord with the invention. The airtime sensing unit was mounted to a ski boot which in turn was mounted with a ski binding. The sensitive axis of the accelerometer was oriented substantially vertical to the flat portion of the ski surface. The vertical axis 174 of the graph 170 represents voltage; while the horizontal axis 176 represents time. At the beginning of activity 177—such as when a user of the sensing unit 10 presses the start/stop button 24a—the airtime sensor 14b began acquiring data and transferring that data to the controller subsystem 12 via communication lines 16b. The initial data appears highly noisy and random, corresponding to the randomness of the surface underneath the vehicle (i.e., the ski). At time "$t_1$" the skier launched into the air, such as illustrated as location "a" in FIG. 4; and he landed at time "$t_2$," such as illustrated as location "b" in FIG. 4. The vibrational spectrum 172 between $t_1$ and $t_2$ is comparatively smooth as compared to the spectrum outside this region because the user's vehicle—i.e., the ski boot—was in the air and was not therefore subjected to the random vibrations of the ski slope (i.e., vibrations which travel through the binding, through the boot and into the sensing unit). Accordingly, the relatively smooth spectrum between $t_1$ and $t_2$ is readily discerned from the rest of the spectrum by the controller subsystem 12 and evaluated for airtime; specifically, airtime is $t_2-t_1$.

FIG. 6 also shows that the spectrum stops at the end 178 of the sporting activity, when the controller subsystem stopped taking data (such as in response to an ON/OFF toggle on switch 24a).

Typical accelerometer taken from a skier going down a hill is thus shown in FIG. 6. In order to determine power, or shock, in one aspect, the data is accumulated by taking the absolute value and integrating that data. FIG. 6A graphically shows the result of integrating the data of FIG. 6.

Another method of the invention for determining a measure of power associated with stored accelerometer data is to perform a Fast Fourier Transform on the data and to integrate the magnitude to find the total energy associated therewith. In the plot of FIG. 6B, the data from FIG. 6 was transformed with an FFT routine, and then converted to absolute value, point by point, and integrated, providing one measure of energy.

The data of FIG. 6 can also be reduced to a single number such as via a root-mean-square of the data. This is done by squaring each sample of the data and then summing. The resultant integration can then be divided by the duration of the data acquisition run, giving a mean, with the resulting number rooted. In the case of the FIG. 6, that would provide a value 4.0

A microphone, also well known to those skilled in the art, detects sound waves and provides a voltage output that is responsive to detected sound waves. Accordingly, a microphone, like the accelerometer, mounted to the vehicle senses the vibration of a vehicle, such as a ski or mountain bike, moving along a surface, e.g., a ski slope or mountain bike trail. By way of analogy, consider putting one's ear flat onto a desk and running an object across the desk. As one can readily determine, the movement of the object on the desk is readily heard in the ear. Likewise, a microphone within an airtime sensor 14b readily "hears" the vibrational movements of the vehicle on the surface. Therefore, like the aforementioned accelerometer, a vibrational spectrum such as shown in FIG. 6 is generated by a microphone-based airtime sensor during a user's sporting activity. As above, the controller subsystem 12 utilizes this spectrum to determine airtime.

A microphone is preferably coupled with a coupling layer of material that matches the impedance for the propagation of compression waves (commonly referred to as "sound waves" when in air) between the impedance of the vehicle, e.g., the ski or board, and the microphone transducer, thus transmitting the most "sound" power to the sensor. This "matching layer" of intermediate impedance is commonly used in sonar, as known in the art, and it is easily applied, such as with glue.

The airtime sensor 14b of FIG. 1A can also incorporate a switch that rests below the boot of the ski. Through the switch, the airtime sensor senses pressure caused by the weight of the user within the boot. That is, when the skier is on the ground, the boot squeezes the switch, thereby closing the switch. The closed switch is detected by the controller subsystem 12, FIG. 1A, as a discrete input. When a skier jumps into the air, for example, the switch opens up by virtue of the fact that relatively no weight is on the switch; and this opened switch is also detected and input into controller subsystem 12. The controller subsystem 12 counts at known time intervals (clock rates) for the duration of the opened switch, corresponding to the jump, to determine airtime.

Another airtime sensor 14b of the invention changes capacitance as a function of a change of applied pressure. For example, a material beneath the boot that changes capacitance under varying applied pressures can be used for this airtime sensor. The change in capacitance is converted to a digital signal by conditioning electronics within the controller subsystem 12 to determine airtime.

Figure 7:
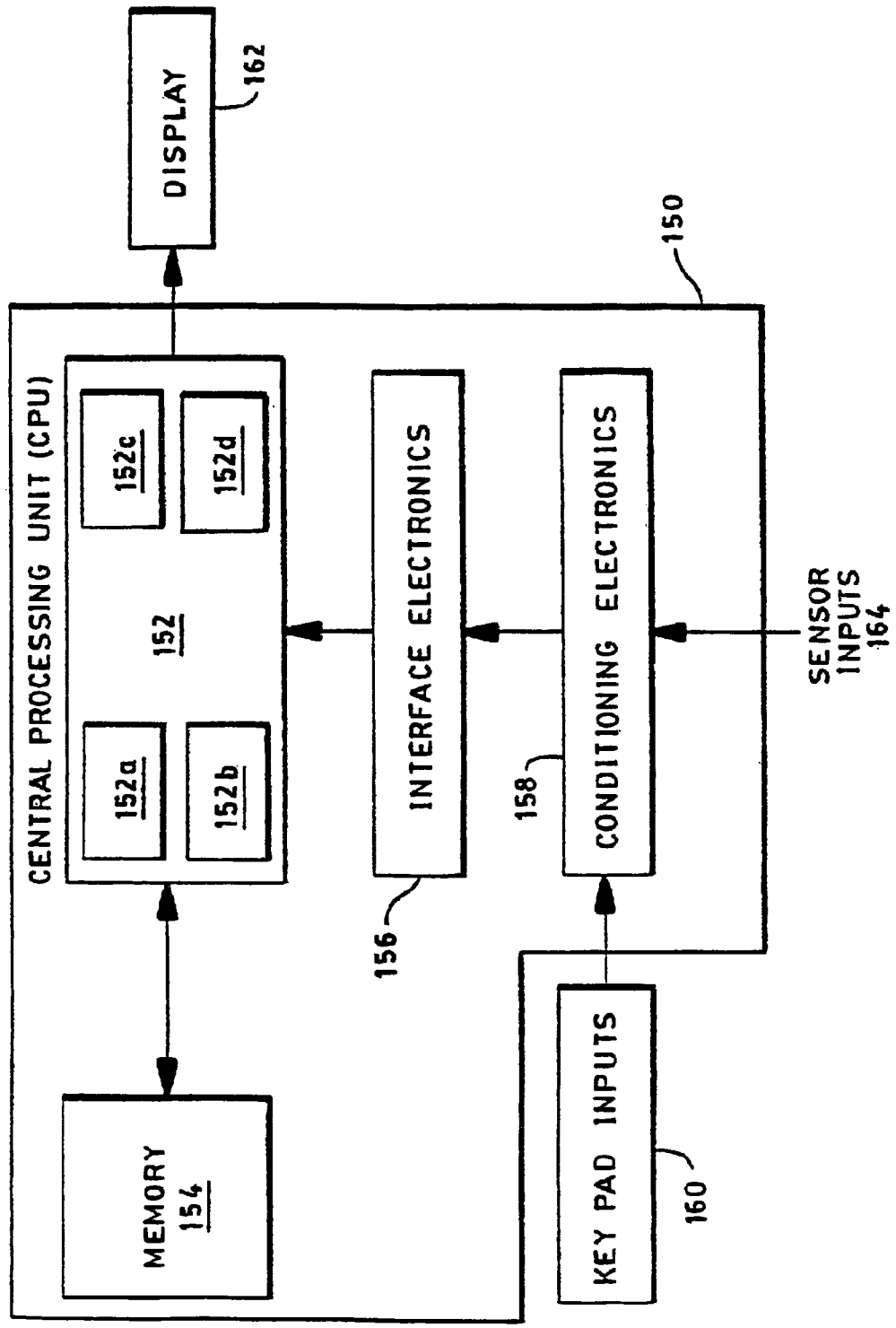
FIG. 7 schematically illustrates a controller subsystem constructed according to the invention and which is suitable for use in the sensing unit of FIG. 1.

The controller subsystem of the invention is constructed with known components, such as shown in FIG. 7, which illustrates an alternative configuration to the subsystem 12 of FIG. 1A. Specifically, FIG. 7 shows controller subsystem 150 constructed according to the invention and including a Central Processing Unit (CPU) 152, memory 154, interface electronics 156, and conditioning electronics 158. The user interface 160, such as the interface 24 of FIG. 1A, and including the button inputs 24b, connects to the subsystem 150 such as shown and directly to the conditioning electronics 158. The display 162, such as the display 24c of FIG. 1A, preferably connects to the subsystem 150 such as shown and directly to the CPU 152.

The CPU 152 includes a microprocessor 152a, Read Only Memory (ROM) 152b (used to store instructions that the processor may fetch in executing its program), Random Access Memory (RAM) 152c (used by the processor to store temporary information such as return addresses for subroutines and variables and constant values defined in a processor program), and a master clock 152d. The microprocessor 152a is controlled by the master clock 152d that provides a master timing signal used to sequence the microprocessor 152a through its internal states in its execution of each processed instruction. The clock 152d is the master time source through which time may be deduced in measuring velocity or air time (for example, to determine the elapsed time from one event to another, such as the lapsed time "$t_1$" to "$t_2$" of FIG. 6, the clock rate provides a direct measure of time lapse).

The microprocessor subsystem 150, and especially the CPU 152, are preferably low power devices, such as CMOS; as is the necessary logic used to implement the processor design.

The subsystem 150 stores information about the user's activity in memory. This memory may be external to the CPU 152, such as shown as memory 154, but preferably resides in the RAM 152c. The memory may be nonvolatile such as battery backed RAM or Electrically Erasable Programmable Read Only Memory (EEPROM). Sensor inputs 164 from the various sensors 14 are connected to the conditioning electronics 158 which filters, scales, and, in some cases, senses the presence of certain conditions, such as zero crossings. This conditioning essentially cleans the signal up for processing by the CPU 152 and in some cases preprocesses the information. These signals are then passed to the interface electronics 156, which converts (by A/D) the analog voltage or currents to binary ones and zeroes understood by the CPU 152.

The invention also provides for intelligence in the signal processing, such as achieved by the CPU 152 in evaluating historical data. For example, airtime may be determined by the noise spectra that changes abruptly, such as indicating a leap, instead of a noise spectra representing a more gradual change that would occur for example when a skier slows to a stop. As previously noted, a minimum quiet time is required, in certain embodiments of the invention, to differentiate between airtime and the natural motions associated with turning and skiing (e.g., jump skiing). Further, in other certain embodiments, a maximum time is also programmed to differentiate airtime from an abrupt stop, such as standing in a lift line.

In accord with the invention, if speed is calculated within the sensing unit 10, FIG. 1A, then the speed sensor 14a can incorporate one or more of the following: (1) a pitch detection system that detects the "pitch" of the vibrational spectrum and that converts the pitch to an equivalent speed; (2) a laser-based, RF-based, or sound-based Doppler module; (3) accelerometers or microphones; (4) pressure transducers; (5) voltage-resistance transducers; and (6) a DSP subsystem that quantifies and bins accelerometer or sound data according to frequency. Other speed sensors 14a will become apparent in the description which follows. For background, consider U.S. Pat. No. 5,636,146.

As described above, detection of airtime is facilitated by detecting motion, which is less difficult that determining speed. The above speed sensors are thus also suitable as "motion" detect sensors that assist the controller subsystem 12 to logic out unwanted data, e.g., airtime data when standing in line.

In accord with one embodiment, a vibrational spectrum is obtained through an airtime sensor with an accelerometer or microphone embodiment; and this spectrum is analyzed by the controller subsystem to determine the pitch of the vibration and, thereby, the equivalent speed. By way of example, note that a skier generates a scraping sound on hard-packed snow and ice. When the skier changes velocity, that scraping sound changes in pitch (or in volume). By calibrating the subsystem 12 to associate one pitch (or volume) as one velocity, and so on, the speed of the vehicle (e.g., ski and mountain bike) is determined by spectral content. One technique for determining the "pitch" of the spectrum is to determine the best fit sine wave to the vibrational spectrum data. This sine wave has a frequency, or "pitch" that may be quantified and used to correlate velocity. The spectrum can also be sampled and "binned" according to frequency, as discussed below, to determine changes in volume at select frequencies (or ranges of frequencies) which provide speed correlation.

Spectral content may be determined, at least in part, by the conditioning electronics 158 of FIG. 7. The electronics can also assess the rise times to infer a bandwidth of the information. The conditioning electronics 158 and/or CPU 152 can also measure the time between successive zero crossings, which also determines spectral content.

Figure 8:
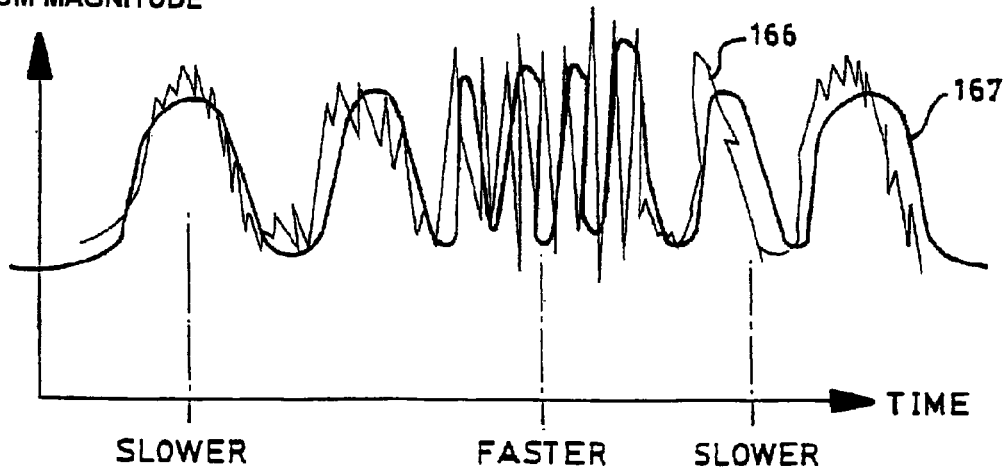
FIG. 8 illustrates one exemplary pitch-detection process, in accord with the invention, which is used to determine speed.

For example, FIG. 8 illustrates a spectrum 166 generated from combination speed and airtime sensor 14a, 14b in the form of an accelerometer or microphone. The spectrum 166 thus represents an acceleration spectrum or sound spectrum such as described herein. The controller subsystem 12 of FIG. 1A evaluates the spectrum 166 and generates a best-fit sine wave 167 to match the primary frequency of the spectrum 166 over time. FIG. 8 shows illustratively a situation where a vehicle, such as a ski, moves slowly at first, corresponding to a lower sine-wave frequency, then faster, corresponding to a higher frequency sine wave, and then slower again. This pitch transition is interpreted by the controller subsystem as a change of speed. Specifically, the controller subsystem has calibration data to associate a certain frequency with a certain speed, for the given vehicle; and speed is thus known for the variety of pitches observed during an activity, such as illustrated in FIG. 8.

Variations in the character of the snow, and other environmental factors such as sun exposure, and user altitude, can also be factored in speed sensing, in another aspect. Further, speed spectra likely varies depending on the characteristic spatial scale(s) of the ground, e.g., the snow for a fixed skier speed. These spatial scales are set by the temperature at which the snow was deposited, thawing and refreezing cycles, and the sun exposure even within a day.

It should be noted that pitch information (or volume data) is surface dependent (and vehicle dependent). For example, a ski-over-snow-speed-spectrum has a different spectrum than a bicycle-over-ground-spectrum. Accordingly, different calibrations should be made for different vehicles and speeds, in accord with the invention. Further, certain spectrums may actually decrease in frequency as speed increases, which should be calibrated to obtain correct speed information. These calibrations are typically programmed into the controller subsystem memory, e.g., the memory 12b of subsystem 12 of FIG. 1A. Further, in certain embodiments of the invention, the sensing unit (or data unit or base station, as appropriate)

stores different spectrum calibrations for different activities so that a user can move the sensing unit from one sport to another. Accordingly, one or more buttons such as the buttons 24b are used to selectively access the different spectrum calibrations.

It is well known that Doppler radar is used by police vehicles to detect speed; and a speed sensor incorporating a Doppler module can be used to determine speed. U.S. Pat. Nos. 5,636,146, 4,722,222 and 4,757,714 provide useful background.

Figure 9:
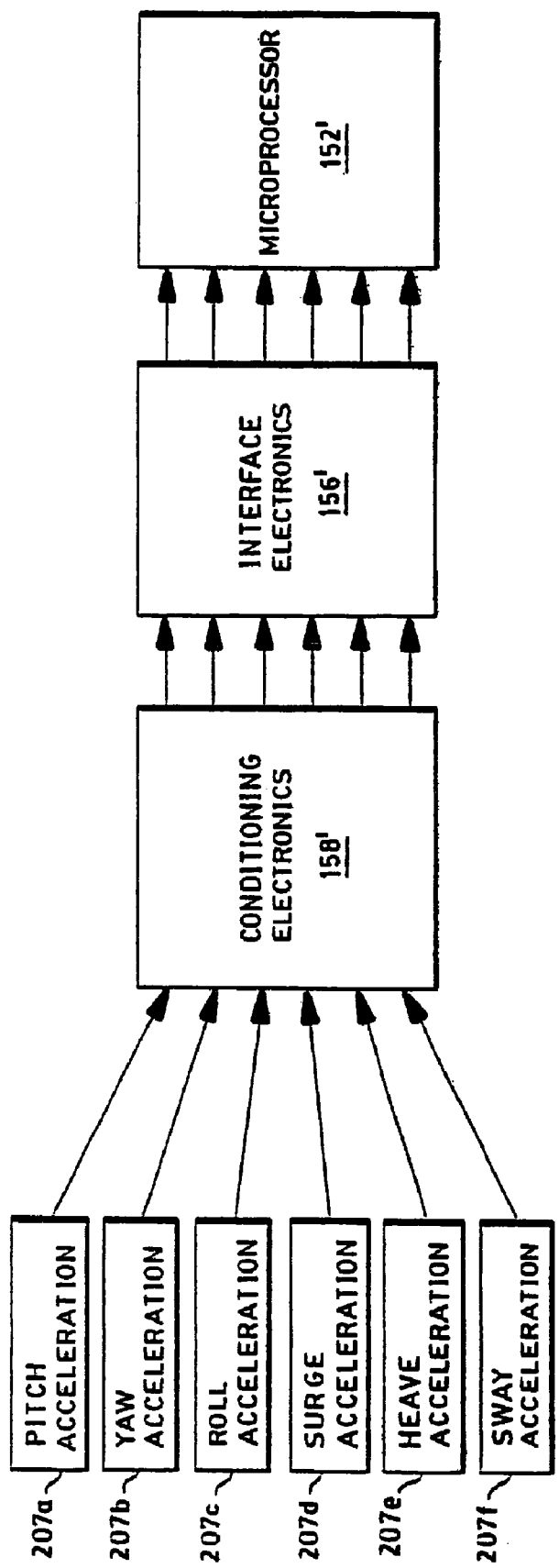
FIG. 9 schematically illustrates process methodology of converting a plurality of acceleration values to speed, in accord with the invention.

FIG. 9 schematically illustrates process methodology, according to the invention, which converts a plurality of acceleration inputs to speed. For example, when a plurality of six accelerometers are connected to a controller subsystem, the process methodology of the invention is preferably shown in FIG. 9. Specifically, six accelerometers are connected with various sensitive orientations within a speed sensing unit 14a to collect pitch 207a, yaw 207b, roll 207c, surge 207d, heave 207e, and sway 207f accelerations. These accelerations are conditioned by the conditioning electronics 158' through the interface electronics 156' and CPU 152' to calculate speed, such as known to those skilled in the art of navigational engineering (for example, *Gyroscopic Theory, Design, and Instrumentation* by Wrigley et al., MIT Press (1969); *Handbook of Measurement and Control* by Herceg et al, Schaevitz Engineering, Pensauker, N.J., Library of Congress 76-24971 (1976); and *Inertial Navigation Systems* by Broxmeyer, McGraw-Hill (1964) describe such calculations and are hereby incorporated herein by reference). The elements 158', 156' and 152' are similar in construction to the elements 158, 156 and 152 described in connection with FIG. 7.

Figure 10:
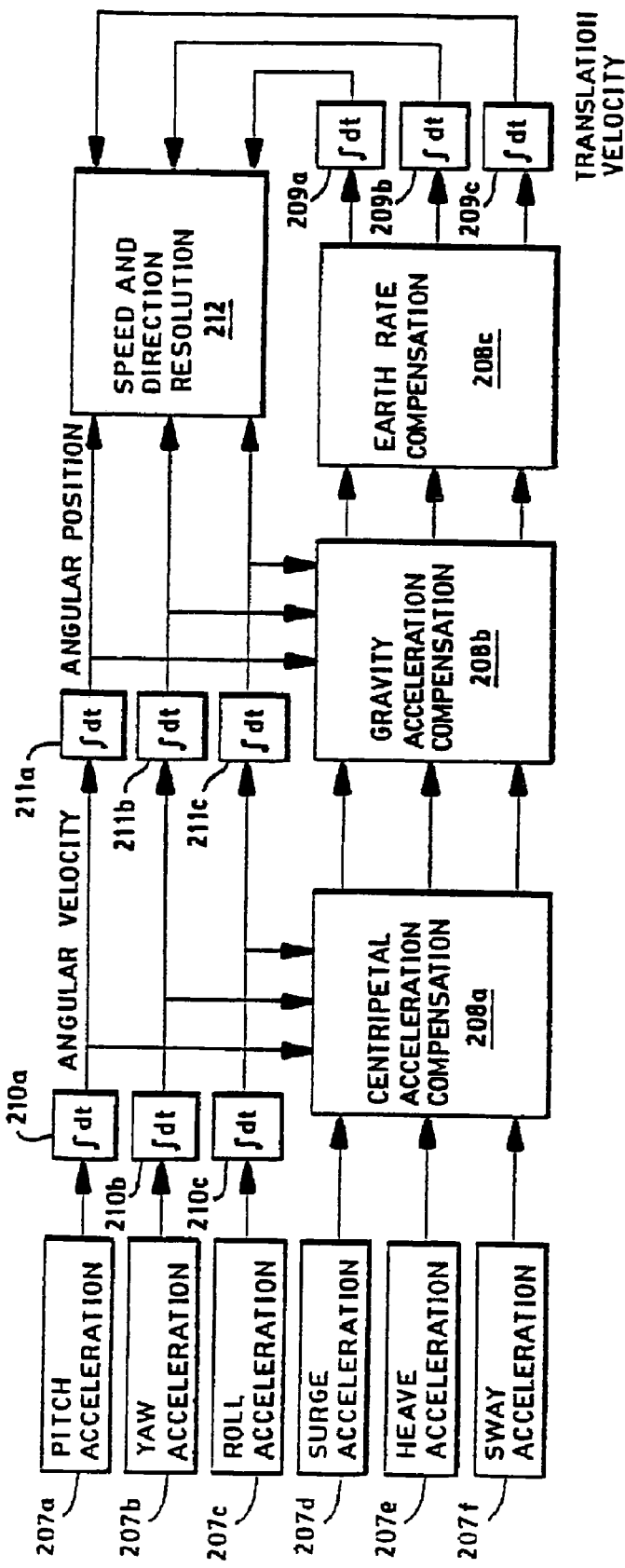
FIG. 10 schematically illustrates process methodology of calculating speed, direction, and/or vehicle drop distance, in accord with the invention, by utilizing accelerometer-based sensors.

FIG. 10 schematically illustrates further process methodologies according to the invention wherein the six acceleration inputs 207a-207f are processed by a controller subsystem of the invention (e.g., subsystem 12 of FIG. 1A) such that centripetal, gravitational, and earth rate compensations are performed so that the various accelerations are properly integrated and compensated to derive speed (and even direction and distance). Specifically, a controller subsystem of the FIG. 10 embodiment includes a centripetal acceleration compensation section 208a which compensates for motions of centripetal accelerations via inputs of surge 207d, heave 207e, and sway 207f. A gravity acceleration compensation section 208b in the subsystem further processes these inputs 207d-207f to compensate for the acceleration of gravity, while a earth rate compensation section 208c thereafter compensates for the accelerations induced by the earth's rotation (e.g., the earth rate acceleration at the equator is approximately opposite in direction to the force of gravity).

Also shown in FIG. 10 are translational integrators 209a-209c which convert the compensated accelerations from inputs 207d-207f to translational velocities by integration. Integrators 210a-210c likewise integrate inputs of pitch 207a, yaw 207b, and roll 207c to angular velocity while integrators 211a-211c provide a further integration to convert the angular velocities to angular position. The angular positional information and translational velocity information is combined and processed at the speed and direction resolution section 212 to derive speed and direction. Preferably, the subsystem with the components 208, 209, 210, 211 and 212 is calibrated prior to use; and such calibration includes a calibration to true North (for a calibration of earth rate).

It should be noted that fewer of the inputs 207a-207f may be used in accord with the invention. For example, certain of the inputs 207a-207f can be removed with the section 208a so that centripetal acceleration is not compensated for. This results in an error in the calculated speed and direction; but this error is probably small so the reduced functionality is worth the space saved by the removed elements. However, with the increased functionality of the several inputs 207a-207f, it is possible to calculate drop distance in addition to speed because distance in three axes is known. Therefore, the invention further provides, in one embodiment, information for displaying drop distance achieved during any given airtime, as described above.

As used herein, "cookie" measurements refer to one technique of the invention for measuring speed. In this method, for example, the speed sensor drops a measurable entity—e.g., electronic charge—into the snow and then picks it up later at a known distance away to determine the speed. The "charge" in this example is the "cookie."

In skiing, for example, this method involves dropping a cookie as the ski travels and then detecting the cookie at a known distance down the length of the ski. The time between placement and detection given a known length between the two occurrences determines the speed. A cookie therefore represents the placement of some measurable characteristic in the snow underneath. This characteristic may be electrical charge, magnetic moments, a detectable material such as ink, perfume, fluorescent dye or a radiation source. The cookies may be dropped at a constant rate, i.e. cookies per second, or at a fixed distance between cookies. In such cases the cookies are said to be dropped in a closed loop fashion. Also the amount of charge, magnetic moment, or detectable material may be controlled so that the detection occurs just above threshold. This tends to minimize the amount of electrical power used and to minimize the amount of material dispensed. In one aspect, the cookies correspond to dots of dye that are dropped at regularly spaced intervals and which glow when irradiated with a pumping light spectrum, for example a UV pump to drive fluorescence response in blue/blue-green, or a red pump to drive fluorescence in the IR.

Figure 13:
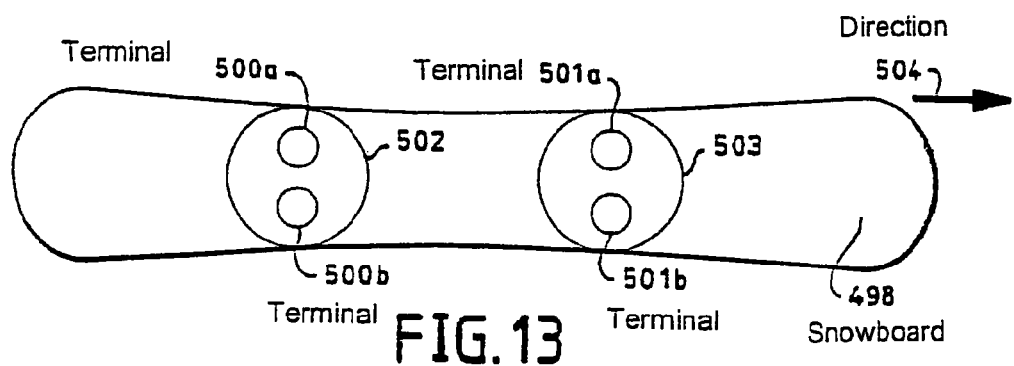
FIGS. 13 and 14 show top and side cross-sectional views, respectively, of a speed sensor of the invention, coupled to a snowboard, for determining speed by utilizing charge cookies.
Figure 14:
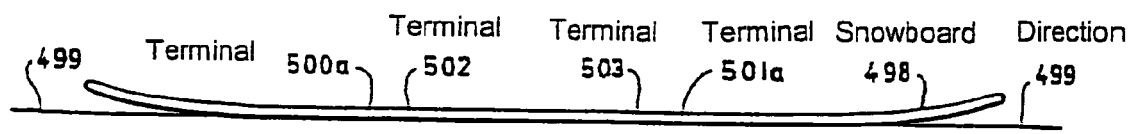

In FIGS. 13 and 14, a snowboard 498 traveling in a direction 504 has two sets of electrodes attached to the ski. The first electrode set 503 is used to charge a small amount of snow 499 by applying an electric potential across terminals 501a and 501b. The potential in that snow 499 is then read by the second set of electrodes 502, accomplished by sampling the potential between terminals 500a and 500b.

Figure 15:
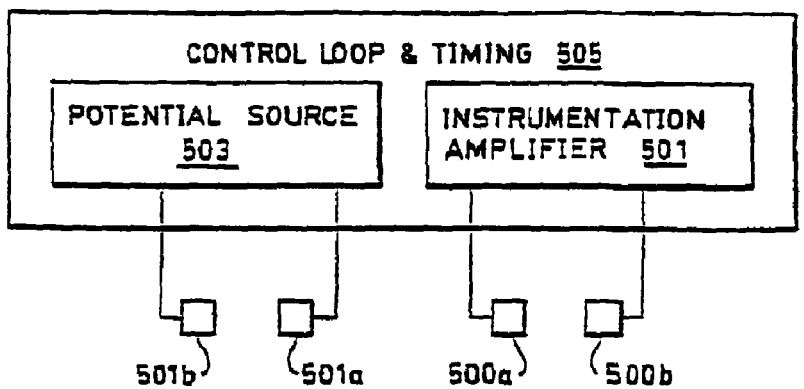
FIG. 15 shows a schematic diagram for processing the speed sensor of FIGS. 13 and 14.

Since the level of charge in the snow 499 is quite low, an instrumentation amplifier may be used to condition the signal, such as known to those skilled in the art. FIG. 15 shows the charge and detection loop according to one preferred embodiment. A potential source (e.g., a battery such as battery 30, FIG. 1A) with an electrode set 503 are used to charge the first electrodes 501a, 501b. When the output of the instrumentation amplifier 501 is above a predetermined threshold, the control and timing circuit 505 triggers a flip-flop (not shown) that notifies the controller subsystem 12, FIG. 1A, that the charge is detected. The time that transpired between placing the charge at 503 to detecting the charge at 502 is used to determine speed. The speed is the distance between the two sets of electrodes 503 to 502 divided by the time between setting and receiving the charge. The functionality of the timing and control circuit 505 can be separate or, alternatively, can be integrated with the controller subsystem such as described herein.

The second set of electrodes 502 that is used to detect the charge may also be used to clear the charge such as by driving a reverse voltage (from the control and timing circuit 505 and through direct circuitry to the electrodes 502). In this manner to total charge resulting from the ski traversing the field of snow will be zero so that there will be no charge pollution. Also it will not confuse another ski speed detection system according to the invention.

In summary, the speed sensor of FIGS. 13-15 thus include two electrode pairs, 503, 502.

Figure 16:
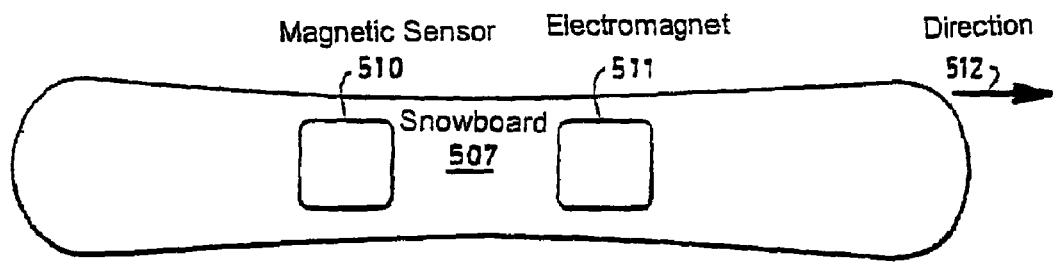
FIGS. 16 and 17 show top and side views, respectively, of another embodiment of a speed sensor, according to the invention, coupled to a snowboard and utilizing magnetic cookies to determine speed.
Figure 17:
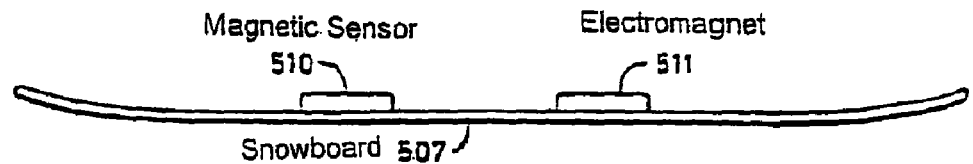

The situation described above is also applicable to magnetic moment cookies. In FIGS. 16 and 17, for example, a snowboard 507 shown traveling in a direction 512 has an electromagnet 511 mounted on top of the snowboard 507 and a magnetic sensor 510 at a rearward position. As the snowboarder skis along direction 512 the electromagnet 511 impresses a magnetic moment into the snow and water that resides under the snowboard 507. This is done by asserting a strong magnetic field from the electromagnet 511 and through the snowboard 507 for a short period of time. This polarization is then detected by the magnetic sensor 510. The period of time it takes from creating the magnetic moment at 511 to detecting it at 510 is used in determining the speed of the snowboard 507 (such as through control and timing circuitry described in connection with FIG. 15). The magnetic sensor 510 may also be used to cancel the magnetic moment so that the total magnetic moment will be zero after the ski travels from placement through detection and removal.

Those skilled in the art should appreciate that the elements 510, 511 are shown grossly separated, for purposes of illustration. Placing the elements closer (and preferably within the same housing 32, FIG. 1A) increases the required response time of the controller subsystem, though it decreases the amount of power required to detect the signal (since the cookie signal is stronger over a shorter period).

Figure 18:
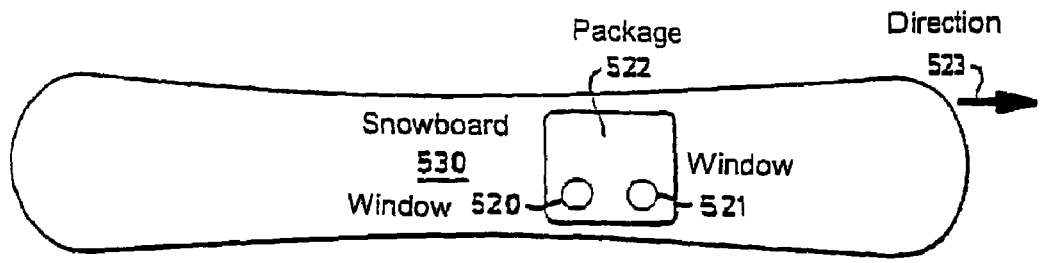
FIGS. 18 and 19 show top and side cross-sectional views, respectively, of another embodiment of a speed sensor, according to the invention, coupled to a snowboard and utilizing optical windows to determine speed.
Figure 19:
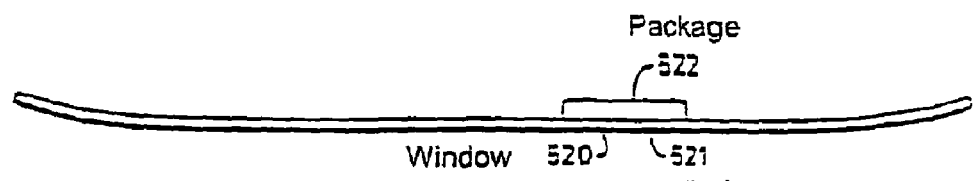

A similar speed sensing system is shown in FIGS. 18 and 19. Specifically, the speed sensor of FIG. 18 includes an optical correlation subsystem with a laser source and receiver contained in package 522. The laser is directed through two windows 520 and 521 within a snowboard 530. The laser backscatter is cross correlated over time between the two windows 520, 521. This means that the two time signals are multiplied and integrated over all time with a fixed time delay between the two signals. The time delay between the two backscatter signals that yields the highest cross correlation is the period of time the snowboard takes to travel the distance of the two windows 520, 521. The speed of the snowboard 530 is determined by knowing the window separation distance. The source does not have to be a laser but can be noncoherent visible light, infrared or any high frequency electromagnetic radiation source.

One drop distance sensor 14c of the invention utilizes an altimeter such as manufactured by Sensym, Inc. The altimeter is calibrated relative to height variations and the sensing unit 10 thereafter monitors pressure change to assess drop distance. Accordingly, in the preferred embodiment, such a drop distance sensor operates with an airtime sensor 14b since drop distance is generally only meaningful in connection with a jump. When the sensing unit 10 detects an airtime, the same period is evaluated through the altimeter to determine drop distance over that period. Accordingly, altimeter data should be stored in the memory 12b (or alternatively in the memory 50b, or in the base station 70) for at least the period of the longest expected airtime (e.g., greater than five seconds for snowboarding, or greater than the period set by the user).

Drop distance can also be determined through a drop distance sensor that includes a plurality of accelerometers, such as shown in FIGS. 9 and 10. Through integration of appropriate acceleration vectors indicative of a user's movement perpendicular to the ground, drop distance is determined. A double integration of accelerometers in the direction perpendicular to ground (or thereabouts) during an airtime period provides the correct signals to determine skier height.

It should be apparent to those in the art that the accelerometers of FIGS. 9 and 10 provide sufficiently detailed information such that the entire sensing unit can be mounted to a user of the system directly, rather than onto a vehicle. With the scope of the compensations described in connection with FIG. 10, for example, movements of the human body, e.g., centripetal motions, may be compensated for to derive speed and/or airtime information that is uncorrupted by the user's movements. Such compensations, however, require powerful processing capability.

Other features can also be determined in accord with the invention such as through measurements with the system of FIG. 10. For example, once you know your starting velocity, you can measure distance traveled and height above the ground by knowing the air time for a given jump. Other ways of doing this are by using accelerometers to integrate the height distance. The preferred way of determining distance is to know your velocity at the jump start location, such as described herein, and to use the airtime to establish a distance traveled, since distance is equal to velocity times time (or airtime).

For height, a sensing unit of the invention also determines height by looking at the time to reach the ground during an airtime. That is, once in the air, you are accelerating towards the ground at 9.81 meters per second$^2$ (at sea level). The sensing unit thus first determines the time for which there is no more upwards movement (such as by using an accelerometer or level sensor that knows gravity direction and which changes directions at the peak, or by using circuitry which establishes this movement, or by determining the angle immediately prior to launch to quantify a bias distance or time to a default measure), and then calculate the distance traveled (in height) by knowing that the default measure is equal to $\frac{1}{2}at^2$, where a is the acceleration of gravity (9.81 m/s$^2$) and t is the airtime after the peak height is reached. If the person does not travel upwards or downwards at the start of a jump, then the height is simply $\frac{1}{2}at^2$ where t is the entire airtime.

Figure 11:
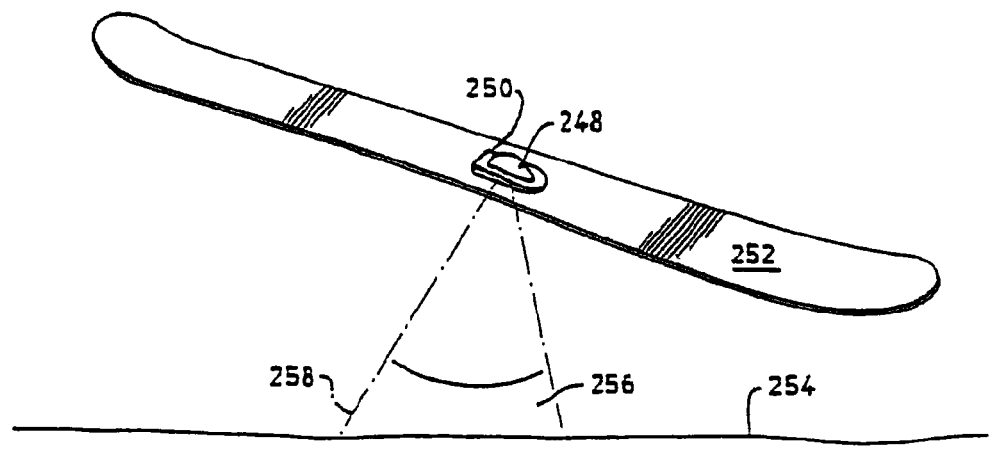
FIG. 11 illustrates methodology for measuring drop distance, speed and/or airtime, in accord with the invention, by utilizing a Doppler module as a drop distance, speed, and/or airtime sensor.

A Doppler module can additionally provide height information; and thus a Doppler module can function as both a speed sensor 14a and a drop distance sensor 14c. Further, since the impedance changes when a vehicle to which the Doppler module leaves the ground, the Doppler module can further function as an airtime sensor 14b. By sweeping the frequency through various frequencies, as known in the art, the signal frequency mix can be monitored to determine altitude relative to the direction of the antenna lobes (typically such Doppler systems are used as microwave ranging systems). Preferably, therefore, there are two antennas: one to perform Doppler speed, with high spatial accuracy in the antenna lobe so that speed is achieved, and another antenna to provide a lobe that roughly covers the ground area in about a 60 degree cone under the user so as to achieve first-return distance measurement. With reference to FIG. 11, a Doppler module 248 functions as the drop distance sensor and resides within a sensing unit 250 mounted to a snowboard 252 (shown in the air, above the ground 254). The radar or microwave beam 256 from the module 248 extends in a cone 258 to adequately cover the ground 254 so as to provide the correct measure of height on a first return bases (that is, any portion of the beam 256 which first creates a Doppler signal sets the height; other height measurements can alternatively be used, including utilizing average return data). A cone 256 of angle Φ) (e.g., 25-70 degrees in solid angle) provides adequate coverage. The Doppler antenna signal fills the conical beam 256 so as to determine drop distance from any orientation of the vehicle (i.e., the snowboard 252), so long as that orientation relative to ground is less than the angle Φ.

The Doppler module 248 may also be used as an airtime sensor since its signal strength or form changes when the vehicle 252 is off the ground. This change of signal is thus detected by the controller subsystem to determine airtime.

Figure 12:
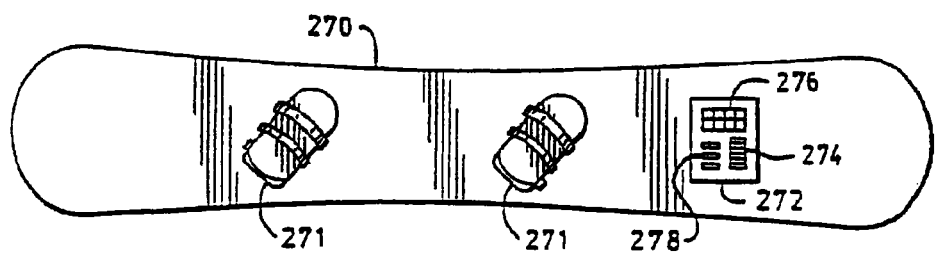
FIG. 12 illustrates an improvement to a snowboard, in accord with the invention.

FIG. 12 shows a representative top view for one other snowboard constructed in accord with the invention. Specifically, a snowboard 270, with boot holder 271, incorporates a sensing unit 272 constructed according to the invention. The unit 272 has a display 274, a user interface 276 that provides a user with buttons to selectively access performance data, as described above, and one or more sensors 278 to provide data to the controller subsystem to quantify performance data. One sensor 278, for example, can include the Doppler module 248 of FIG. 11.

Figure 20:
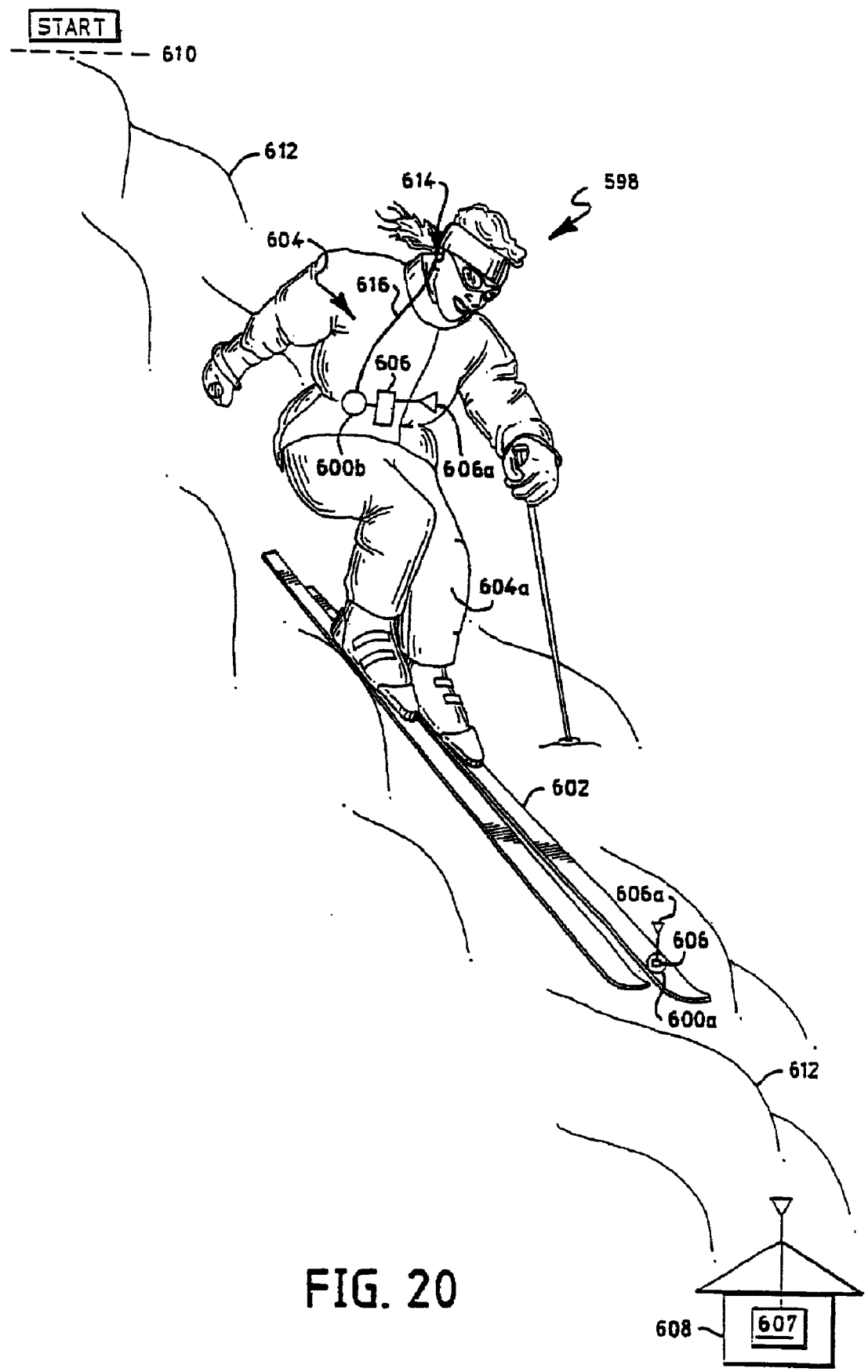
FIG. 20 shows a schematic perspective view—not to scale—of a skier engaged in competition on a mogul course and of a system, constructed according to the invention, for monitoring two power values to quantitatively measure mogul skiing performance.

FIG. 20 illustrates one embodiment of a bump skier 598 utilizing two power sensing units 600 in a mogul competition on a slope 612 (note that the skier is grossly over-sized relative to the slope 612, for purposes of illustration). One power sensing unit 600A mounts to the ski 602 (or alternatively to the user's lower leg 604a), and another power sensing unit 600B mounts or attaches to the user's upper body 604. An RF signal generator 606 communicates (via antenna 606a) the power values to a controller 607 (e.g., similar to the computer and server 74, 82 of FIG. 1B) at a base facility 608 (e.g., where the judges for the competition reside). Those skilled in the art should appreciate that one or both power sensing units 600 can communicate the information to the base 608, as shown; however, one power unit can also communicate to the other power unit so that one unit 600 communicates to the base 608. However, in either case, an RF transmitter is needed at each sensing unit 600 (similar to the data transmit section 22, FIG. 1A). Alternatively, other inter-power meter communication paths are needed, e.g., wiring, laser or IR data paths, and other techniques known to those in the art, such as discussed herein.

The combined signals from the units 600 provides a force differential between the lower legs 604a and the upper body 604, giving an actual assessment of a competitor's performance. A computer 607 at the base station 608 divides one signal by the other to get a ratio of the power values measured by the two units 600 during the run. The units 600 start transmitting data at the starting gate 610 and continue to transmit data to the base 608 during the whole run on the slope 612. The units 600 can also be coupled to the user via a microphone 614 (and wire 616) to provide a hum or pitch which tells that user how effective his/her approach is. Although it is not shown, one or both units 600 have controller subsystems so as to enable the features described herein in connection with power sensing units. For example, a microprocessor can be used to provide a power measurement in "g's" for the competitor once she reaches the base 608.

Those skilled in the art should appreciate that one of the units 600 can alternatively process the power values (e.g., divide the instantaneous power value of one unit by the power value of the second unit, to provide a ratio) generated by each of the units and can transmit a ratio of the values to the base station 608, rather than require the base station to perform the calculation.

Figure 21:
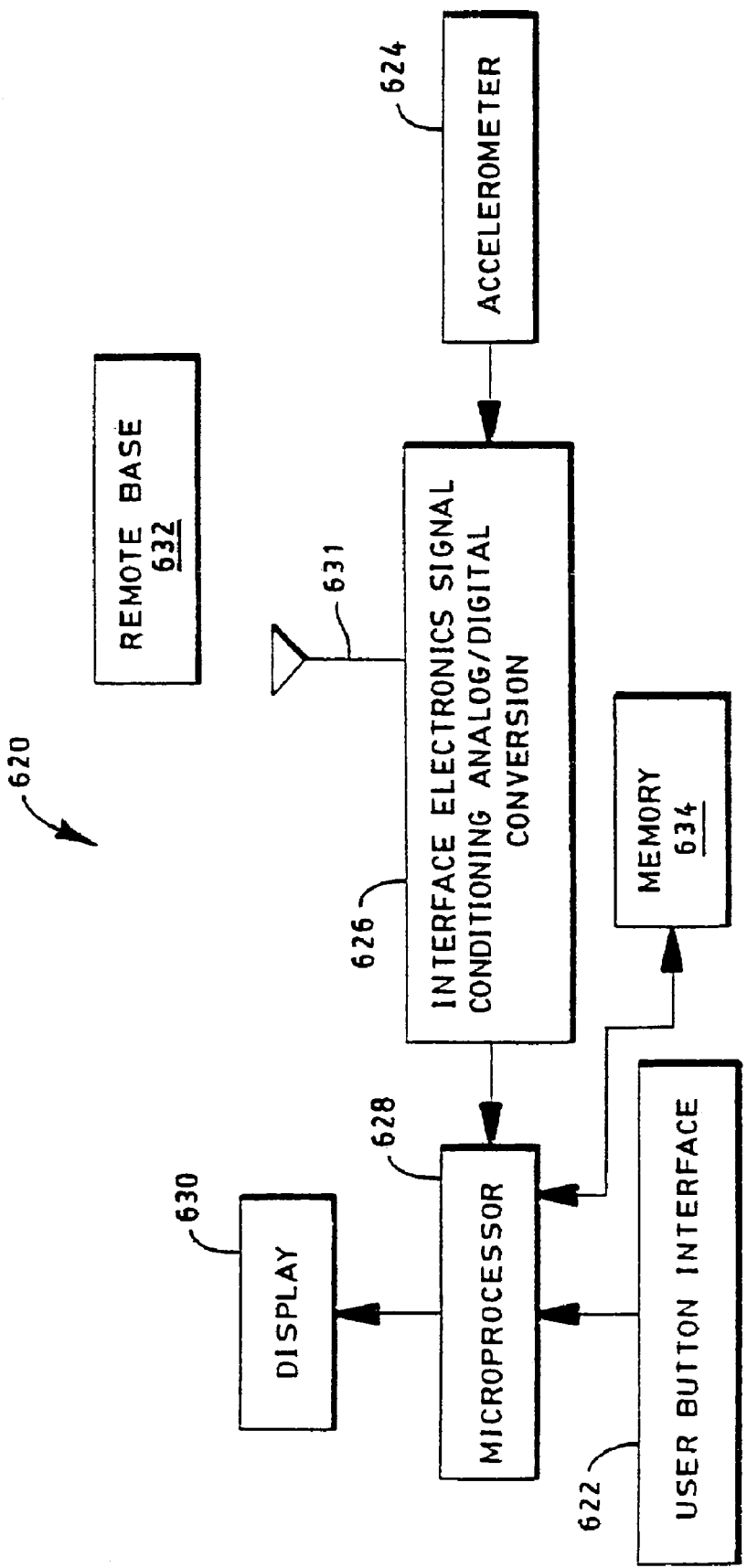
FIG. 21 schematically illustrates one system including a power sensing unit constructed according to the invention for measuring activity energy for various sportsmen.

One accelerometer-based vibration and shock measurement system (e.g., a power sensing unit) 620 of the invention is shown in FIG. 21. System 620 measures and processes accelerations associated with various impact sports and records the movement so that the user can determine how much shock and vibration was endured for the duration of the event. The duration is determined with a simple start stop button 622, although duration can alternatively start with an automatic recording that is based on the measured acceleration floor (or by an event such as triggered by the start gate 610, FIG. 20).

In system 620, vibrations and shock associated with skiing or exercise are measured by the use of an accelerometer 624 (or other motion or force-measuring device, e.g., a microphone or piezoelectric device) as the power sensor and of conditioning electronics 626 within the controller subsystem. The accelerometer 624 typically is AC-coupled so that low frequency accelerations, or the acceleration due to gravity, are ignored. The accelerometer output is then conditioned by passing the signal through a band pass filter within the electronics 626 to filter out the low frequency outputs, such as the varying alignment to the gravity vector, as well as the high frequency outputs due to electrical noise at a frequency outside the performance of the accelerometer 624. The resulting signal is one that has no DC component and that is bipolar such as the waveform shown in FIG. 22.

Figure 22:
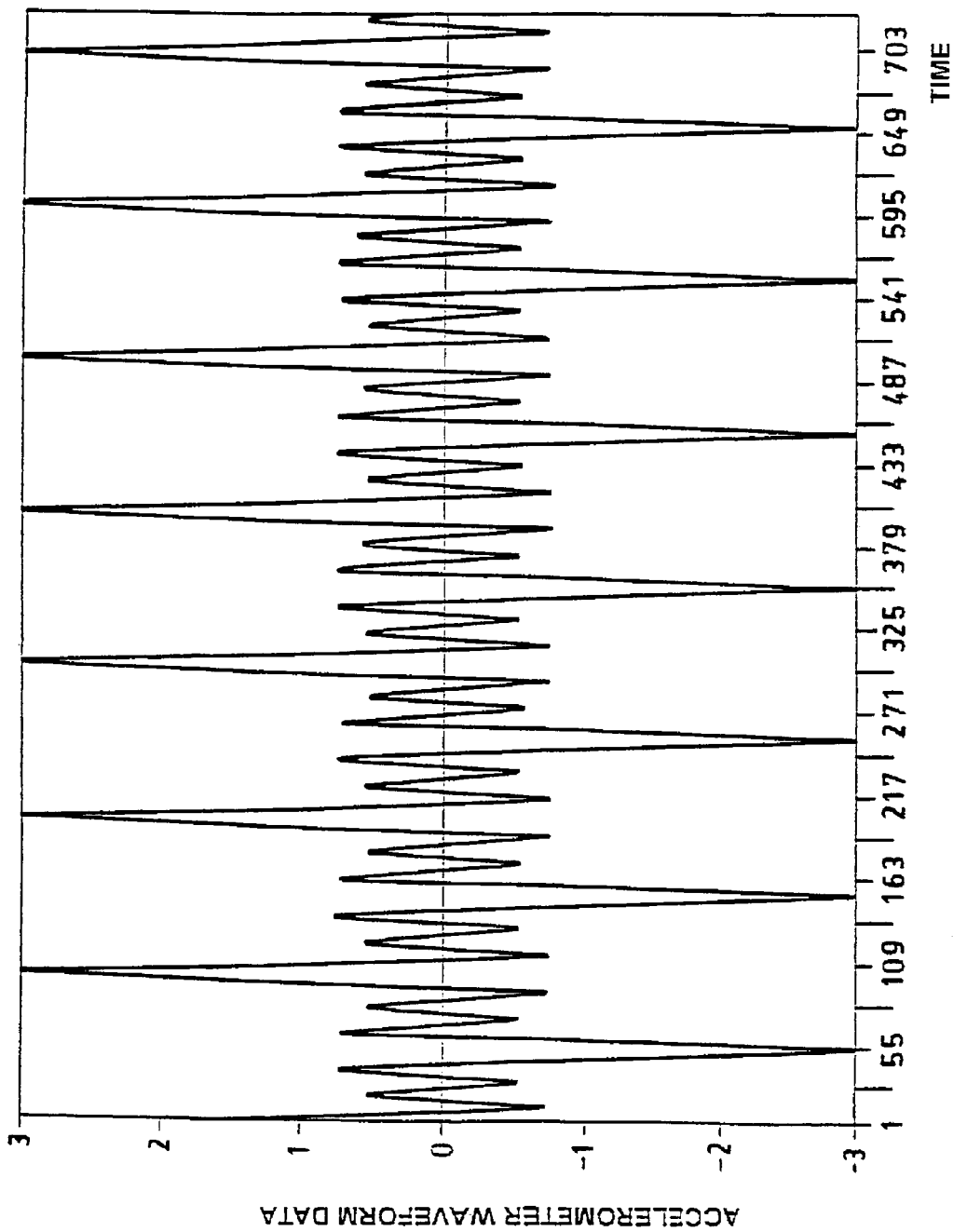
FIGS. 22-24 illustrate various, exemplary signals obtainable through the system of FIG. 21.

The system 620 thus conditions the signal and remove the negative components of the waveform in FIG. 22. This is done, for example, by rectifying the output of the bandpass signal. Since a positive acceleration is likely to be accompanied by a negative of the same area, the area of the positive may be doubled to obtain the area of the positive and negative. The signal may also be processed by an absolute value circuit. This can be done via an Operational Amplifier circuit such as the one shown in the *National Semiconductor Linear Applications Data Book Application Note AN*-31, which is herein incorporated by reference. In accord with certain processes, known to those skilled in the art, positive values become positive; and negative values become positive. By way of example, the waveform of FIG. 22 is processed, for example, to the waveform of FIG. 23.

Figure 23:
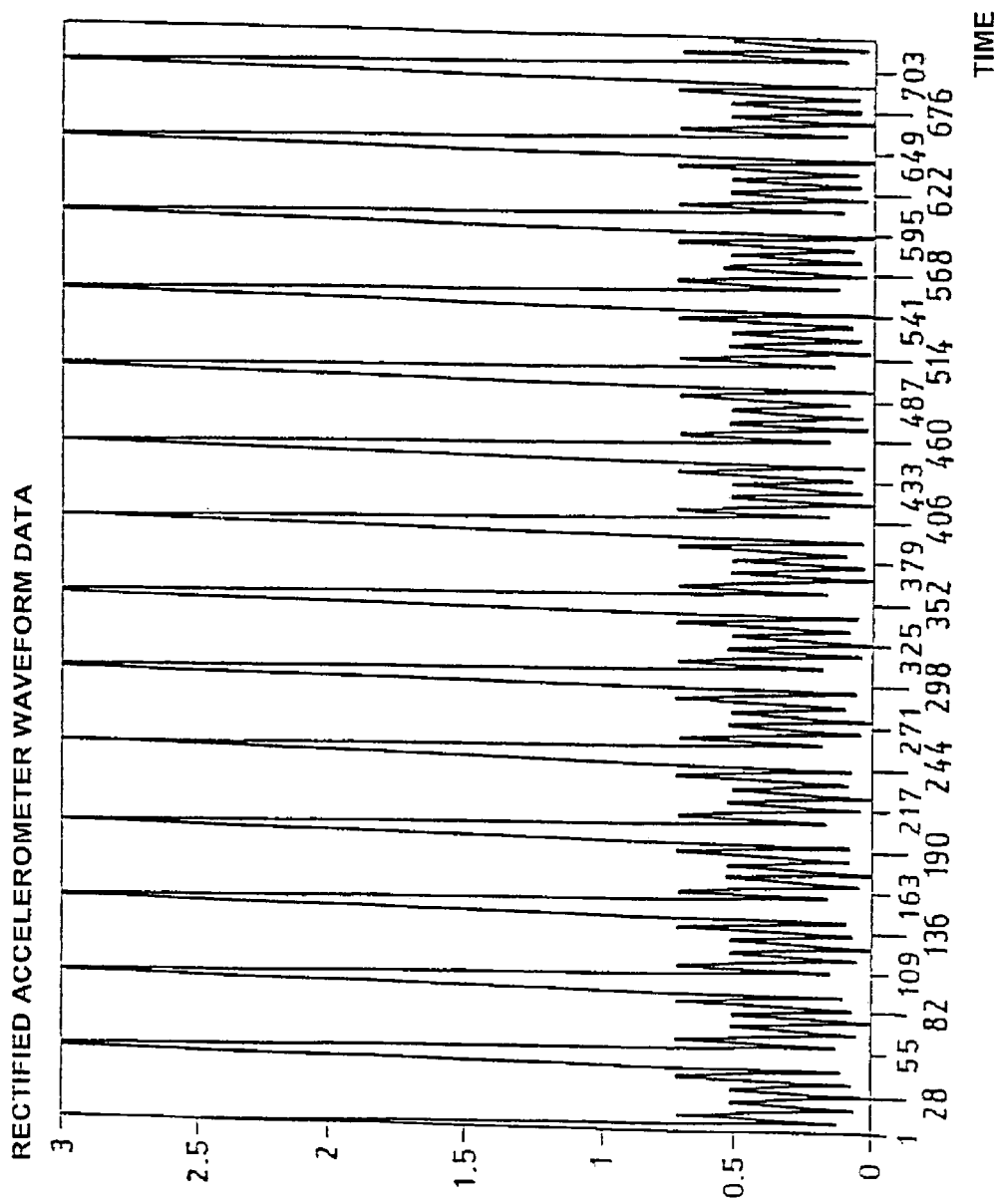
Figure 24:
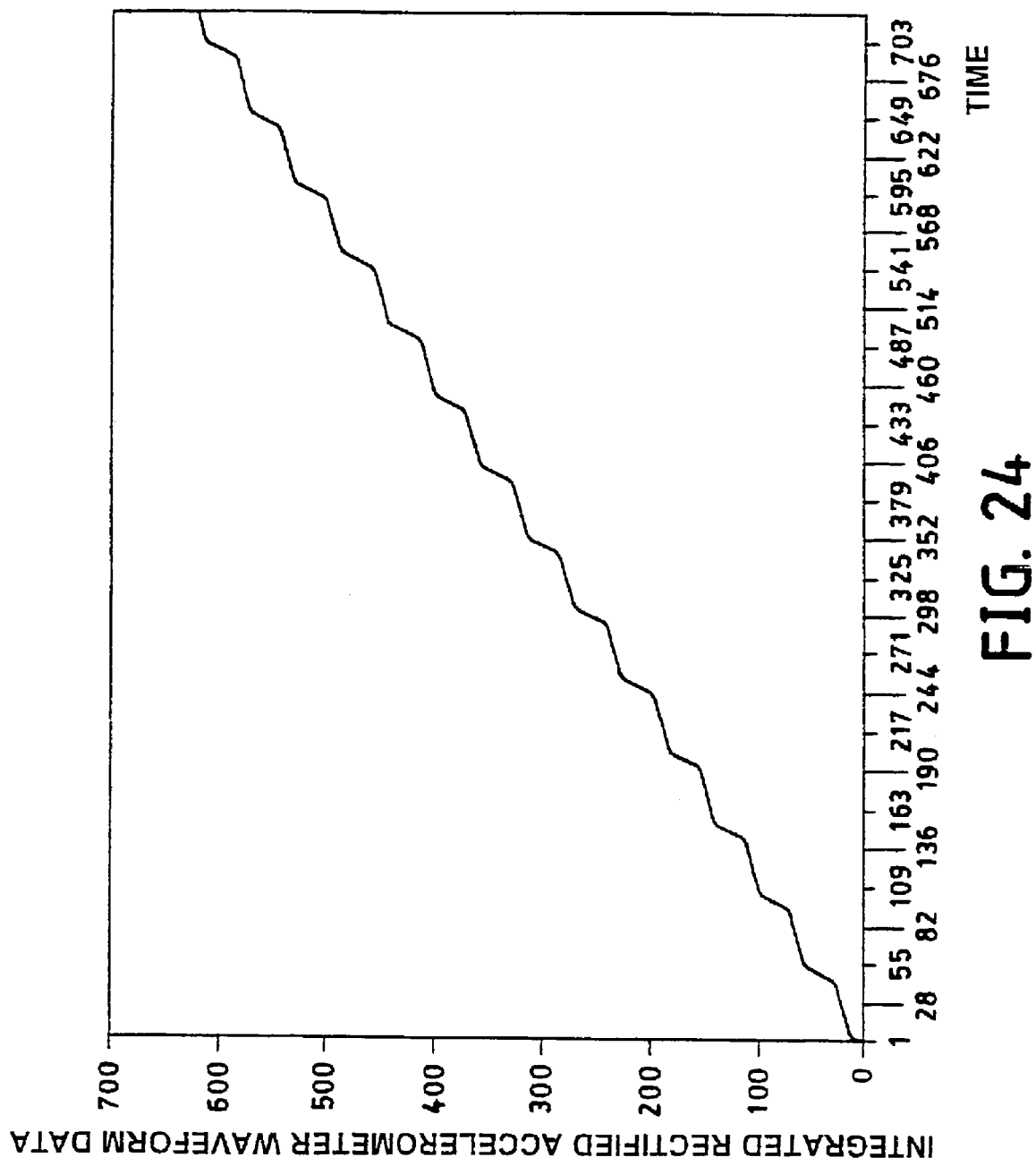

A unipolar waveform like the one shown in FIG. 23 is then integrated over time by the system 620 so that total acceleration is accumulated. This can also be averaged to determine average shock. The signal of FIG. 23 is therefore processed through an integrator (within the electronics 626 or the microprocessor 628) which will result in the signal shown in FIG. 24. A power value can then be displayed to a user via the display 630 (e.g., such as the display 24c or 52, FIGS. 1A and 1B).

The period of integration may be a day or simply a single run down a slope; or it may be manually started and stopped at the beginning and end of a workout. The output is then fed into a logarithmic amplifier so that the dynamic range is compressed. The logarithmic amplifier can be provided within the microprocessor 628.

At any stage, the system 620 can be fed into an analog-to-digital converter (such as within the electronics 626) where signal processing is done digitally. The output of the accelerometer 624 should anyway pass through an anti-aliasing filter before being read by a microprocessor 628. This filter is a low pass filter that ensures the highest frequency component in the waveform is less than half the sampling rate as determined by the Nyquist criteria.

The accelerometer 624 output can also be processed through an RMS circuit. The Root Mean Square acceleration is then determined from the following formula:

$$A_{RMS} \approx \frac{1}{T} \left[ \int_0^T A^2(t) \partial t \right]^{\frac{1}{2}}$$

where T is the period of the measurement and A(t) is the instantaneous accelerometer output at any time t. The period T may be varied by the user (i.e., to control the power period) and the output is a staircase where each staircase is of width T. This is then peak-detected and the highest RMS acceleration is stored; and an average acceleration and a histogram are stored showing a distribution of RMS accelerations. These histograms are displayed on a Liquid Crystal graphical display 630, for example, as a bargraph.

An alternate embodiment is to record the signal in time and transform the signal to the frequency domain by performing a Fourier transformation of the data (such as within the electronics 626 or the microprocessor 628). The result is a distribution of the accelerations as a function of frequency which is then integrated to determine the total signal energy contained (preferably over a frequency range). The distribution is, again, plotted on the LCD display 630.

Data may also be acquired by the accelerometer and telemetered to the electronics 626 via an RF link 631 back to a remote base 632 for storage and processing (e.g., such as at the base station 70, FIG. 1B). This enables ski centers to rent the accelerometer system 620 which is then placed on a ski (or snowboard) to record a day of activity. A printout can also be provided to the renter at the end of the day.

A separate memory module or data storage device 634 can also be used to store a selected amount of time data which can be uploaded at the end of the day. The data can be uploaded itself via a Infrared link readily available off the shelf, as well as through a wire interface or through an RF link 631.

The system 620 is particularly useful in impact sports that include mountain biking, football, hockey, jogging and any aerobic activity, including volley-ball and tennis. Low impact aerobics have become an important tool in the quest for physical fitness while reducing damage to the joints, feet and skeletal frames of the exerciser. The system 620 can be integrated within a shoe and may thus be used by a jogger to evaluate different running shoes. Alternatively, when calibrated, the system 620 is useful to joggers who can gate it to serve as a pedometer. The addition of a capacitor sensor in the heel helps determine average weight. A sensor for skin resistivity may additionally be used to record pulse. The shoe can also record the state of aerobic health for the jogger which is of significant interest to a person involved in regular exercise. The system 620 can also be used to indicate the gracefulness of a dancer while they develop a particular dance routine. A football coach may place these systems 620 in the helmets of the players to record vibration and shock and use it as an indicator of effort, or in the "football blocking dummies" to quantify player effort.

In skiing, the system 620 has other uses since a skier glides down a mountain slope and encounters various obstructions to a smooth ride. Obstructions such as moguls cause the skier to bump and to induce shock. This shock can be measured by the accelerometer 624 and accumulated in a memory 634 to keep a record of how much shock was encountered on a particular ski run. Exercisers may use such a system 620 to grade their ability to avoid impact. A jogger may use the system 620 to evaluate their gate and determine their running efficiency. This becomes important with a greater emphasis being placed on low impact aerobics.

Those skilled in the art should appreciate that other improvements are possible and envisioned; and fall within the scope of the invention. For example, the system 620 mounted on a ski may be used to determine the total shock and vibration encountered by a skier traveling down a slope. Mounting an additional accelerometer 624 above the skier's hip allows an isolation measurement between upper torso and ski, as described above. This can be used to determine how well a trained skier becomes in navigating moguls. This measurement of the isolation is made by taking an average of the absolute value of the accelerations from both accelerometers 624. The ratio of the two accelerations is used as a figure of merit or the isolation index (i.e., the ratio between two measurements such as on the ski and the torso, indicating how well the mogul skier is skiing and isolating knee movement from torso movement).

To avoid the complications of gravity affecting the measurements of system 620, a high pass filter should be placed on the accelerometer output or within the digital processor sampling of the output. All analog signals should have anti-aliasing filters on their outputs whose bandwidth is half the sampling frequency. Data from the accelerometers 624 is preferably sampled continuously while the circuits are enabled. The processor 628 may determine that a ski run has started by a rise in the acceleration noise floor above a preset trigger and at a set duration. In another embodiment, a table is generated within the processor of each sufficiently high acceleration recorded from the ski. The corresponding upper torso measurement may also be recorded along with the ratio of the two measurements. The user can additionally display the n-bumpiest measurements taken from the skis and display the isolation index.

Figure 25:
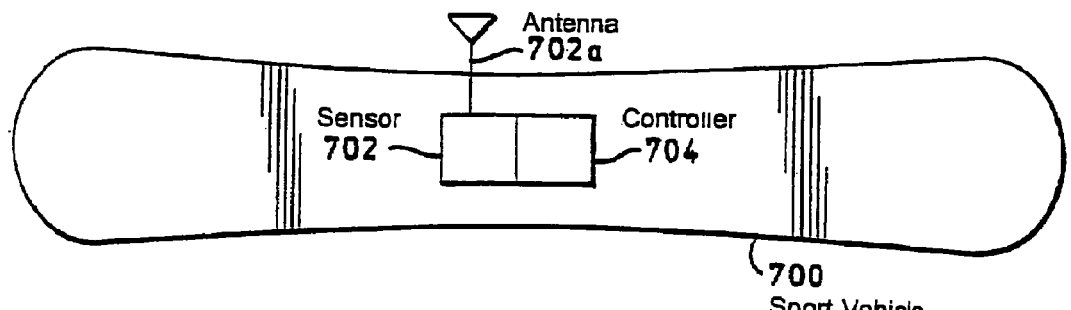
FIG. 25 illustrates an alternative airtime, speed and/or drop distance measuring system, according to the invention, utilizing a GPS receiver.

FIG. 25 shows a sport vehicle 700 (here shown as a snowboard) mounted with a GPS sensor 702 (and antenna 702*a*) that is coupled to a controller subsystem 704 such as described herein. The GPS sensor 702 serves the functions of one or more of the sensors 14, FIG. 1A. As known in the art, GPS receivers such as the sensor 702 provide absolute position in terms of altitude and earth location. By monitoring the signal from the GPS sensor 702, speed, height and loft time are directly determined. For example, at each signal measurement, a difference is calculated to determine movement of the vehicle 700; and that difference is integrated to determine absolute height off of the ground, distance traveled, speed (i.e., the distance traveled per sample period), and airtime. FIG. 25 thus illustrates a sensing unit which includes a GPS sensor 702 (operating as one or more of airtime, speed and drop distance sensors) and a controller subsystem 704, such as the subsystem 12 of FIG. 1A.

Figure 47:
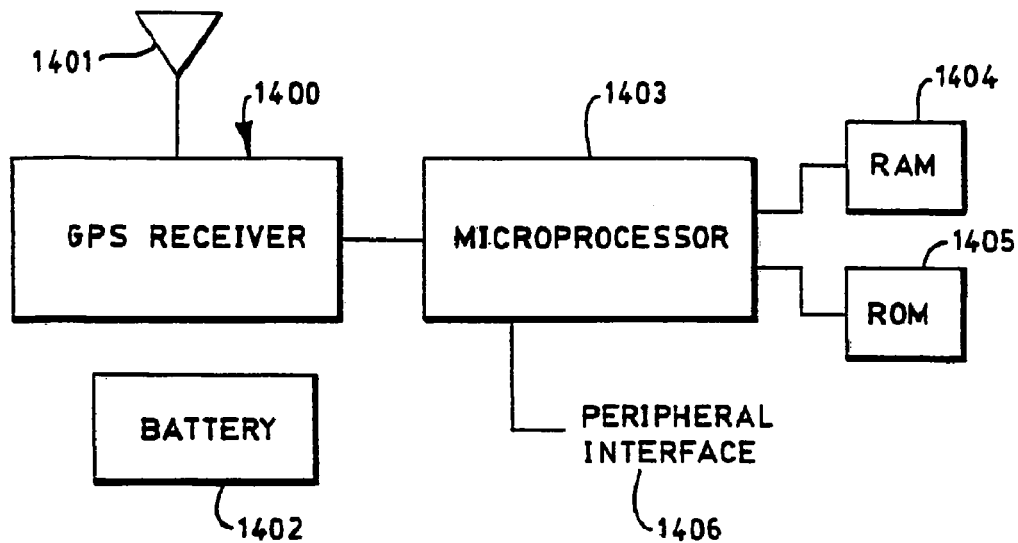
FIG. 47 illustrates a GPS-based system of the invention.

FIG. 47 illustrates one GPS-based system of the invention, including a GPS receiver 1400 with an antenna 1401. The antenna is small because GPS operates at an extremely high frequency. The antenna 1401 may be mounted with a back-back, of the user, containing the GPS receiver. The receiver is powered by a battery back 1402 which also powers a microprocessor 1403. The microprocessor 1403 takes data from the GPS receiver 1400 and stores it as a position in random access memory RAM 1404. The data is preprocessed according to a program stored in Read Only Memory ROM 1405. The processor ROM 1405 can also contain stored maps with which to determine skier performance, allowing the program to become an expert system to, for example, identify trail features or problems. The user interfaces with the microprocessor 1403 via the peripheral interface 1406. Examples of a peripheral interface include keyboards, displays, etc. A panic button can be included with the interface 1406 to inform a base station of trouble. The warning is sent with exact location so that the rescue team (e.g., the ski patrol) can easily find the stricken person (e.g., skier).

An enhancement to the above system utilizes differential GPS. Differential GPS makes use of the property that a fixed receiver in a known position can be used in conjunction with a non-stationary GPS receiver with the effect that many of the large errors are rejected. The result is a more accurate position solution for the moving receiver. In the preferred embodiment, a user carries the receiver 1400 and the base station houses the differential model, as known in the art.

For skiing and other similar sports, the user is given a GPS receiver and an RF link (e.g., a transmit section 22 of FIG. 1A) so that a central computer at the base station lodge (e.g., station 70, FIG. 1B) knows the location of every user. Such locations may then be broadcast to the skier for display in a set of goggles using a heads-up display.

Figure 26:
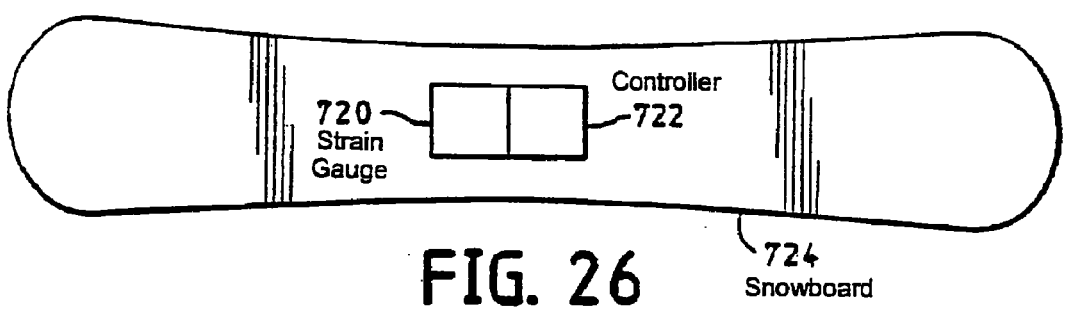
FIG. 26 schematically shows one airtime and/or power sensing unit of the invention, mounted to a snowboard.

FIG. 26 shows a strain gauge 720 connected to a controller subsystem 722, such as the subsystem 12 of FIG. 1A. In the illustrated embodiment, the sport vehicle is a ski or snowboard 724. Those skilled in the art understand that strain gauges can detect stress associated with the surface that the gauge is mounted upon. The gauge 720 thus senses when there is little or no stress on the snowboard 724, such as when the snowboard 724 is in the "air"; and the subsystem 722 then determines airtime from that relatively quiescent period. FIG. 26 thus illustrates a sensing unit which includes a strain gauge 720 as an airtime sensor and a controller subsystem 722. The sensing unit 720/722 can further provide factors such as power, by utilizing the signal generated by the strain gauge 720 as a measure of the punishment that the user applies to the vehicle 724. Accordingly, the gauge 720 can operate as a power sensor in addition to an airtime sensor.

In an alternative embodiment, the element 720 is a temperature gauge that senses the change in temperature when the ski 724 leaves the ground. This change of temperature is monitored for duration until it again returns to "in contact" temperature. This duration is then equated to "airtime" or some calibrated equivalent (due to thermal impedance). Note that the impedance of air is different from snow; and hence that change can also be measured to determine airtime.

In an alternative embodiment, the element 720 is a load cell, known in the art, such as a strain gauge bridge, or other force-sensing means, such as force sensing resistors (FSRs). A unit incorporating such elements operates as described above.

Figure 27:
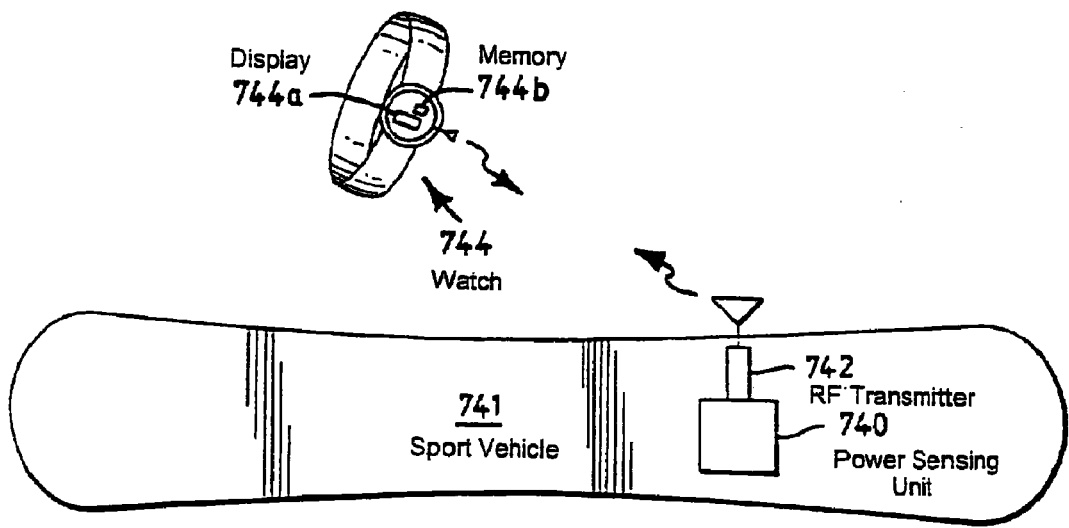
FIG. 27 schematically illustrates a performance system utilizing a data unit in the form of a watch.

FIG. 27 shows one speed, airtime and power sensing unit 740, constructed according to the teachings herein, and mounted to a sporting vehicle such as the ski 741. The unit 740 has an RF transmitter 742 (e.g., similar to section 22, FIG. 1A) to communicate signals from the unit 740 to a watch 744 worn by the user (not shown). In this manner, the user can look at the watch 744 (nearly during some sporting activities) to monitor performance data in near-real time. A small watch display 744*a* and internal memory 744*b* provide both display and storage for future review.

The devices for measuring speed, airtime, drop distance and power as described herein can oftentimes be placed within another component such as a user's watch or a ski pole. For example, the power system 620 of FIG. 21 is readily placed within a watch such as watch 744, and without the unit 740, since power integration can be done from almost anywhere connected to the moving user. Likewise, airtime measurement through the absence of a spectrum, such as shown in FIG. 6, can also be done in a watch or a ski pole. Speed measurements, however, are much more difficult if not impossible to do at these locations because of the lack of certainty of the direction of movement. However, with the increased performance and size reductions of guidance systems with accelerometers (see FIGS. 9 and 10), even this can be done.

Figure 28:
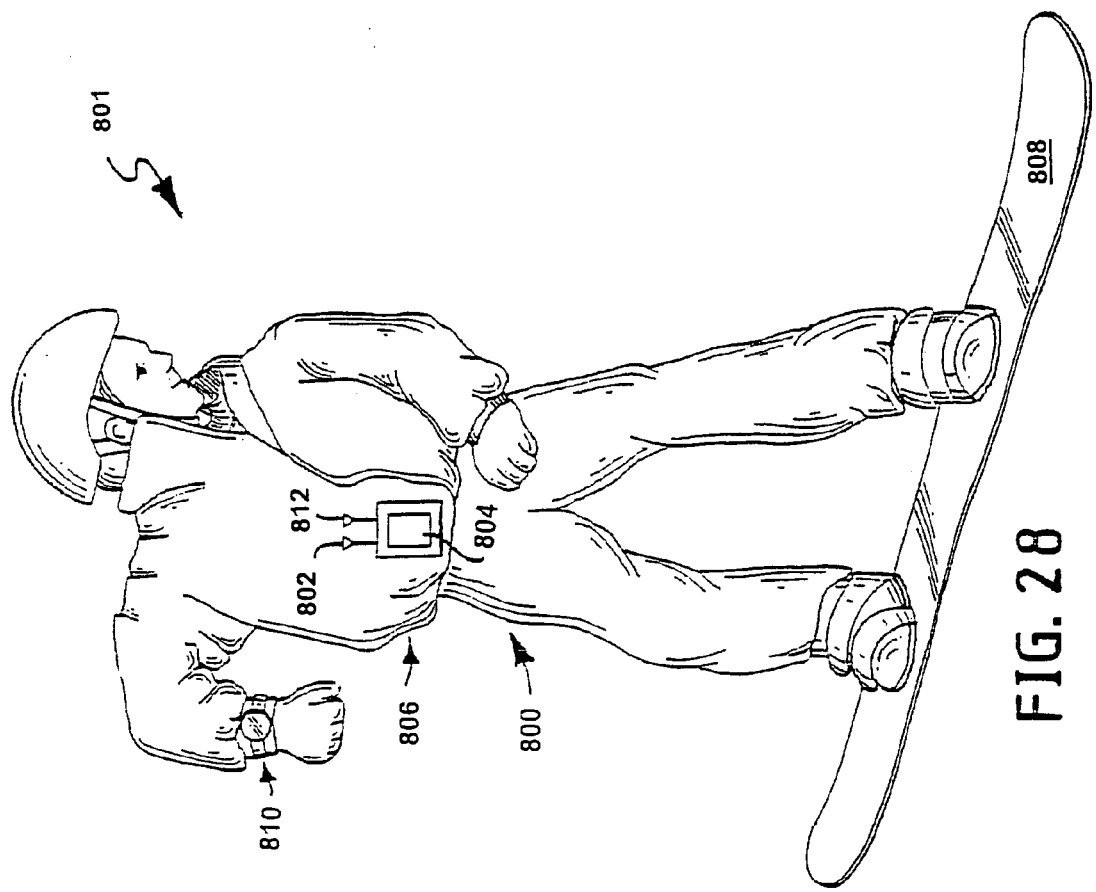
FIG. 28 illustrates a GPS-based drop distance sensing unit of the invention.

FIG. 28 illustrates one drop distance sensing unit 800 for determining drop distance from a skier or snowboarder 801 (or other sport enthusiast, e.g., a mountain biker, skateboarder, roller-blader, etc.). The unit 800 includes an antenna 802 and a GPS receiver 804. The GPS receiver operates such as known in the art. Although the unit 800 is shown on the skier's waist 806, the unit 800 can also be coupled to the snowboard 808 or it can be constructed integrally with the user's watch 810. In the embodiment shown, the unit 800 can include a second antenna 812 (or other data transfer mechanism, including IR techniques) which communicates with the watch 810 so as to send performance data thereto.

Figure 29:
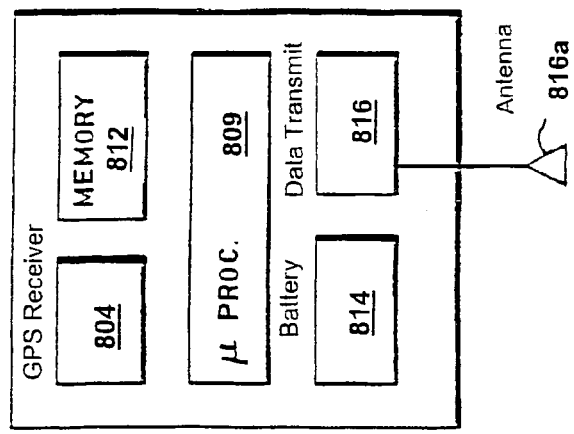
FIG. 29 shows further detail of the unit of FIG. 28.

FIG. 29 illustrates a block diagram of the drop distance sensing unit 800, including further detail therein. A microprocessor 809 connects with the GPS receiver 804 to process GPS data. In particular, the GPS data is known to include three dimensional data including height off the earth's surface. The processor 809 thus processes the data at predetermined intervals, e.g., about 1 second or less, to determine the change of height from the last measurement. Accordingly, when airtime is determined, according to the teachings herein, the device 800 also determines drop distance for that interval. The drop distance information is stored in internal memory 812 so that it can be retrieved by the user or transmitted to a data unit such as the watch 810. Records of drop distance can also be stored within the memory 812 such that a peak drop distance and a series of drop distances can be stored and retrieved by the user at a later time. The device 800 also includes a battery 814 and other interconnections and processing electronics (not shown) to operate the device 800 and to provide drop distance data, as described in connection with FIGS. 1A and 1B. A data transmit section 816 (e.g., the section 22, FIG. 1A) transmits data via an antenna 816*a* (or other technique), as desired, to the watch 810 or to other displays or data units, or to the base station, such as discussed herein.

Evaluation System

The sensing units described herein can be complex, and require lengthy evaluation to provide a robust system. To evaluate such units, a data evaluation system was developed, as described next. The data evaluation system provides a flexible data recording unit that has applicability in several circumstances where large amounts of data are collected in adverse and remote environments.

Figure 30:
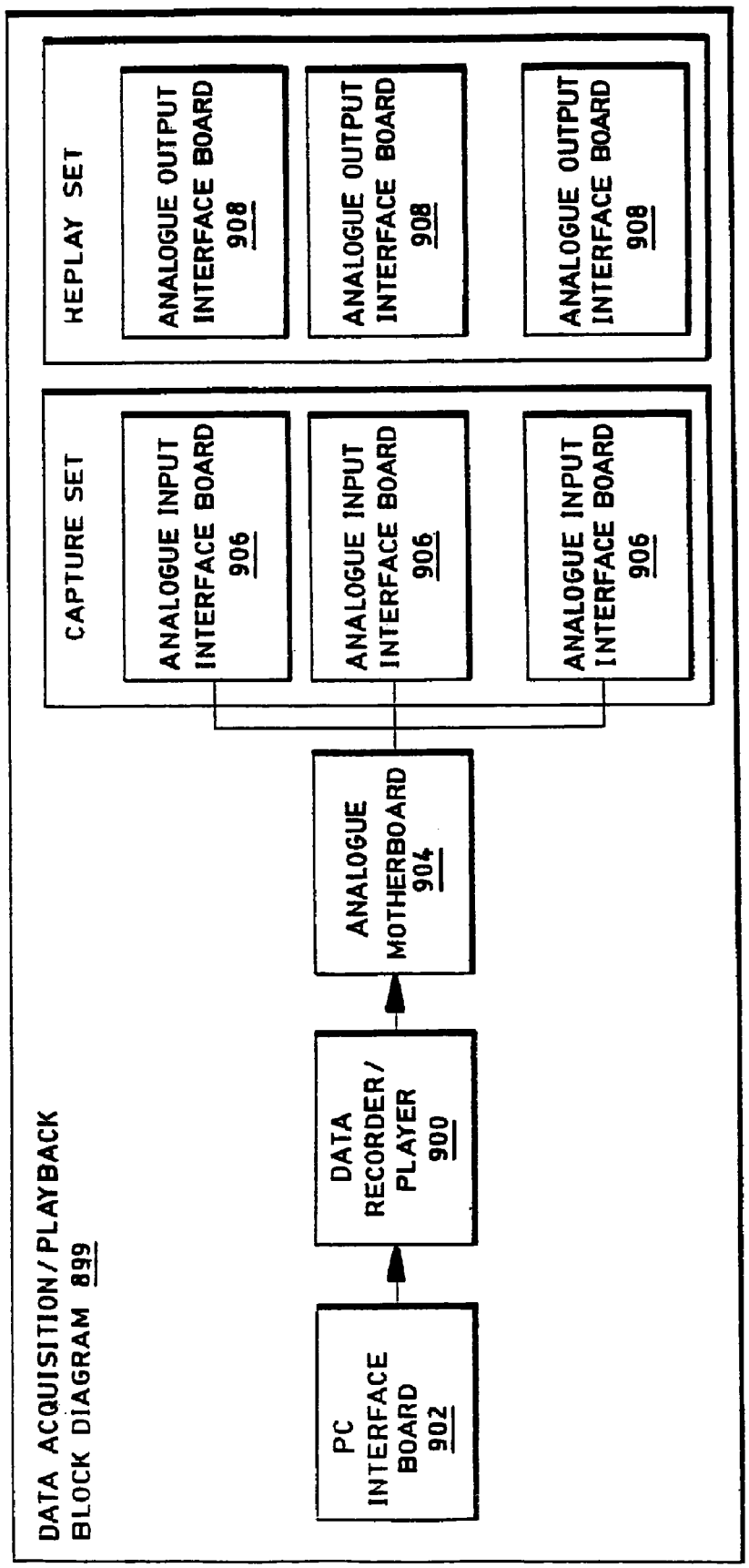
FIGS. 30-33, 34A, 34B and 35 illustrate data collection hardware used to reliably collect large quantities of sensor data at a remote and environmentally difficult location, in accord with the invention.

As shown in FIG. 30, the Data Acquisition system 899 includes five main components on a data acquisition/playback board:

Data Recorder/Player 900

PC Interface 902

Analogue Motherboard 904

Analogue Input Interface Boards 906

Analogue Output Interface Boards 908

To record information, the Data Recorder/Player board and Analogue Mother Board 900, populated with the required Analogue Input Interface Boards, are placed in a box, connected by a small back plane. Once the data has been recorded, the Data Recorder/Playback Board 900 is removed from the box, and connected to the PC Interface board. The PC then controls the downloading of data to file.

The overall size of the Recording Package is 2½" wide, 5½" deep, and 4½" tall. All sensors are external, and may or may not be housed in boxes.

Figure 31:
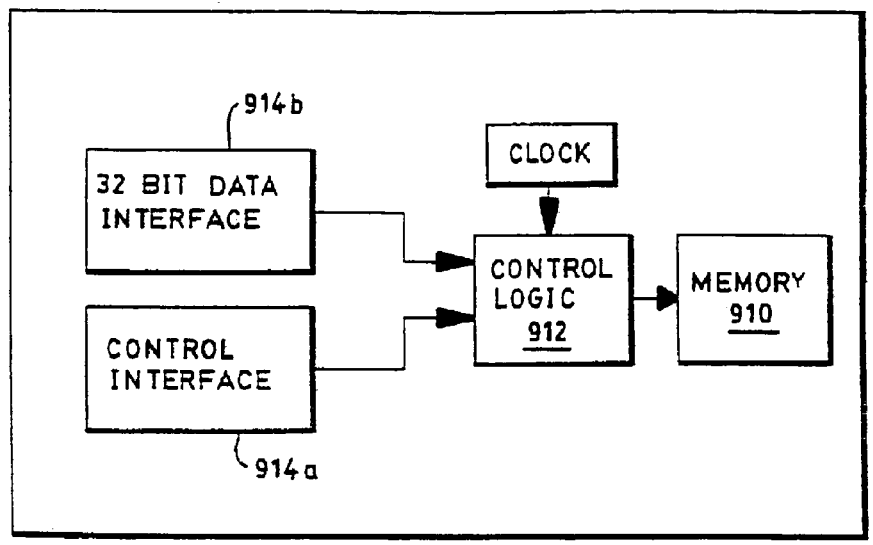

The data recorder and player 900, FIG. 31, is the heart of the system 899. It includes a block of memory 910 for holding the sampled data values, controlling logic 912, and interfaces 914*a*, 914*b*.

The Data Recorder/Player Board (DRPB) 900 always handles 32 bits of data. It is configured to either Record or Playback the data at a rate of one word (32 bits) every 15.6 μS (approx. 64 KHz). The control interface 914 provides signal to interface to the PC Interface board and Analogue Mother Board.

The Control Logic 912 also provides refresh cycles for the dynamic RAMs. The Memory 910 consists of any 72-pin SIMM modules. These must be matched in the same manner as when used in a PC. (i.e. one 8 Mb cannot be mixed with one 16 Mb module.) This provides a limit of 512 Mb of RAM, which will give a maximum of 134217728 samples. This is equivalent to 34 minutes and 53 seconds. However, the larger SIMM's are physically taller than standard-sized devices and are very expensive. In practical terms, two 64 Mb SIMMs (128 Mb) provide 8 minutes and 43 seconds of data recording at 64 KHz.

The recorder can be paused during testing. Longer recording periods make annotation of the data (and data handling) more difficult. If this limit is acceptable, two of the SIMMs can be removed from their sockets in the DRPB 900, to reduce its size.

The DRPB 900 has its own NiCAD battery (attached to the board for safety) such that the board can be removed from the box on the ski and taken to the PC for downloading.

PC Interface

The PC Interface 902 allows the DRPB 900 to be connected to the parallel port of a PC. It requires a bi-directional port (EPP). The design uses two MACH 210s, and allows the PC to control the upload and download process completely. The current download/upload rate achieved is 8 Mbytes/minute which is generally acceptable.

Analogue Mother Board

The Analogue Mother Board (AMB) 904 controls the sampling of the data on the Analogue Input Interface boards (AIIBs) 906. It presents the Data Recorder/Player 900 with 32 bits of data for each recording period. Data from the AIIBs 906 are multiplexed. The programming of the AMB 904 determines the sampling rates and position of the data in the 32-bit word for the AIIBs 906. If a different combination of AIIBs is required, the AMB 904 is reprogrammed. Therefore, the control logic on the AMB 904 is held in an AMD MACH 211 which is a flash device, programmable whilst still on the board using a JTAG connector (thus a notebook PC with a parallel port can reconfigure the board.)

Figure 32:
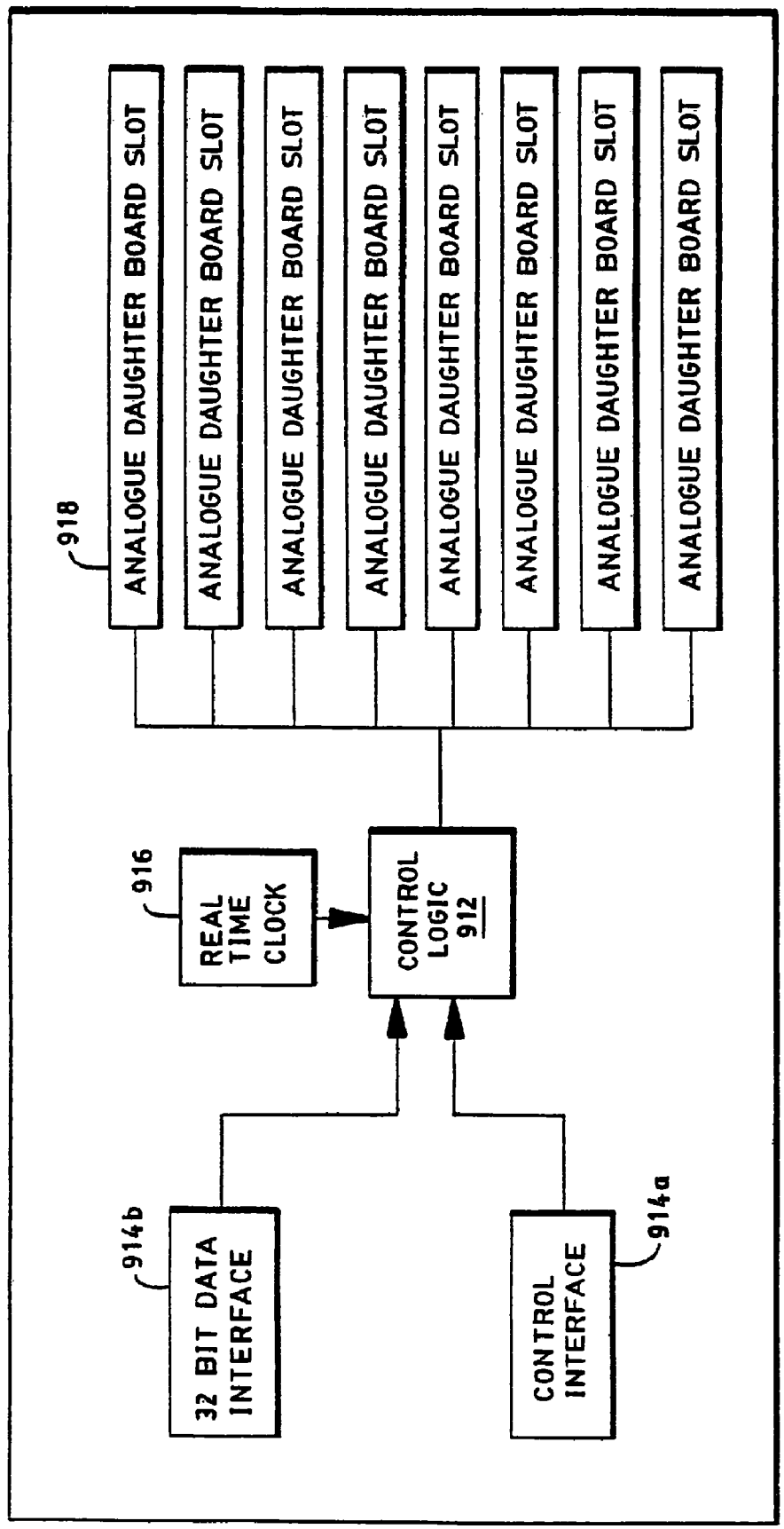

As shown in FIG. 32, the Control Logic 912 inserts the real time clock 916 value into one channel (probably an 8 KHz channel). This will simply be a counter counting at a minimum frequency of 8 KHz, which allows the analyzing software to detect when the recording was paused.

Analogue Input Interface Boards

The Analogue Input Interface boards 906 are small daughter boards which plug in vertically to the Analogue Mother Board 904 (i.e., into the slots 918, FIG. 32). The Mother board 904 will allow 8 of these boards to be connected at once. This design allows an interface board to suit the signal to be recorded. This is then combined with other interface boards to allow recording of a combination of signals, as required.

Figure 33:
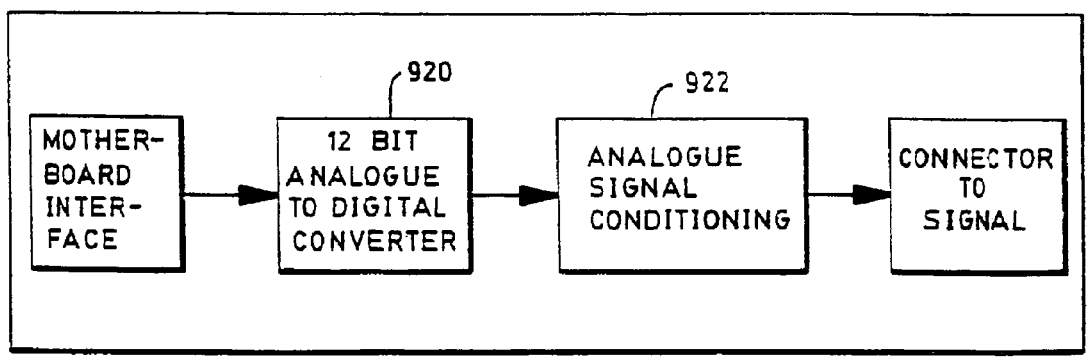
Figure 34A:
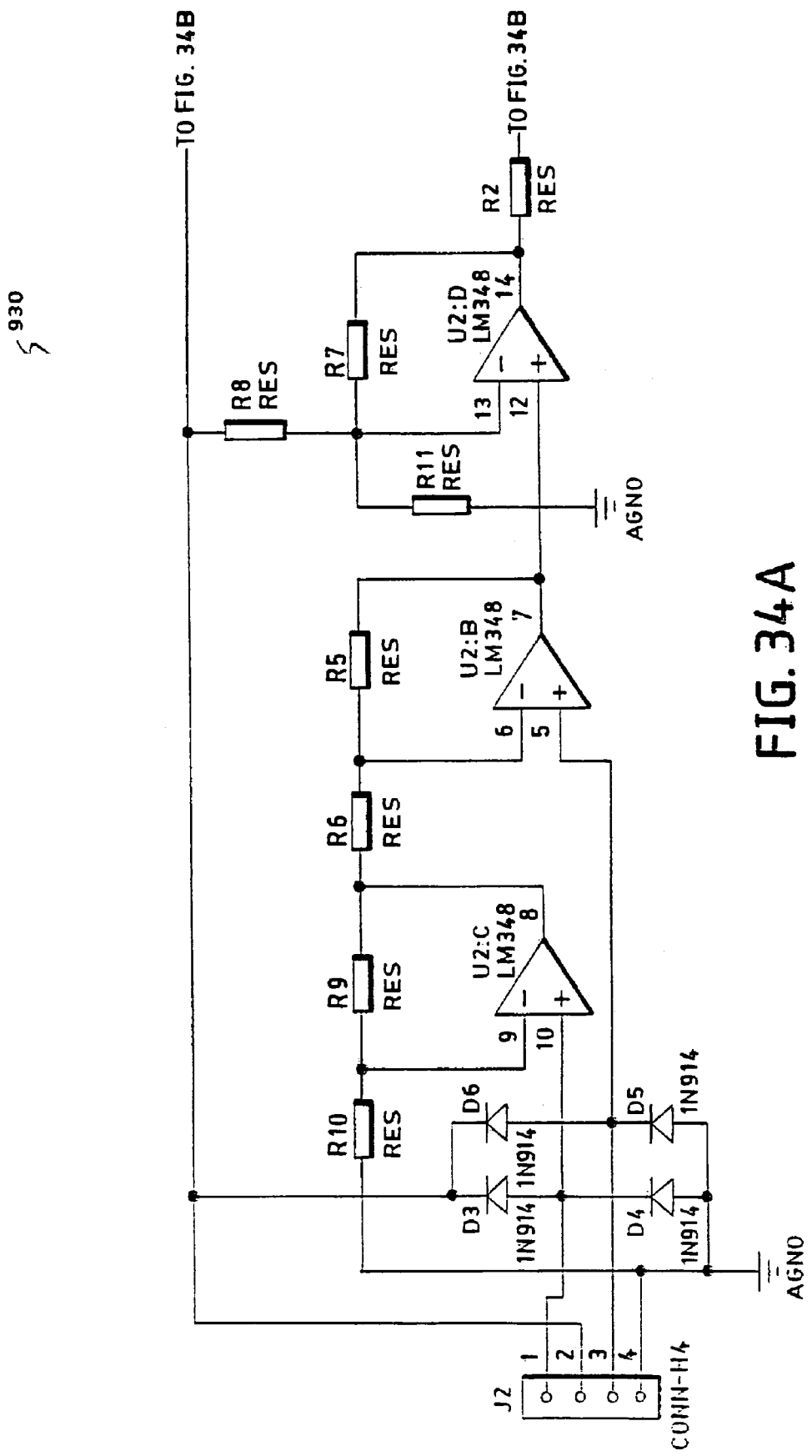
Figure 34B:
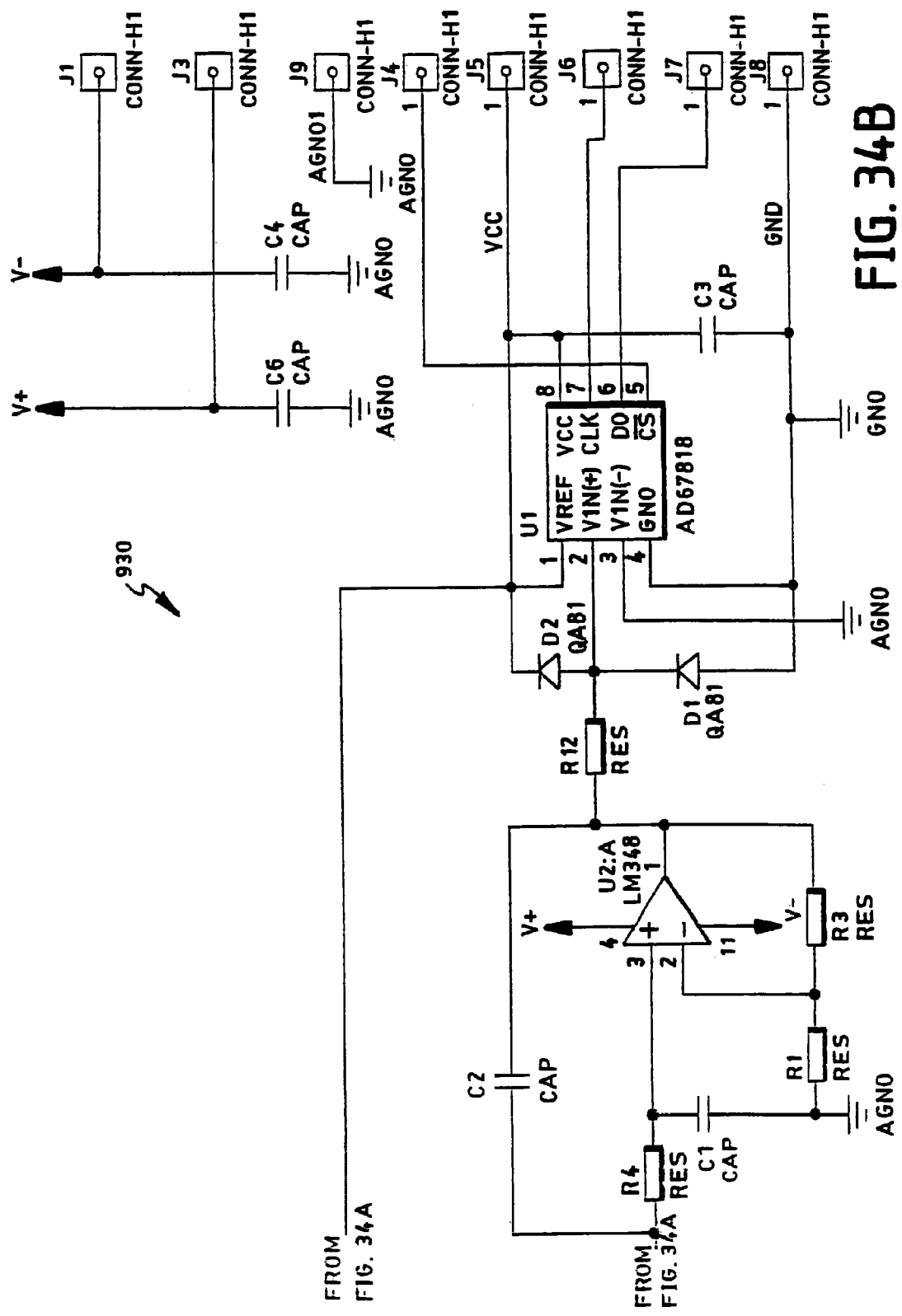

As shown in FIG. 33, the A/D converter 920 is a serial device; thus reducing the number of pins required and the level of board complexity. The board space available for Analogue Signal Conditioning 922 is limited. The Pressure Sensor AIIB 906 (i.e., that board incorporating a drop distance sensor, discussed above), shown schematically in FIGS. 34A and 34B, provides an example of the size limitations, and the complexity level limitations on the circuitry. Specifically, the circuit 930 of FIGS. 34A and 34B is an example of an AIIB 906 for a SenSym Pressure sensor. It uses four op-amps and various capacitors and resistors to provide the required signal conditioning.

Figure 35:
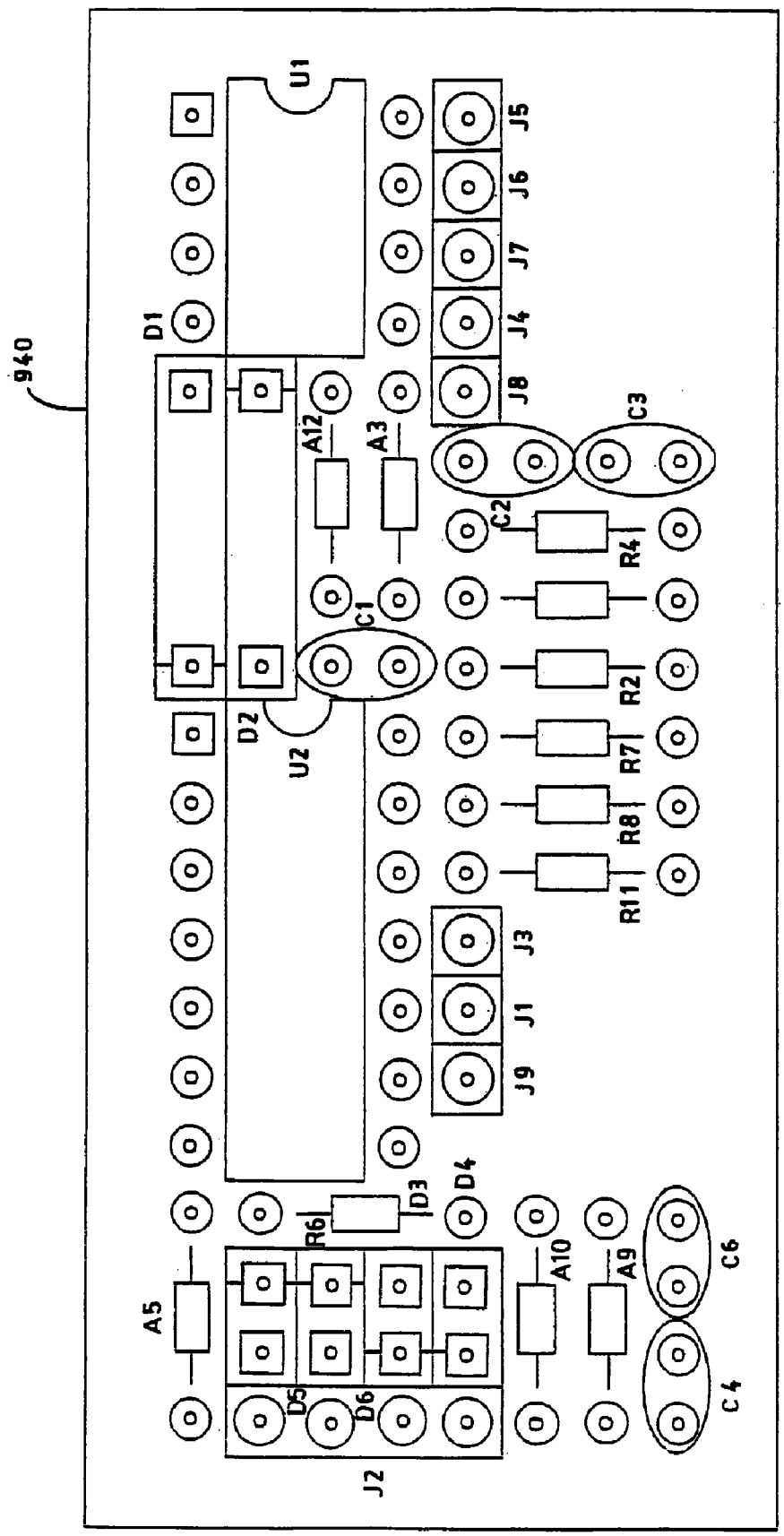

FIG. 35 exemplifies a layout board 940 for circuit 930, FIGS. 34A and 34B, used to connect to the AMB 904. The height of the board 940 is 0.9", and the width is approximately 2½ inches.

Preferably, one AIIB 906 incorporates a Voice Annotation Channel, so that data can be annotated by voice concurrently with data acquisition. The AIIB 906 for the Voice annotation channel can have a simple tone generator connected to an external button that is operated by the skier. This will inject a tone when pressed onto the voice channel to allow marking in the annotation of special places.

The analog interface boards 908 are similar to the AIIBs, but have a DAC rather than ADC components. They allow the system to generate signals as recorded from the sensors. Thus a new board design can be tested on a virtual slope on the bench.

The data acquisition system thus permits the capture of data, real time, to evaluate sensors such as altimeters used in a drop distance sensor, described herein. Two exemplary altimeters, for example, are the SenSym SCX15AN Pressure sensor and the SenSym SCX30AN Pressure sensor.

As discussed herein, many embodiments of the invention utilize piezo foils, such as within airtime, power, and speed sensors. These foils for example include those foils from AMP Sensors, such as the AMP DT0-028K foil or the AMP LDT1-028K foil. Similarly, an accelerometer like the AMP ACH-01-03 accelerometer can be used to generate vibration data (this sensor was in fact used to collect the data of FIG. 6).

Figure 36:
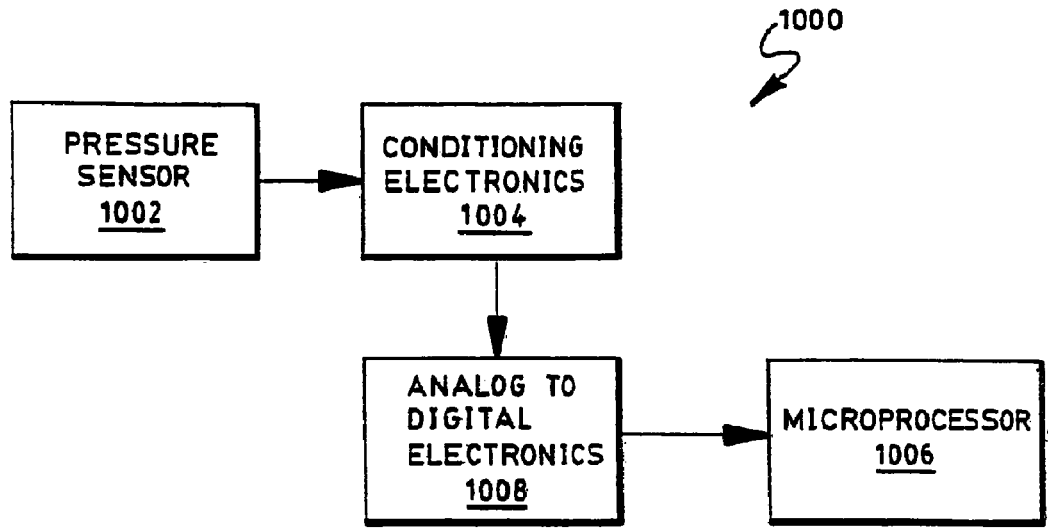
FIG. 36 shows a schematic view of a pressure-based drop distance sensing unit of the invention.

Another pressure-based drop distance sensing unit 1000 of the invention is shown in the block diagram of FIG. 36. The unit 1000 includes a pressure sensor 1002, as described above, and is used to determine altitude. GPS, as described above, may also be used in connection with the unit 1000. The pressure sensor altimeter 1002 is used to determine ambient pressure. As altitude changes, so does the pressure. The pressure sensor 1002 indicates pressure by an analog voltage. That voltage is conditioned by the conditioning electronics 1004 so that the output data is filtered, well-behaved and has an appropriate scale factor. The electronics 1004 also typically filter the signal to prevent aliasing when sampled by the controller subsystem 1006. After conditioning, the data is converted to a digital word by A/D electronics 1008 for the microprocessor 1006. The data is thus represented as an eight, twelve or sixteen bit word. It is then read by the microprocessor 1006 and is interpreted as altitude.

Figure 37:
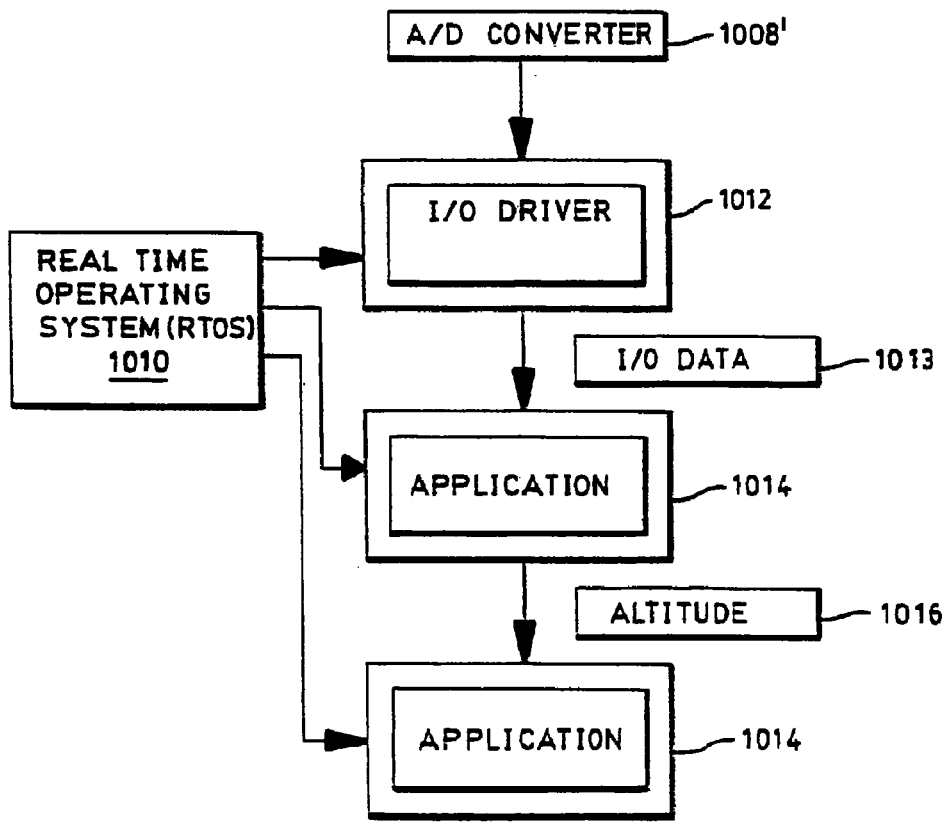
FIG. 37 illustrates further processing detail of the unit of FIG. 36.

As illustrated in FIG. 37, the processor 1006 includes resident software that schedules the reading of data and its manipulation thereof. The core shell of software is the Real Time Operating System 1010. This may be purchased off the shelf by companies such as Ready Systems. These programs process tasks according to user selected priorities so that every task is executed within a software control frame. The part of the software that reads the pressure sensor output (from the A/D 1008') is called the Input Output Driver or I/O Driver 1012. This program may be executed on a regular basis automatically or may be the result of an interrupt. In the event of an Interrupt, the processor 1006 automatically launches an interrupt service routine or ISR. The purpose of an ISR and I/O Driver 1012 is to get the data into the processor's memory so that an application program may use the information. Filtered by the I/O Data 1013, the application 1014 is the software that interprets the data, such as to determine altitude 1016. The data may then be stored in memory for other applications 1014 to operate on the data, use it for decision making, or pass it on to other I/O Drivers for output.

The processing of altimeter data from the pressure sensor 1002 is a matter of eliminating the low and high frequency noise from the measurement. In this embodiment, this is done by cascading a high pass with a low pass filter. The Low pass filter is selected by determining the sampling rate and ensuring that the highest frequency component in the signal passed through the filter is half the sampling rate, known as the Nyquist criteria. Frequencies that are higher than half the sampling rate will result in aliasing. This means that the spectrum will be distorted and the original signal is not accurately reconstructed.

The high frequency component of the cascaded high pass, low pass filter is thus selected by the maximum rate of descent the skier will travel. The higher the low pass filter, the faster the altimeter tracks the skier. Since the skier is limited by inertia and kinematics (the basic laws of motion) the rate of altimeter change is not high by signal processing standards. If a skier travels at 100 ft per second, this is about 68 miles per hour, which means that if they move along true vertical their altitude would be changing at 100 ft/sec. If the change in output voltage goes from DC to 100 Hz, then the low pass filter also needs to pass the 100 Hz.

The low frequency of the high pass, low pass filter is related to how slow the signal changes. In this case it is limited by the frequency response of the altimeter and the slow changes associated with atmospheric fluxuations.

Figure 38:
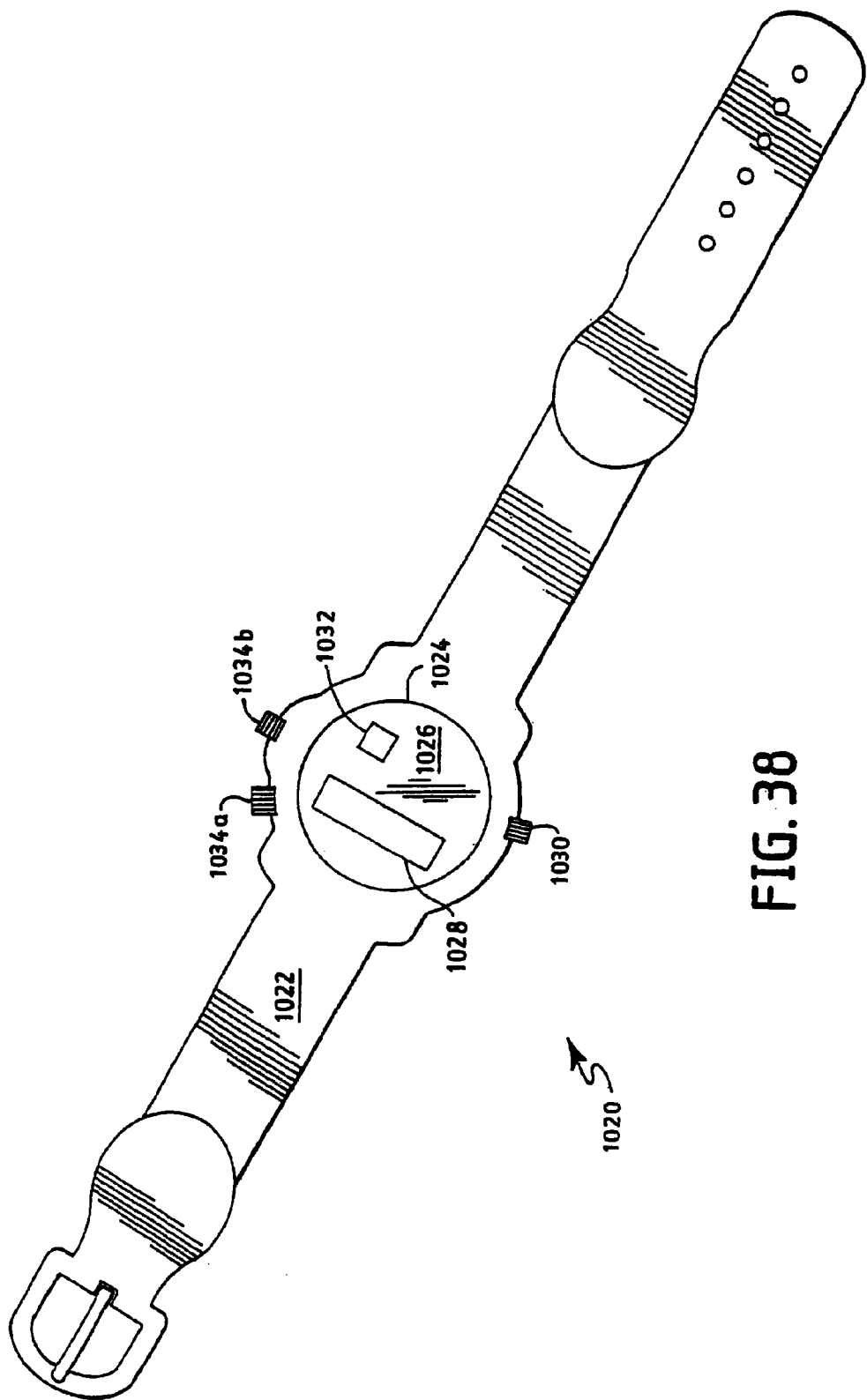
FIG. 38 illustrates a power watch constructed according to the invention.

FIG. 38 shows a "shock" or "G" or power digital watch 1020 constructed according to the invention. As in normal watches, a band 1022 secures the watch 1020 on a user's wrist so that the watch face 1024 can be viewed. A crystal 1026 provides the primary window through which to view data such as time on the display 1028. A user can adjust the time through a knob such as knob 1030.

The watch 1020 also holds a power sensing unit 1032, as described herein. The unit 1032 utilizes either its own microprocessor (e.g., a controller subsystem), or augments the existing microprocessor within the watch 1020 to provide like capability. The unit 1032 is controlled by interface buttons 1034a, 1034b, such as to provide ON/OFF capability and to display power performance data instead of time on the display 1028.

The watch 1020 of FIG. 38 thus provides "power" without the additional mounting of a sensing unit on a vehicle. Rather, this embodiment takes advantage of the fact that many sports include waving and movement of the user's arm (e.g., tennis and volleyball); and thus power is determined through the techniques herein to inform the user of this performance data, through the watch 1020.

Figure 39:
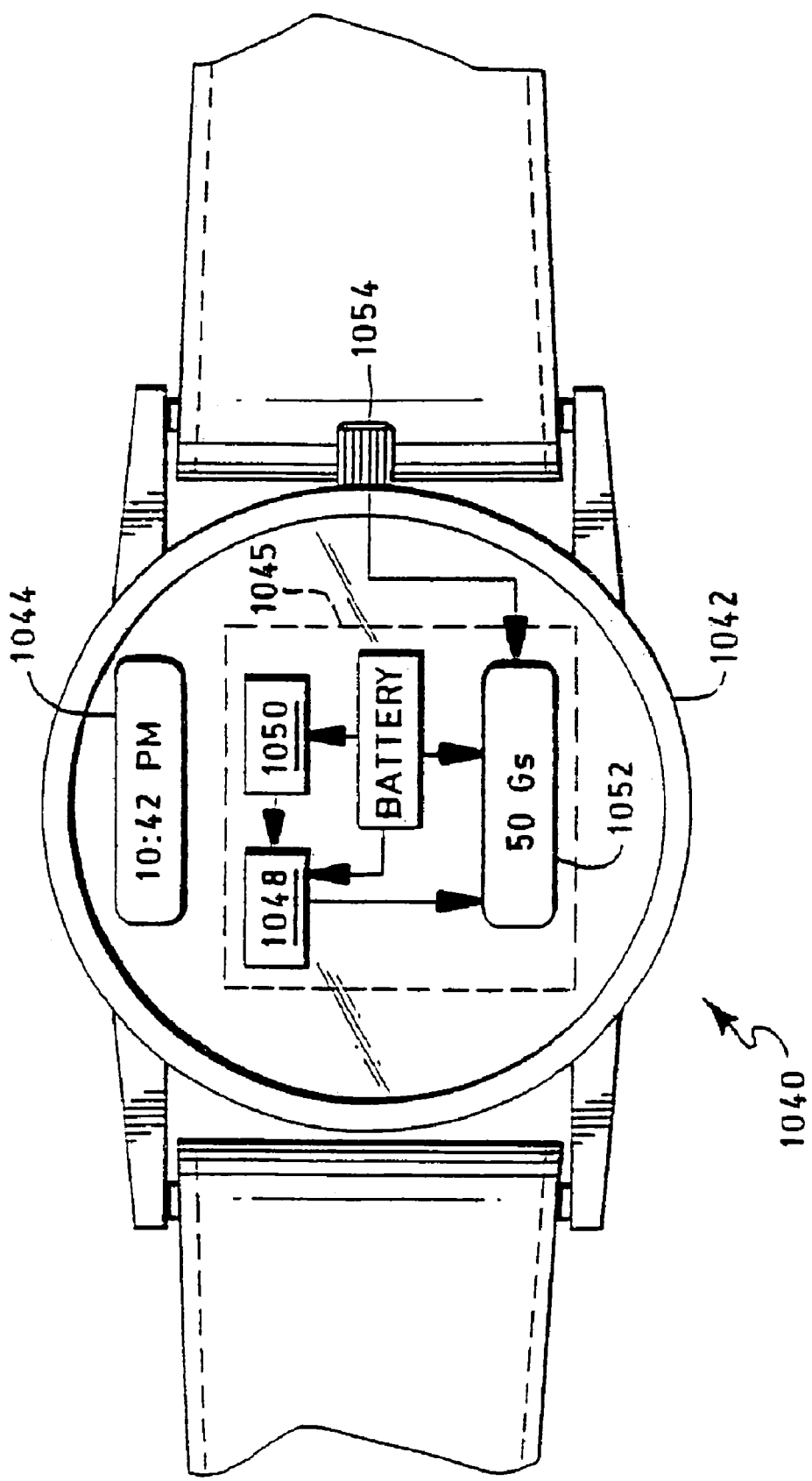
FIG. 39 shows another power watch configuration, in accord with the invention.

FIG. 39 illustrates another watch system 1040 for measuring power and informing a user of that power. As above, the watch 1042 is made to mount over the user's wrist. The watch 1040 functions as a normal watch, including, for example, a display 1044 to tell the user time (e.g., "10:42 PM"). Another portion of the watch includes a power sensing unit 1045, a processor 1048, force sensing element 1050 (e.g., a power sensor such as an accelerometer, or alternatively a microphone) and circuitry (not shown) to drive a display that informs the user of power. The processor 1048 processes the force data from the sensor 1050 and sends a signal to the display 1052 so that the user can see the power performance data (e.g., "50 G's"). The units on the display 1052 need not be actual units, such as G's, but relative units are acceptable to calibrate to other users and to repeated activity by the same user. A control knob 1054 provides access to the unit 1045 in a manner similar to the user interface buttons of FIGS. 1A and 1B.

Those skilled in the art should appreciate that an altimeter can also be placed in the watch 1040 so that, as above, the user is informed of drop distance. The button 1054 can also enable control of the unit 1045 so that one of drop distance, or power, is displayed on the display 1052. This dual drop distance and power watch embodiment is described in more detail in FIG. 40.

Figure 40:
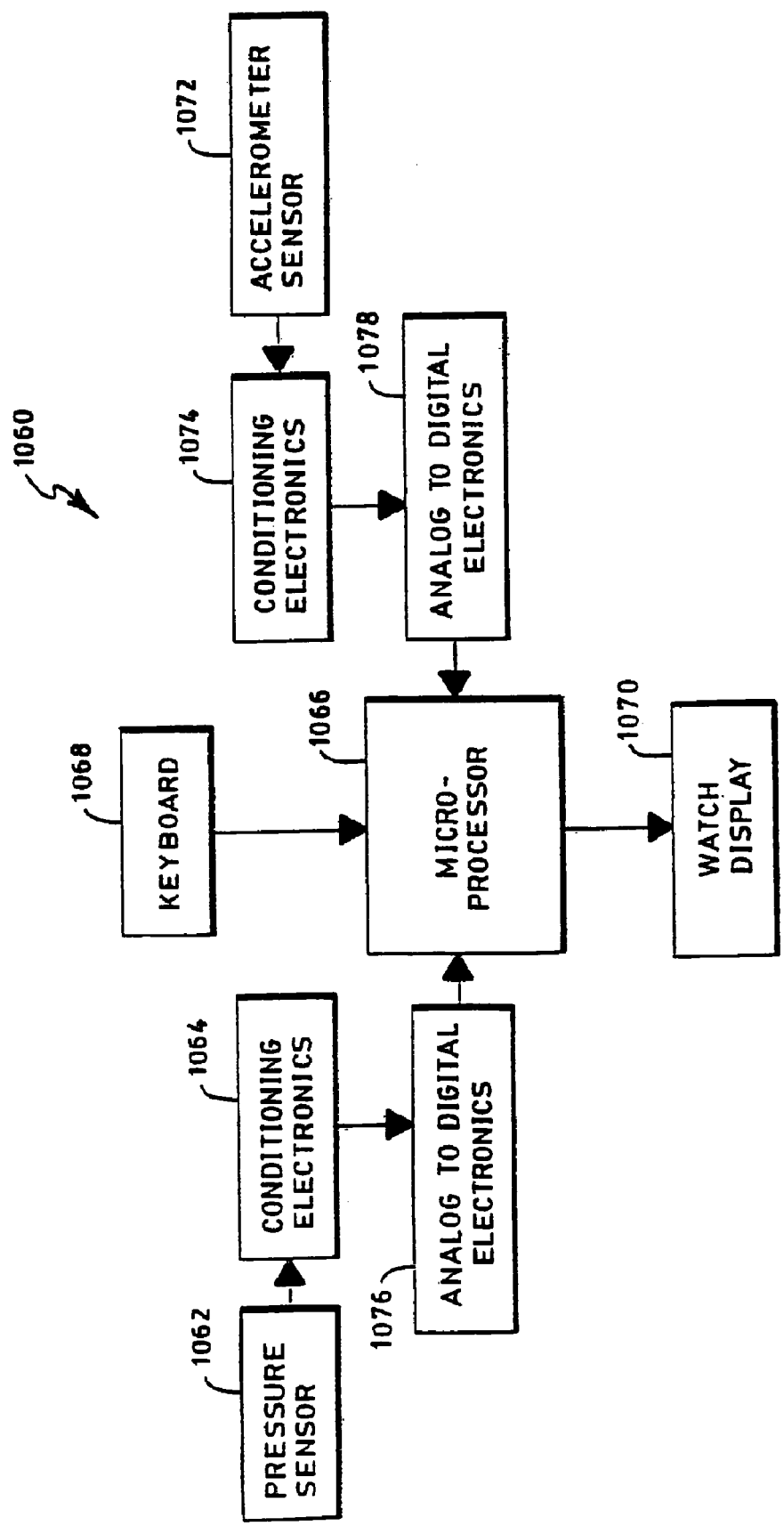
FIG. 40 shows a schematic view of a power/pressure system according to the invention.

FIG. 40 illustrates one block diagram of a power/pressure watch system 1060, constructed according to the invention. An altitude or pressure sensor 1062 as discussed above is conditioned by conditioning electronics 1064 which filter and scale the sensor's output. The data is then converted to digital by the Analog to Digital electronics 1076. The data is then read by the microprocessor 1066, wherein the data is processed by software and interpreted as altitude. The watch system 1060 includes a keyboard interface 1068 to set the time and the different performance data modes, as commanded by the user. Time is displayed on the watch display 1070, as normal.

System 1060 can further include an accelerometer 1072 which senses vibration and shock, as described herein, and which provides a voltage that is proportional to acceleration. This output is then conditioned by the conditioning electronics 1074 for scaling and filtering (such as through a combination of low pass and high pass filtering): the high frequencies limit is selected by anti-aliasing requirements while the low frequency limit is determined by low frequency noise rejection. The data is then sampled by the analog to digital electronics 1078 and read into the microprocessor 1066.

Drop distances may thus be determined by various sensors, including accelerometers, differential Global Positioning System (GPS) receivers, and pressure sensors, as discussed above. These sensors may be used in conjunction with airtime logic—which for example senses the abrupt change in the vibratory noise floor, potentially indicating the skier leaving contact with the ground—to give useful drop distances corresponding to airtime.

Accelerometers can also be used to determine airtime and the onset of free-fall. By using accelerometers to look at the ski vibration, airtime can be determined by absence of the vibrating spectrum, suggesting that the skis are no longer rubbing along the ground. Generally, this corresponds to the high frequency component to the acceleration signal. Accelerometers in the prior art also measure the acceleration due to gravity, which tends to change slowly. When a body free-falls, the force on the seismic mass associated with the accelerometer is zero because the seismic mass is no longer restrained. An accelerometer suite that measures acceleration in three translational directions will sum to zero in a free-fall. When the gravity acceleration returns, noted by the return of the low frequency acceleration floor, as well as by the return of the high frequency noise floor from skis rubbing on the ground, the system can determine the duration of free-fall—i.e., drop distance. The minimum distance d traveled in this free-fall along the axis of gravity known as true vertical may be determined by the formula $d = v_o t + \frac{1}{2} g t^2$, where d is distance traveled downward, g is acceleration due to gravity 32 ft/sec², $v_o$ is the initial velocity downward, and t is the number of seconds of free-fall. If the initial velocity $v_o$ is not known then the minimum distance $d_{min}$ can be determined by the rest of the equation $d_{min} = \frac{1}{2} g t^2$.

FIG. 9 showed the hardware block diagram for an accelerometer suite 207 capable of determining loft and free fall. The diagram included three linear accelerometers whose output are conditioned by electronics that strengthen and filter the signals. The output of the conditioning electronics is then fed into interface electronics that convert the signals from analog to digital.

Figure 41:
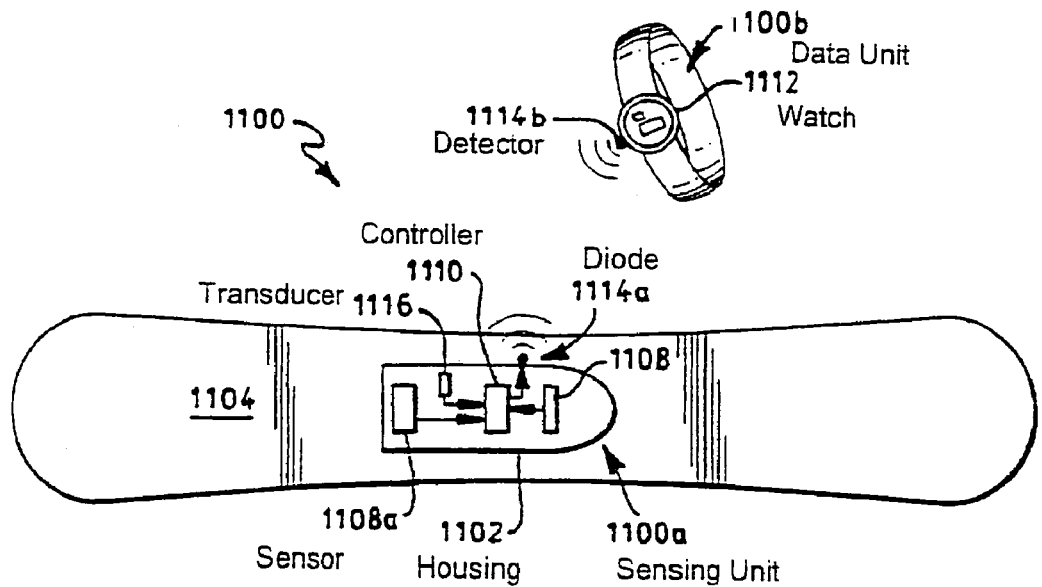
FIG. 41 illustrates a two-microphone speed sensing system of the invention.

FIG. 41 illustrates a top view of one preferred system 1100 for determining power and/or airtime (and/or speed discussed in more detail below). The system 1100 includes a sensing unit 1100a with housing 1102 mounted to a snowboard 1104 (alternatively, the system 1100 can be mounted to a ski, windsurfing board, bike, etc.) and a data unit 1100b, such as a data collection watch 1112 (such as the datawatch by Timex®). The housing 1102 forms an enclosure for the sensor, here illustrated as a piezo strip 1108 such as made by AMP Sensors, in Pennsylvania. The strip 1108 connects with the housing 1102 to measure sound within the box 1102. The box 1102 thus serves to amplify the sound heard through the ski 1104, and also compresses air within the box 1102 in a manner that is indicative of the force experienced by the box and thus the ski 1104. Accordingly, the strip 1108 measures not only sound, but a force-related factor that is used to determine power. In this manner, a microphone (e.g., the strip 1108) is suitable to measure both airtime and power. Further, by monitoring the pitch or signal strength of the sound within the box, a speed can be correlated with the sound. Accordingly, by a single microphone such as a piezo strip 1108, airtime, power and speed (or at least motion) are provided. A controller subsystem 1110 connects to the strip 1108 to process transducer data; and that processed data is transferred, for example, to the watch 1112 worn by the user by way of infrared energy signals from a diode/detector pair 1114a/b or other similar optical data transfer devices. The units 1100a and 1100b preferably permit communication between units, either direction.

Other transducers, e.g., an accelerometer or altimeter 1116 can also be placed in the box 1102 for processing and transfer to the user's watch 1112. The box 1102 is preferably sealed against environmental effects so as to protect the electronics therein. It is thus similar to the housing 32 of FIG. 1A. Because of the watch 1112, there is no separate need for a display in the sensing unit 1100a. A battery (not shown) powers the unit 1100a.

Another microphone such as the strip 1108a can also be included within the unit 1100a to provide additional speed sensing capability, as described below.

Figure 42:
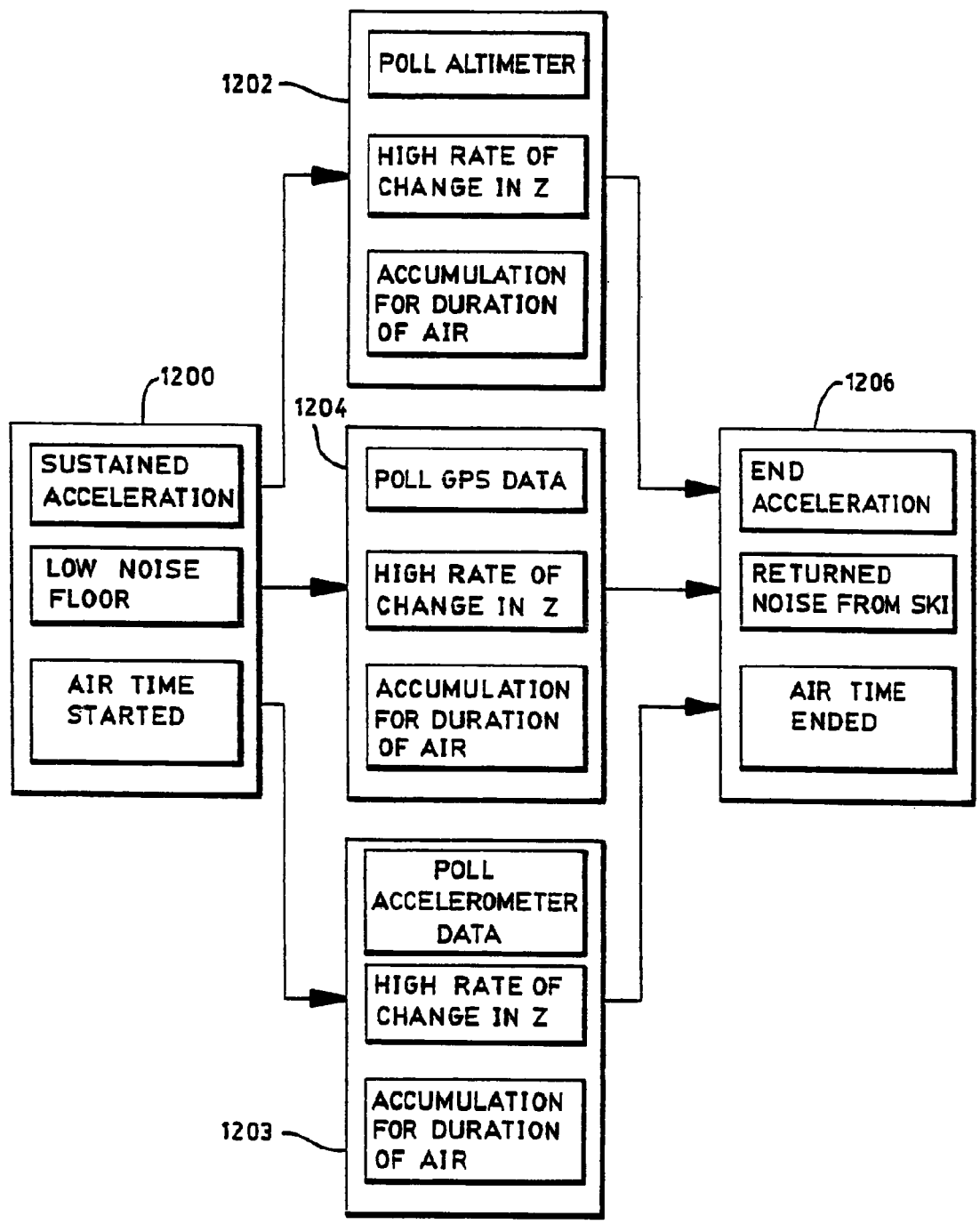
FIG. 42 illustrates process methodology for determining drop distance during airtime, in accord with the invention.

FIG. 42 illustrates that at the onset of airtime, the controller subsystem can trigger a drop distance calculation. Specifically, at an airtime sensed by an airtime sensing unit, a drop distance sensor—e.g., a GPS receiver, altimeter, or accelerometer—is polled to determine the change in vertical direction. In the event of a vertical drop, the first derivative in the z direction (True Vertical) should be a maximum. The signal flow diagram of FIG. 42 illustrates this logic:

Specifically, loft condition is first determined by the airtime sensor of block 1200. This data state is determined, for example, by the sudden absence of noise in the ski, causing an abrupt change in the near noise floor. The next data state is characterized by blocks 1202, 1204 and 1203. In state 1202 an altimeter is polled to determine if altitude is changing at a high rate, such as a rate associated with free fall. If so, the drop distance data is accumulated for the duration of the high free fall rate and the airtime. The state 1204 is similar to that of 1202, except for GPS receiver signals. In state 1204, GPS data is evaluated for a high rate of change in the Z direction. If there is a high free fall rate, the data is accumulated for as long as both the high rate and loft time are valid. The state 1203 corresponds to a data state using accelerometer data evaluation for airtime. As before, if the user is in free fall, the accelerometer does not experience an acceleration due to gravity. During this condition, drop distance data is accumulated during the airtime to determine vertical drop. The end of airtime signifies the end of the vertical drop, and state 1206 is returned. The distance of the drop is provided by the accumulation of the altimeter change, the change in GPS vertical height, or the duration of the accelerometer free fall and the laws of physics, as described herein.

Figure 43:
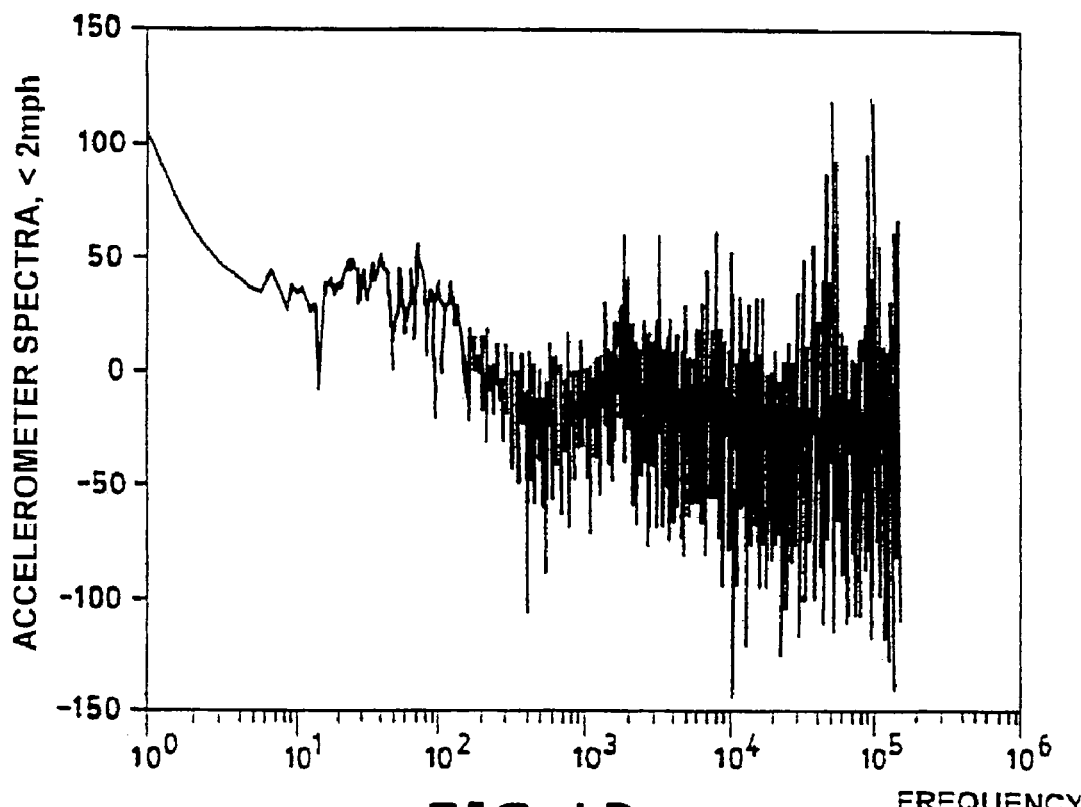
FIGS. 43 and 44 show real accelerometer data from a ski traveling at <2 mph and >15 mph, respectively, in accord with the invention.
Figure 44:
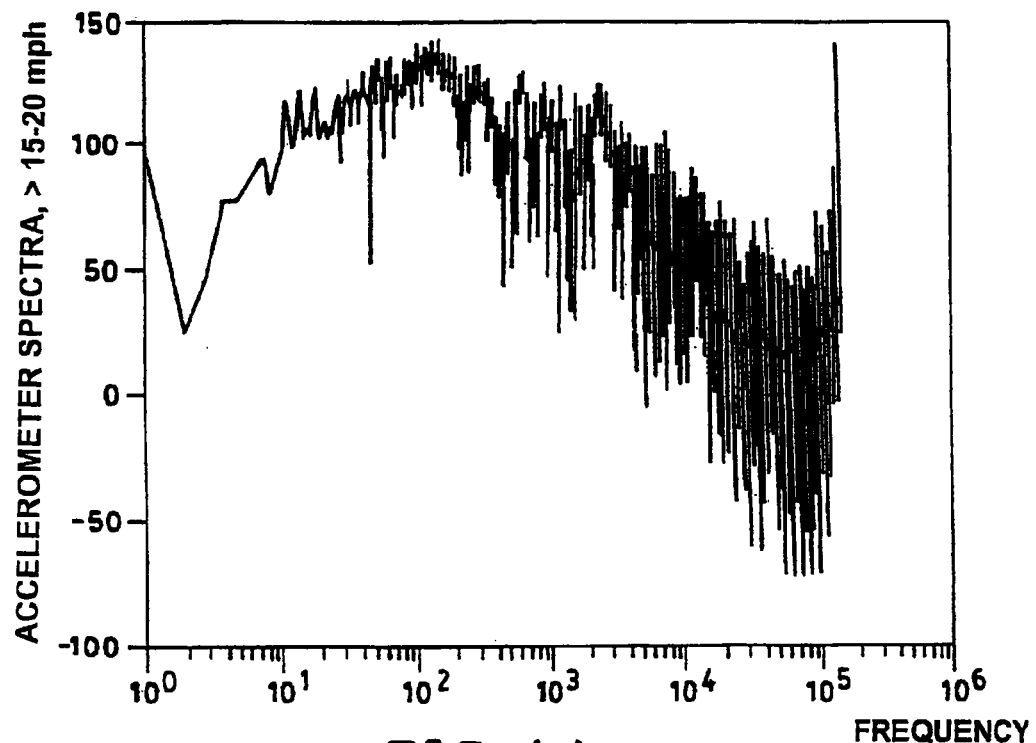

FIGS. 43 and 44 provide vibrational data corresponding to accelerometer data at less than 2 mph, FIG. 43, and greater than 15-20 mph, FIG. 44. The data acquisition system was the same as for the data of FIG. 6. As a ski moves faster over the surface of the snow, more of the energy from the spectrum is associated with the higher frequency components. Specifically, it is readily seen that the FIG. 44 has more power at higher frequency components. By segmenting and "binning" these frequencies, energy is isolated to such frequencies so that it can be compared to calibrated speed data at those frequencies. This is described below.

Note first that a microphone can provide basically the same information as the accelerometer above (that is, the data of FIGS. 43 and 44 appear similar to microphone data taken within a unit such as described in connection with FIG. 41), at least in frequency and relative magnitudes. Microphones are cheaper than accelerometers, and thus they are preferred for production reasons.

Figure 45:
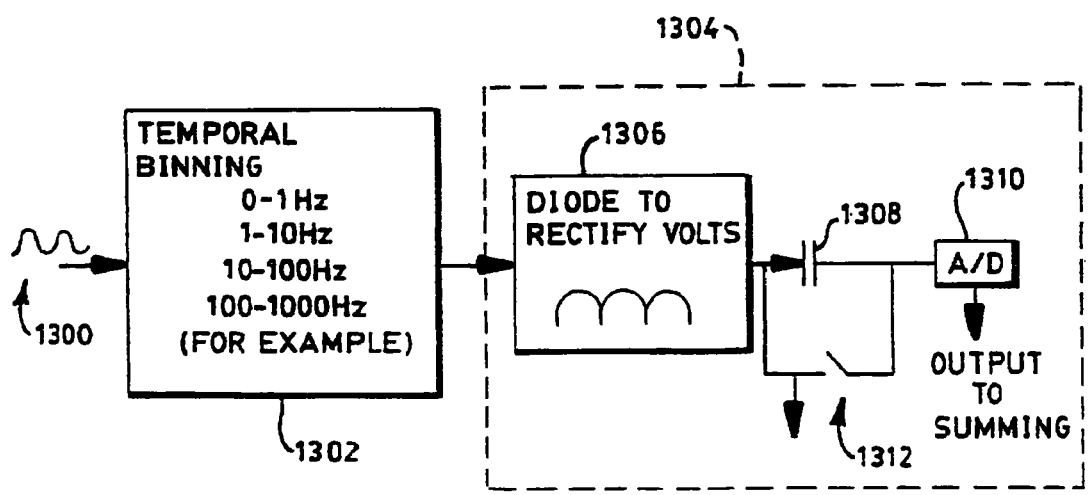
FIG. 45 illustrates one system for interpreting spectral data such as vibration to decipher airtime, power and speed, in accord with the invention.

With regard to FIG. 45, a force measuring sensor such as a microphone or accelerometer generates a voltage signal indicative of the spectra such as within FIGS. 43 and 44. This voltage 1300 is passed through an array of temporal filters which "bin" the appropriate results, according to frequency, such as shown in block 1302. The temporal binning of block 1302 can include a series of analog networks that pass specific frequencies only. For each frequency bin, the data is processed by modules 1304: the data is first rectified at block 1306 and a capacitor 1308 charges over the time constant of an A/D 1310 to integrate the signal of those frequencies; whereinafter the switch 1312 discharges in time for the next sample. The output is then summed according to frequency, for subsequent summing.

Those skilled in the art should appreciate that the process of FIG. 45 can be done within a DSP, wherein the steps of blocks 1302 and 1304 are accomplished through software modules. Accordingly, the unit 10 of FIG. 1A can thus simply process the data 1300 within the microprocessor 12a, or the logic functionality can be maintained in analog such as within the logic 12c or within other electronics not shown.

In any event, the various frequencies are then binned. For example, the low frequency 0-1 Hz is binned into the first bin, the 1-10 Hz frequencies are in the next, and so on (similar to the equalizer light on the home stereo system). For each time T (set by the A/D or other time—which is preferably at a reasonably fast rate, e.g., 100 Hz), the power in each frequency is integrated and assigned an integer value, such as: a typical value within 0-1 Hz is 1, a typical value within 1-10 Hz is 1, and so on. These values are integrated at a user selected interval (i.e., the power period). Further, the power values are preferably standardized to every user, so if you have 5 seconds of peak power activity, that will be saved—this number should be changeable to 10 seconds or even 1-5 minutes. A table created by this technique might appear as in Table I:

TABLE 1

Typical Frequency Binning, for Speed, Airtime and/or Power

| | Frequency | | | |
|---|---|---|---|---|
| | 0-1 Hz | 1-10 Hz | 10-100 Hz | 100-100 Hz |
| A/D Sample 1 | 1 | .5 | 1 | .1 |
| A/D Sample 2 | 2 | 1 | 2 | .3 |
| A/D Sample 3 | 1 | 2 | 1 | .4 |
| A/D Sample 4 | 2 | 1 | 3 | .3 |
| ... | ... | ... | ... | ... |
| A/D Sample n | X1 | X2 | X3 | X4 |
| SUM over time 1-n | 6 + ... + X1 | 4.5 + ... + X2 | 7 + ... + X3 | 1.1 + ... + X4 |

With time 1–n corresponding to the power period, power values are functionally dependent upon the SUM values, either within some or all of the bins. Note that the bins of FIG. 45 and Table 1 are chosen for illustrative purposes only; and that other bin sizes and ranges can be used in accord with the invention.

Fortunately speed can also be determined through these SUMs (although the summing "period" should be much faster than for power, and should typically be less than one second or even one tenth of a second). As noted above, there is a lot more high frequency content at faster speeds, FIG. 44, as compared to lower frequency content, FIG. 43. So, speed can also be correlated to such binned data, after obtaining a sufficient database of samples (preferably corresponding to the particular vehicle). Further, not all binning sections need to be used in that correlation. For example, one of the binning sections might readily produce a four factor increase of power for 15 mph as compared to 3 mph; and such increase is repeatable to correlated data.

Again, data for speed should not be integrated over time 1–n; but rather should be assessed for each sample or groupings of sample (e.g., an average of samples over a 1/10ths period). If for example a group of samples over any one second specify 15 mph data, then the speed sensing unit should report "15 mph event recorded". If only one sample has this value, then it should be discarded since—relative to 1/10 s intervals—the speed is substantially "steady state". That is, an average of ten speed summations over one second should, on average, all report the same 15 mph event.

The data of Table 1 can be also used for power. In one preferred aspect, power is a factor which is scaled to the third derivative of vertical distance moved with respect to time, essentially the change of acceleration (in the perpendicular axis to the ski or snowboard, if desired, or some other orientation) as a function of time. Specifically, power can be measured as:

$$\text{Power} \therefore \frac{\partial^3 x}{\partial t} \approx \frac{\partial A}{\partial t}$$

where x is distance moved in the selected direction (here, vertical to the ski face), and A is acceleration in the same axis.

In summary, selectable integral periods for power (e.g., 5 seconds, or 5 minutes, or other user-selected power period), and for speed (e.g., less than one second) are preferable, in accord with the invention. Note also that the filter bank 1302 is preferably adjustable and not limited to 0-1 Hz, 1-10 Hz, 10-50 Hz, and 50-250 Hz.

Figure 46:
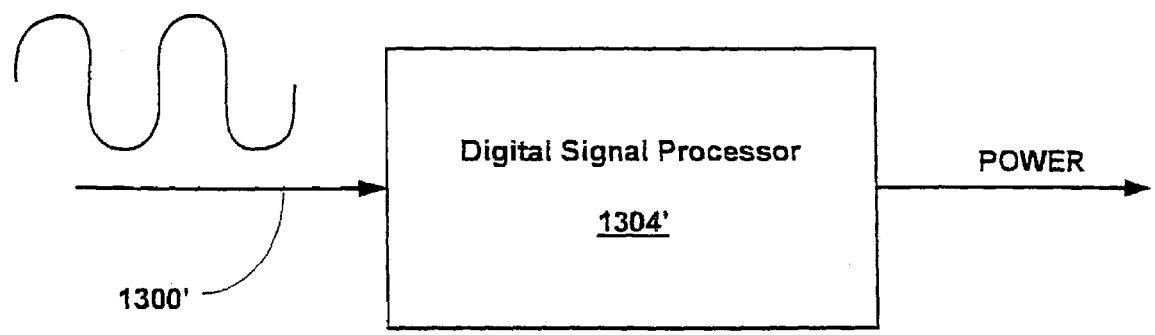
FIG. 46 illustrates use of a DSP to determine power in accord with the teachings of the invention.

FIG. 46 illustrates the capture of data 1300', such as digital or analog data from an accelerometer, by a DSP 1304' within a sensing unit of the invention. The DSP converts data 1300' to power by one of several disclosed algorithms: by evaluating one or more frequency ranges of the data 1300', by determining vertical motion relative to a face of the vehicle and assessing that motion with an exponential factor for a selected time period, or by determining a vertical velocity relative to a face of the vehicle and assessing that velocity with an exponential factor.

Note also that airtime can also be isolated from the data of Table 1. For airtime, the low frequency bins of 0-1 Hz and especially 1-10 Hz will be very small; and the controller subsystem will immediately identify this loss of power, in these binned frequencies. Since airtime can be less than one second, the moving averages which integrate the data should be substantially less than the airtime minimum. Essentially, the airtime binning is a one-dimensional convolution between a rect function (defining the period) and the data of the lower frequency bins. A similar convolution can be applied to determine factors such as power and speed, except that the rect size is larger and different bins are likely used.

Power can be determined in other ways too, in accord with the invention. Specifically, power can be defined as the rate at which energy E is expended. Power and work are related by:

$$P = dE/dt$$

By having an estimate of the energy associated with the user's movement, over time, then an estimate is also available for the power expended by the user. The kinetic energy of a simple mass is expressed by:

$$E = \tfrac{1}{2} m V^2$$

Thus energy is proportional to velocity squared. Velocity, or speed, is determined in several ways herein. For example, velocity can be determined from an accelerometer by integrating acceleration over time after subtracting the 1 g acceleration of gravity. In a sampled system, velocity at any point in time (at interval $\Delta t$) is equal to:

$$V \approx \Sigma A \Delta t$$

where A is the measured acceleration with the 1 g acceleration removed. Velocity is squared to obtain a quantity proportional to the kinetic energy:

$$E = V^2$$

The total power over some finite time interval N is thus proportional to:

$$P \approx \frac{1}{(N-1)\Delta t}\sum_{i=1}^{N}(V_i^2 - V_{i-1}^2)$$

If for example the accelerometer is attached to a ski or snowboard, then a significant portion of the measured acceleration may be due to the oscillations of the ski/board at its resonant frequencies. These oscillation are the ski/board's response to its dynamic loading environment and may not be indicative of the power that the skier/boarder experiences. It is therefore worthwhile to process the accelerometer signal so as to reduce the contribution made by ski/board vibration to the power measurement. The resonant frequencies of the board and skis are significantly higher than the dynamics that the skier's body experiences. Thus, the contribution of the ski/board resonant response to the accelerometer measurement can be reduced by applying a low pass temporal filter to the data prior to integration.

Figure 48:
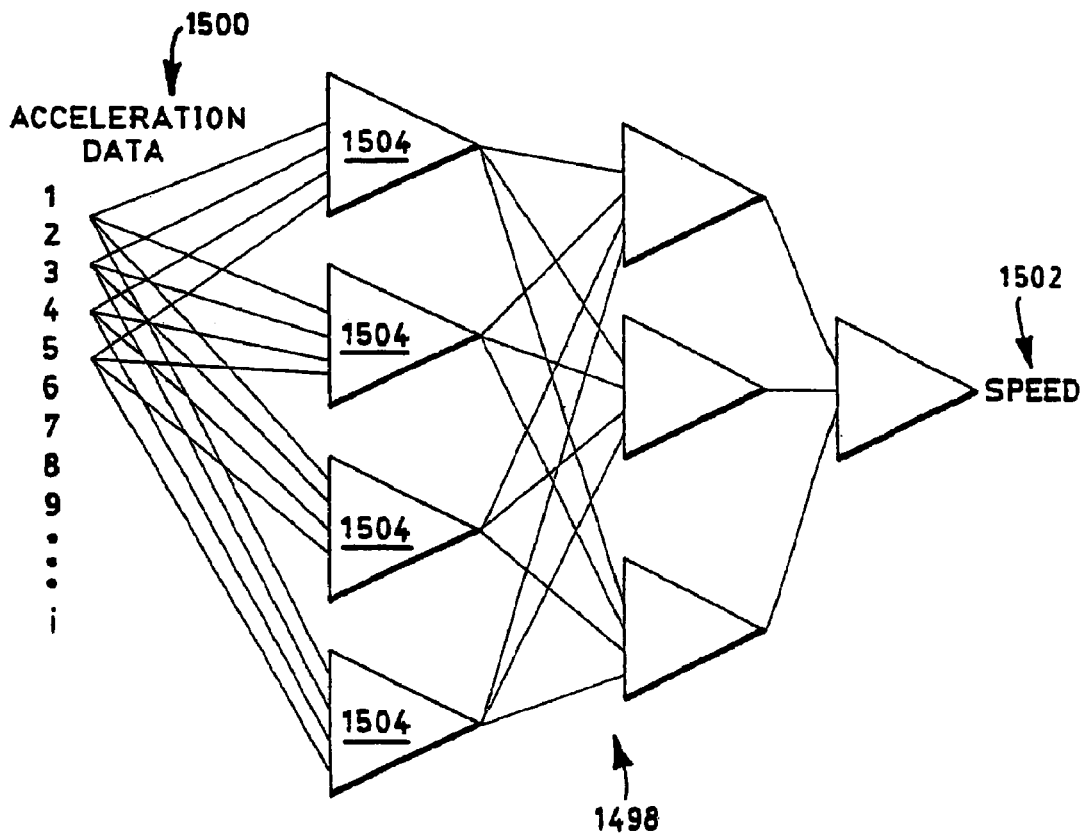
FIG. 48 illustrates a neural network of the invention.

One way of developing an algorithm to deal with extracting speed from acceleration data (or microphone data or other force sensing output) is through a neural network. A neural algorithm is one that is developed through a learning process, including force sensing data from the sensor and speed data correlated during test. The neural algorithm builds a network that will process the data. It starts off by using a small number of samples and a small number of stages. The output is derived by weighting factors on the samples and added together. The output becomes a weighted average of the inputs, i.e., a multiple stage moving average filter. The output is then compared with the speed waveform and tested to see how well it produces the correct result. If the test fails, the number of samples is then increased or the number of stages is increased, or both. FIG. 48 illustrates an exemplary neural network 1498 windowing down acceleration data 1500 to achieve the correlated speed 1502. Specifically, FIG. 48 shows the construction of a network 1498 where four samples 1,2,3,4 are fed into four stages 1504, and where each sample is multiplied by a weighting factor or gain. The network 1498 is then tested to see if input data produces speed data. If not the number of samples used as input are increased as are the number of stages. At each network the relative gains are also changed to see if that will produce the required result.

Other Techniques for Speed Estimation

In accord with the invention, speed can also be determined based upon the characteristics of the resulting friction-induced noise spectra. When the vehicle—be it a ski, snowboard, waterski, etc.—passes over the surface, the spectra will have a bandwidth content that increases with vehicle speed in a deterministic fashion (if one can assumes that the spatial spectral content of the surface is invariant with respect to time and location). As such, the following describes a two-sensor technique for estimating delay times of transport processes. The unit 1102 of FIG. 41 includes two such sensors—i.e., the two piezo strips 1108—which are suitable for such process measurements.

Figure 49:
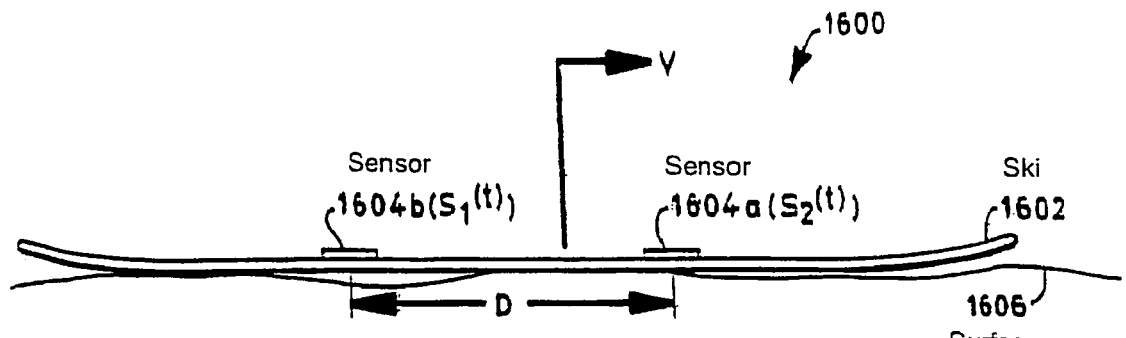
FIG. 49 illustrates methodology for a two sensor speed sensing unit of the invention.
Figure 50:
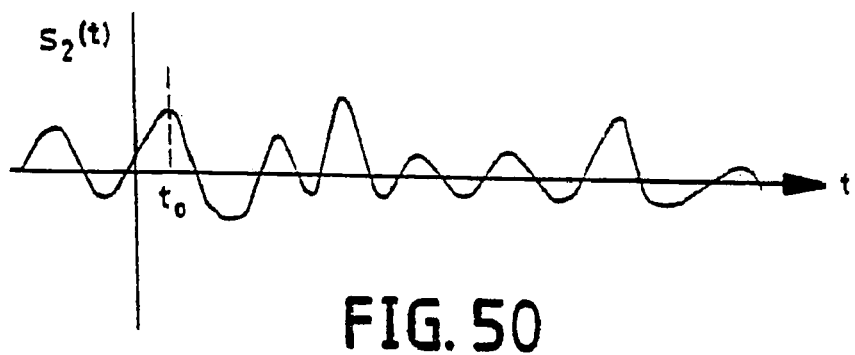
FIGS. 50-51 show representative spectra from the two sensors.
Figure 51:
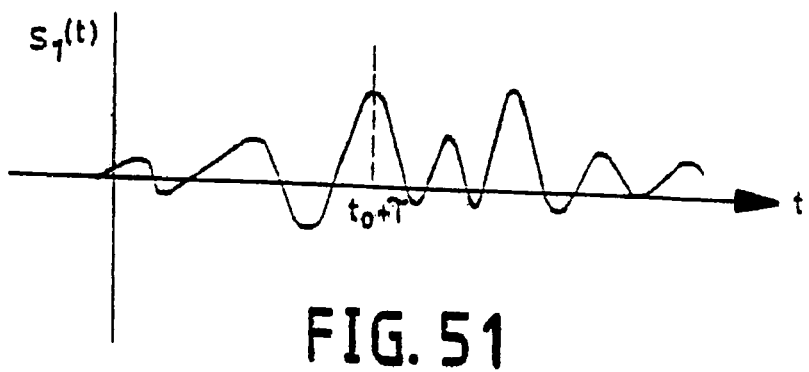

Consider the system 1600 depicted in FIG. 49. A ski or snowboard 1602 is instrumented with two vibration sensors 1604 such as described above. These sensors 1604 are attached a distance "D" apart. The ski moves at a velocity "V" over the snow surface 1606. The front-most sensor 1604a provides a vibrational output $s_2(t)$, a typical example of which is plotted in FIG. 50. The rear-most sensor 1604b provides a vibrational output $s_1(t)$, plotted in FIG. 51. Assuming that the characteristics of the snow surface 1606 which induce the response $s_2(t)$ do not change significantly as the ski 1602 passes through a distance D, and that the speed of the ski 1602 does not vary significantly over that time, then $s_1(t)$ will essentially be a replica of $s_2(t)$, delayed by an amount of time τ. This is seen by considering the feature of the vibration spectra at time to in FIG. 50. This trace can be conceived of as "sliding" along the time axis t to produce FIG. 51, except now the aforementioned feature of the time trace appears at time $t_0+\tau$.

If one estimates the time delay t accurately, then one simply uses the relationship DISTANCE=VELOCITY×TIME to infer the velocity V:

$$V = \frac{D}{\tau}. \tag{1}$$

This same methodology has been applied in measuring the characteristic propagation times (and thence speeds) of spatial features in turbulent flow over wings and other surfaces.

Since the vibrational input can be thought of in a local frame (the "sensor frame") as a random process, one can use conventional statistical means to infer the delay time t, and thence V. Typically, this is done using correlation functions. Define the cross correlation function $R_{12}(\tau)$ as $$R_{12}(\tau) = \lim_{T \to \infty} \frac{1}{T}\int_0^T s_1(t)s_2(t+\tau)dt \tag{2}$$

Figure 52:
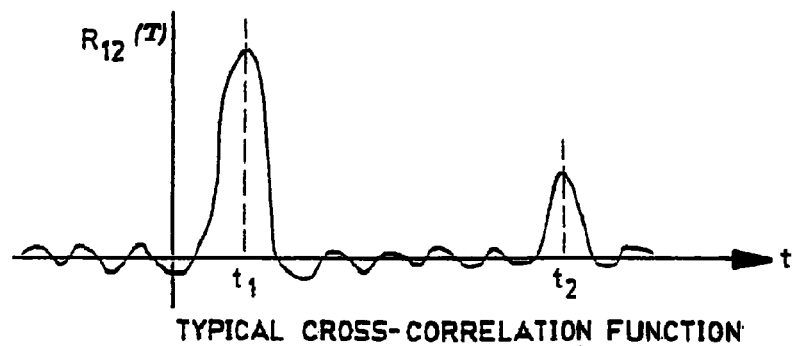
FIGS. 52-53 show illustrative correlation functions.

A typical cross correlation function is plotted in FIG. 52 (note that this cross correlation function depicts a system with two characteristic time delays, $t_1$ and $t_2$).

Figure 53:
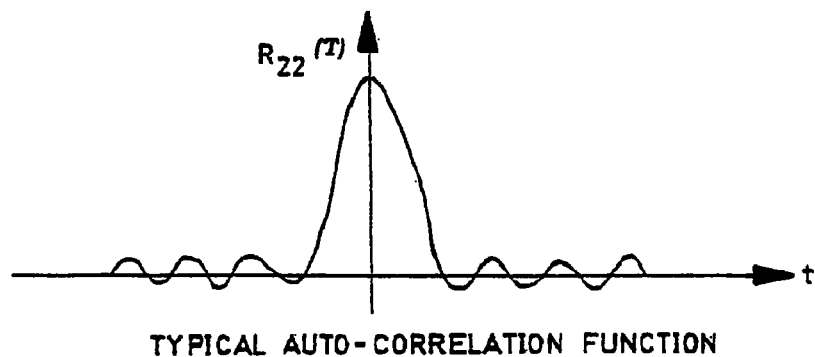

The most straightforward interpretations of cross correlation functions are in the context of propagation problems. For non-dispersive signal propagation of the type considered here, even in the presence of additive noise associated with the sensors, one can show that $$R_{12}(\tau) = R_{22}\left(\tau - \frac{D}{V}\right), \tag{3}$$

where $R_{22}$ is the autocorrelation of $s_2(t)$. A typical autocorrelation function is plotted in FIG. 53. Thus, the cross correlation of equation (2) will look like the autocorrelation of $s_2(t)$ shifted by the amount D/V along the correlation time axis. Using this fact, one can readily infer the delay time τ by searching for the peak magnitude of the cross correlation function (whose construction is described below), and then computing the velocity V using equation (1) since D is known. Thus, a two-sensor system will permit the measurement of the speed V independent of the spatial spectral content of the snow surface.

Note that the separation D is shown with large separation for purposes of illustration; when in fact that distance will typically reflect a small separation such as illustrated by the separation of the sensors 1108 of FIG. 41.

There are a few practical considerations to be kept in mind when computing $R_{12}$, and in interpreting its characteristics. First, unlike autocorrelations, extraneous noise at the sensors 1604a, 1604b only reduces the relative contributions of individual correlation peaks and increases the random error in the measurement; but it does not distort or bias the result, hence the time delay measured will be the true time delay. Secondly, one should determine a priori if there are any secondary propagation paths for the vibrational signal that first enters sensor 1604a to reach sensor 1604b before the ski slides over the snow the distance D.

Figure 54:
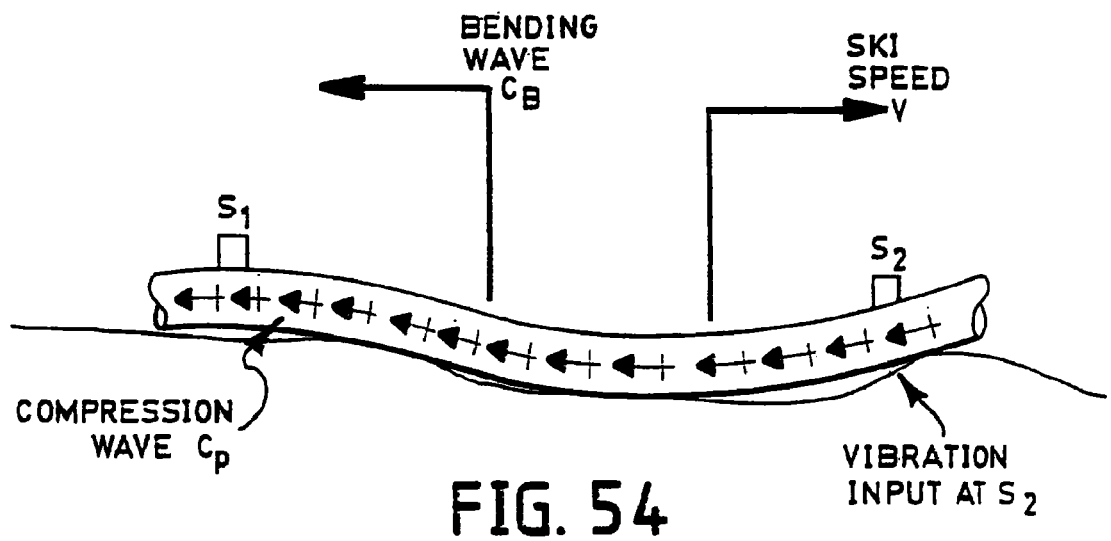
FIG. 54 illustrates a bending wave within a ski which can be used for power sensing, in accord with the invention.

This may occur in skis or snowboards, as is shown in FIG. 54. The board/ski can support bending modes via flexing, which have a characteristic (slowest) propagation speed "$C_B$". Also, the material within the board can support the equivalent of acoustic (sound) waves within it, with characteristic propagation speed "$C_P$". This would lead to a cross correlation having two correlation peaks, each of which corresponds to the delay time associated with transmitting the vibrational input at 1604a to sensor 1604b via bending and compressional waves, respectively. If these wave speeds are comparable with the skier's speed V, then one will not distinguish skiing speed from the natural vibrational response of the board/ski 1602. Fortunately, these vibrational wave speeds should be faster than the skier's speed, and thus appear at a much shorter delay time on the correlation plot: the characteristic wave speed in aluminum is 20,664 feet/sec, in ice about 10,496 feet/sec, and in rubber about 7872 feet/sec for compressional waves. The bending wave speed will typically be slower, but can only be computed for well known geometries and material compositions, and is usually easier to measure in the lab beforehand. If there should ever be a problem in measuring the speed V via the cross correlation of equation (2), it will likely be attributable to this. Should that problem occur, one can readily get around it by changing the sensor spacing D, which would thence change τ.

The cross correlation is computed from digital samples via $$R_{12}(r\Delta t) = \frac{1}{N-r} \sum_{n=1}^{N-r} s_{2 \cdot n} s_{1 \cdot n+r}, \quad (4)$$

where r defines the sample lag number at which the cross correlation is being computed, N the number of sample points in the time records, and the subscript n denotes the n-th element in the time record, and Δt is the sampling rate of the system. This function can be normalized to have unit magnitude by dividing through by the square roots of the zero-delay auto correlations of the signals $s_1$ and $s_2$ (e.g., the variances of these signals):

$$\rho(r\Delta t) = \frac{R_{12}(r\Delta t)}{\sqrt{R_1(0)}\sqrt{R_2(0)}} \quad (5)$$

for $$R_1 = \frac{1}{N}\sum_{n=1}^{N}(s_{1,n})^2; R_2 = \frac{1}{N}\sum_{n=1}^{N}(s_{2,n})^2. \quad (6)$$

This simplifies the setting of thresholds for selecting the delay time τ corresponding to the skier speed V. Also, one can restrict the set of lag numbers r if you already have some idea of the expected delays, given the speeds you expect to encounter skiing or boarding (or other sports, since these techniques apply to other sports and are discussed in the context of skiing for illustrative purposes only).

The means to test this measurement and processing methodology is to mount sensors on the board or ski, and first measure the correlation function of equation (4) for all r. Then, compute the speed V per equation (1), and compare it to that measured with a truth sensor, such as a police radar gun, or a simple wind anemometer. Also, compute the standard cross spectra function as found on most any spectrum analyzer to see if the phase of the cross spectra denotes a pure lag (a progressive phase shift when unwrapped) over a range of frequencies (as would be expected here). This method though requires that you compute two FFTs, do a complex multiplication, and then compute the phase via an arctangent, all in real-time. If you see several delay times in the cross correlation, as might be found for a particularly floppy set of skis with a very, very slow bending wave speed, move the sensors and see if these peaks shift so as to separate out the propagation delay due to skiing. The only limitation here is the spatial coherence length of the snow/board interface, which needs to be observed experimentally.

Regarding expected delays, consider the Table 2 of delay times (in msec) for two separations: D=1.5 fit (as might be found in a foot-to-foot spacing on a board), and D=4 ft. The delay T1 corresponds to D=1.5 ft, and T2 corresponds to D=4 ft.

TABLE 2

| | Delay processing times | |
|---|---|---|
| speed | T1 (msec) | T2 (msec) |
| 5 | 204.5 | 545 |
| 10 | 102.2 | 272.7 |
| 15 | 68.2 | 181.8 |
| 20 | 51.2 | 136.5 |
| 25 | 41 | 109.3 |
| 30 | 34.1 | 90.7 |
| 35 | 29.2 | 77.9 |

Table 2 shows that to resolve the speed to within 5 mph, which represents one suitable quantizer for speed sensing for the invention, one needs to be able to resolve a time delay at the higher speeds of about 5 msec for the short baseline (D=1.5 fit) case. To resolve this with a fitness of, e.g., one part in 10, you must sample at 0.5 msec, which implies a bandwidth of 2 kHz for the short baseline system. This is not an onerous sampling requirement, especially in view of modern processing capability. Nonetheless, this is a 2 kHz sample rate on two channels (i.e., for the two sensors), sampled with simultaneity better than 0.5 msec as well (e.g., easily achievable inter-channel skew, even for a system without simultaneous sample and hold amplifiers).

Another implementation issue is the fact that the system will lose tracking during airtime, or perhaps when carving an especially aggressive turn, especially in very soft snow. Thus, it is preferably to implement a last estimate hold feature on the display of speed information: if the data is not good enough to update the speed (e.g., if the signals drop below a certain level indicative of air, if an air "trigger signal" is used as a conditional trigger, or if the correlation threshold level is not met), then continue to display the last value measured.

Figure 55:
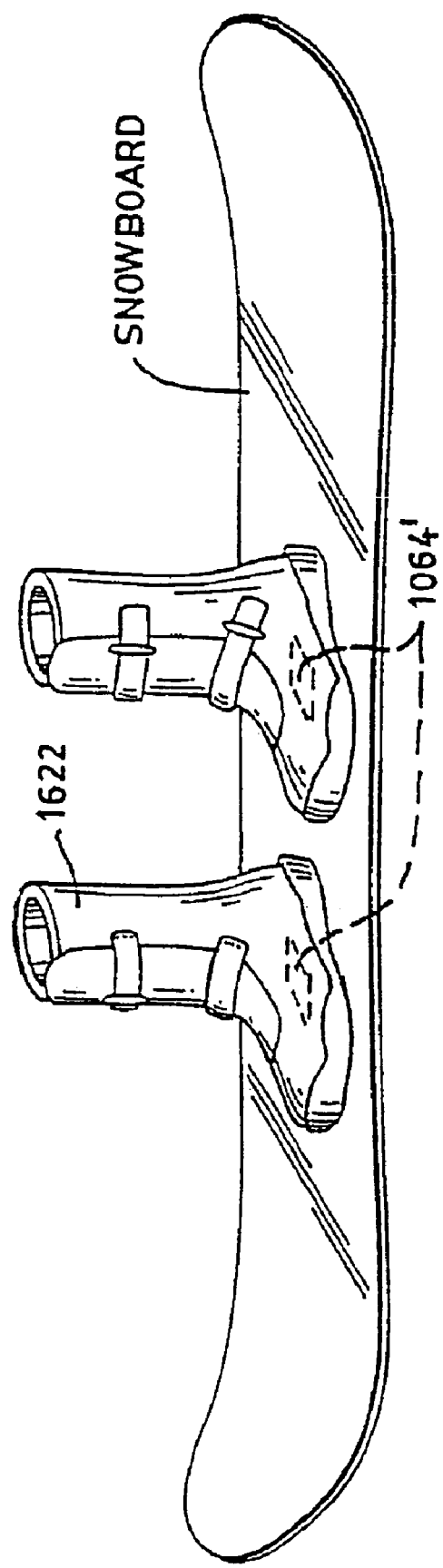
FIG. 55 shows a two-sensor speed system constructed according to the invention.
Figure 56:
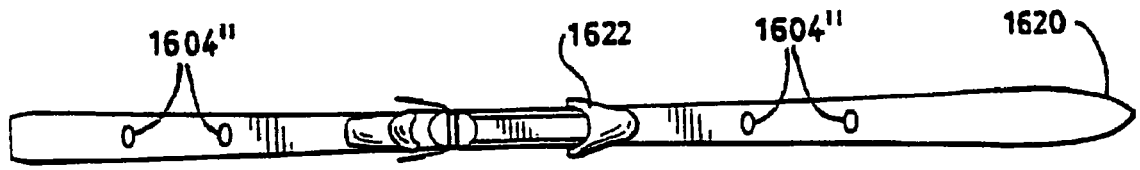
FIG. 56 shows a multi-sensor speed system constructed according to the invention.
Figure 57:
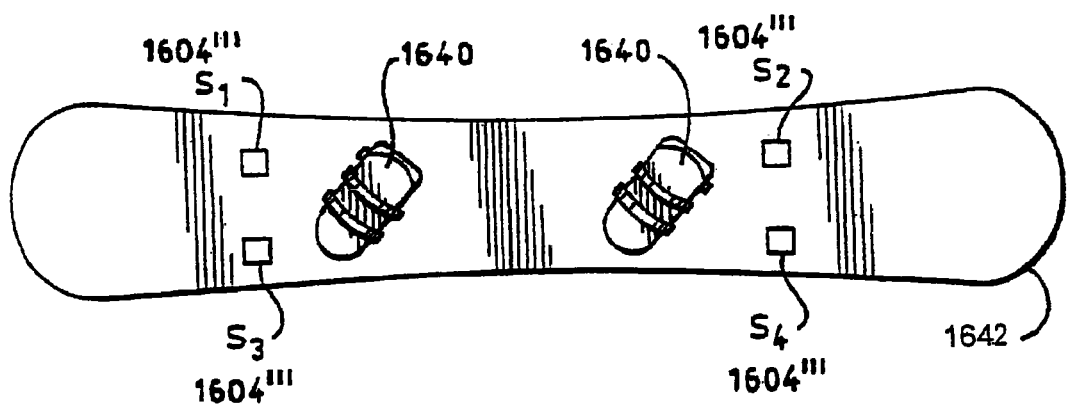
FIG. 57 shows a two-dimensional sensor speed system constructed according to the invention.

Other speed measurement implementations are provided in FIGS. 55-57. In FIG. 55, the two sensors 1604' are integrated beneath a snowboarder's boots 1622, or even within the boots' soles. In FIG. 56, a multiplicity of sensors 1604" is included with a ski 1620 (showing a binding 1622), and the cross correlation is computed across any pair so as to maximize the signal to noise ratio, or even to adapt to differing snow conditions or skier speeds. In FIG. 57, a two-dimensional array of sensors 1604''' is shown arranged around the boot mounts 1640 of a snowboard 1642, where one may employ either "$s_1$-$s_2$" or "$s_3$-$s_4$" sensor pairs to measure V depending on which side of the board is dug in (so as to maximize the sensor signals). One may also employ either $s_1$-$s_2$ or $s_3$-$s_4$ to infer side-slip via correlation measurements as well.

Figure 58:
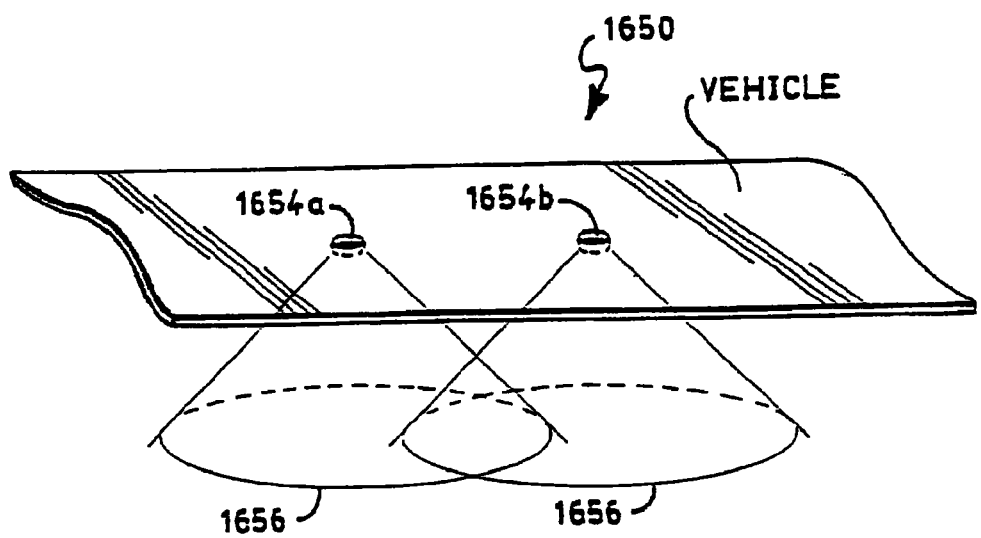
FIG. 58 and FIG. 59 show a Doppler-based system constructed according to the invention.
Figure 59:
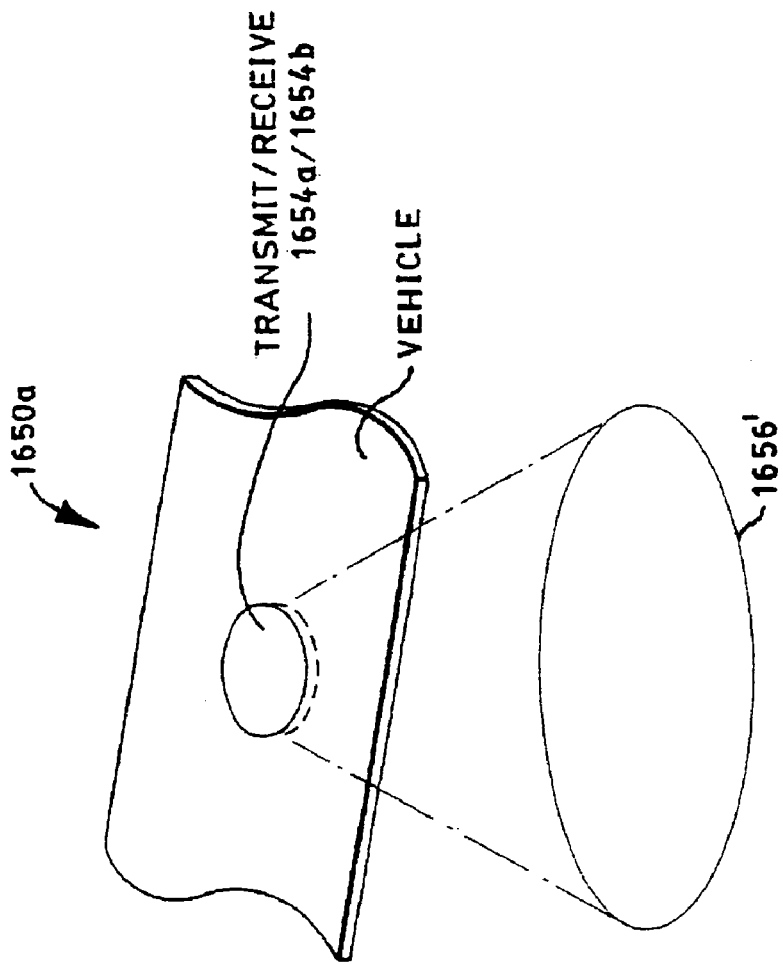

An alternative speed measuring system 1650 is shown in FIGS. 58 and 59, incorporating a down-looking Doppler system: system 1650 utilizes "bistatic" sonar, while system 1650a utilizes "monostatic". All of the transducers 1654 and their operating frequencies are chosen so that the resulting acoustic fields 1656 have wavelengths larger than the transducer diameters, making the radiation and receive patterns broad and overlapping. The transmitter (the "pinger") 1654a transmit a pulse, a CW signal, or a band-limited FM signal, and the receiver 1654b senses this signal and infers speed from the associated Doppler shift.

The system in FIG. 59 is of particular interest, as it combines transmit and receive functions in a single element, reducing cost. Further, if one uses a pulsed signal in this configuration, then one could use it not only to sense Doppler, but distance and height too (by applying a time gate to the return). A near gate would be set to preclude measuring random hops and skips, but will instead see true "air" when the ski/board is sufficiently high above the snow. One rangefinding system manufactured by Polaroid can function as such a system, with electronics for under $10.

Other Techniques for Power Estimation

Power can be used to quantitatively establish "bragging rights" among users, allowing them to compare level of effort expended during a run, over the course of a day, etc.

Power is defined conventionally as the rate of energy transfer into or out of a system. As such, power is an instantaneous quantity, rather than an integrative measure. Consequently, power can be determined as that energy expended over a run, providing a suitable metric to measure and report.

There are three chief components leading to energy expenditure in sports such as skiing and snowboarding:

1. Frictional resistance as the vehicle moves across its supporting surface, impeding the motion of the vehicle;
2. Air drag (both form drag and frictional resistance), impeding the motion of the vehicle/operator system;
3. Supporting the operator upright in the presence of external forces, such as those encountered when skiing over moguls, riding a mountain bike over rough terrain, or when countering the pull of a tow rope when water skiing.

Frictional drag can be modeled in a variety of ways. Nominally, if the resistance is viscous in nature, then the retarding force is linearly proportional to the vehicles speed V:

$$F_d = c \cdot V \quad (1)$$

where "c" is the viscous drag coefficient, which should be determined empirically. Note that the frictional force is linearly proportional to the velocity V; while in practice the proportionality is nonlinear, the approximation will suffice for present purposes. The linear coefficient can also be estimated, measured or ignored (since power units can be unitless and preferably correspond to suitable numbers to compare multitudes of users in an easy manner). From conservation of energy, $$\frac{1}{2}mV^2\sin^2\theta = mg\Delta h - \int_0^{t_f} cV^2(t)\sin^2\theta dt, \quad (2)$$

where θ is the angle of the slope, "m" is the mass of the user (e.g., skier+skis), and Δh is the vertical drop between gates. Since the velocity profile is linear over time, $$\int_0^{t_f} cV^2(t)\sin^2\theta dt = \frac{1}{3}cV^2\sin^2\theta t_f, \quad (3)$$

and thence $$c = 3\left[\frac{mg\Delta h - \left(\frac{mV^2\sin^2\theta}{2}\right)}{V^2\sin^2\theta t_f}\right]. \quad (4)$$

With respect to the impact on energy expenditure during the activity, the instantaneous power loss is given by $$P_d(t) = \begin{cases} F_d(t) \cdot V(t) = cV^2(t); & \text{vehicle in contact} \\ 0; & \text{vehicle not in contact} \end{cases} \quad (5)$$

Assuming that the frictional coefficient is constant over the run, then if one measures V(t), as discussed above or by some other estimation, then the total energy expenditure due to friction over a run is given by $$E_d = \int_0^{t_{end}} P_d(t)dt, \quad (6)$$

where $t_{end}$ is the finishing time.

The resistive force due to air frictional drag is in general proportional to the square of the velocity, hence the energy loss over a run will be proportional to the time integral of this resistive force times the velocity. The proportionality constant will in general be difficult to estimate, or even measure. However, roughly it is proportional to a constant times the cross sectional (frontal) area of the user. One can get a first cut at this area by assuming that the width of a skier is a fixed proportion of their height, then from a measurement of weight (measured, for example, using the FSR means previously described) and a standard actuarial table for weight/height correlation. Thus, $$E_a = \int_0^{t_{end}} amV^3(t)dt \cong \sum_{i=1}^{\left(\frac{t_{end}}{\Delta t}\right)} amV^3(t_i)\Delta t, \quad (7)$$

where "m" is the mass of the skier. The proportionality constant "a" is set heuristically.

Figure 60:
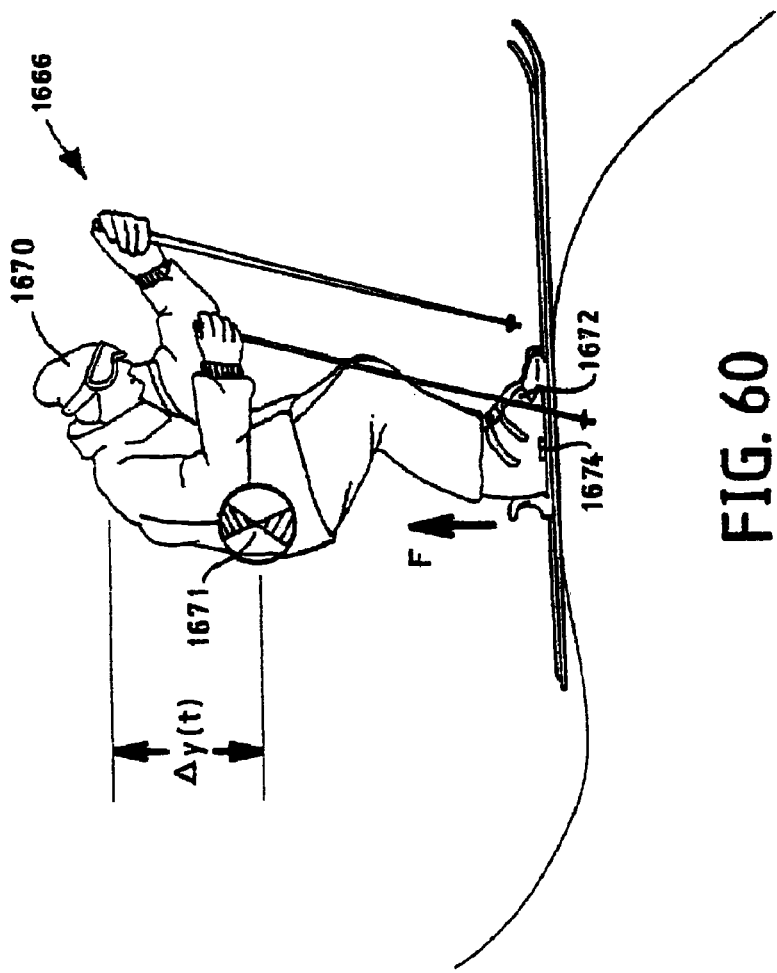
FIG. 60 shows a force measuring system of the invention.

Finally, the contribution to energy expenditure from supporting the operator upright in the presence of external forces can be estimated using a system 1666 of FIG. 60, where the user 1670 wears an accelerometer 1671 around her waist, capable of measuring the vertical component of acceleration Δy(t). Further, the ski/board/boot sole 1672 has a force measuring means 1674 (as discussed herein) to measure the force component "F". The operator 1670 will be dissipating energy by bending their knees, decelerating the mass of their upper body. Since the legs can be though of as rigid links with rotary springs at the knee and hip joints, the force due to this deceleration will be transmitted to the force sensing means (springs transmit forces). This, the instantaneous power dissipated in maintaining a tuck is given by $$P_b = F(t) \cdot \frac{dy(t)}{dt} = F(t) \cdot \int^t y''(t) dt. \quad (8)$$

Note that this equation is not conditional with respect to vehicle contact as per equation (5) of this section, as the reaction force F goes to zero when the vehicle leaves the surface. The energy expended over a run due to this effort is then given by $$E_b = \int_0^{t_{end}} F \cdot \left[ \int^t y''(t) dt \right] dt. \quad (9)$$

In total, the energy expended over a run is given as the sum of the three energy components:

$$E_{total} = E_d + E_a + E_b \quad (10)$$

Figure 62:
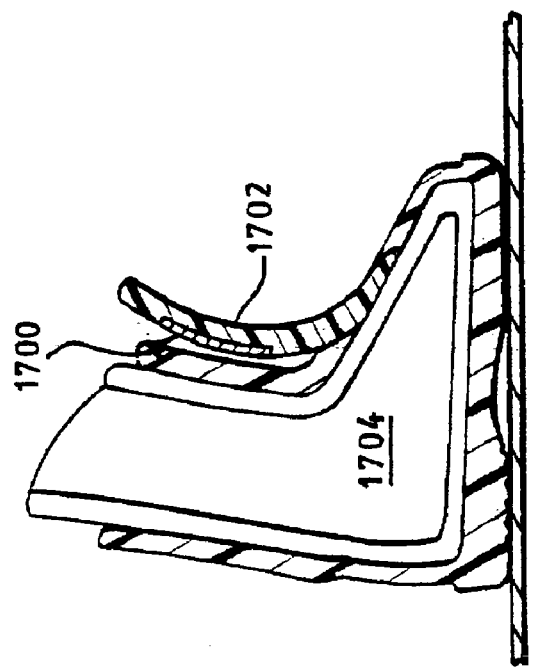
FIGS. 61-62 show alternative systems.
Figure 61:
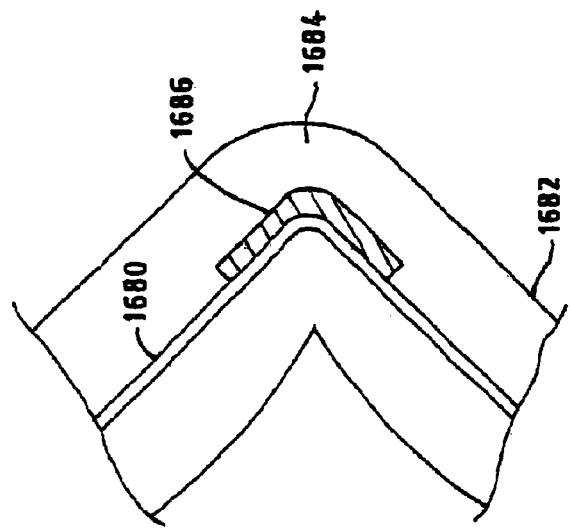

Alternate systems to measure the skier's hip position y(t) (shown in FIG. 60) is provided in FIGS. 61 and 62. In FIG. 61, a flexible element 1680 is sewn into the skier's pants 1682, covering the leg 1684. A PVDF or NiTiNOL SMA strip 1686 is bonded to the element 1680, and will act as a large-area strain gage. When the skier bends his knees the gage 1686 will stretch, and to first order this strain will be proportional to the change in the leg's bend angle at the knee. By differentiating this signal one can obtain a signal proportional to the velocity y(t) depicted above, but without using an accelerometer. Since one need not integrate this signal to compute velocity or displacement, the energy expenditure is computed simply as a multiplication.

Still another system for power measurement is shown in FIG. 62. In FIG. 62, a force gage or compressive strain element 1700 is inserted into the inside of a tongue 1702 of a ski boot 1704. When the skier leans forward, the force on the tongue 1702 increases to first order in proportion to the angle of the lower leg with respect to the ski/board. Thus, one can measure a signal indicative of the quantity y(t) by measuring the force on the boot's tongue. Once again, since one need not integrate this signal to compute velocity or displacement, the energy expenditure is computed as a multiplication.

Other Techniques for Drop Distance

In one aspect, instantaneous height above the surface (a relative rather than an absolute measurement) is provided by the system of FIG. 59. By using a simple pulse output sound waveform, and applying a time gate to the acoustic return, the system can sense the distance of a skier/boarder above the ground from the round-trip time it takes the signal to return to the sensor. This provides a measure of the skier's instantaneous height.

Other Techniques for Airtime

Several alternative airtime sensors are next shown, including one new signal processor to detect transients to provide a "trigger" or "gate" for estimating airtime.

Figure 63:
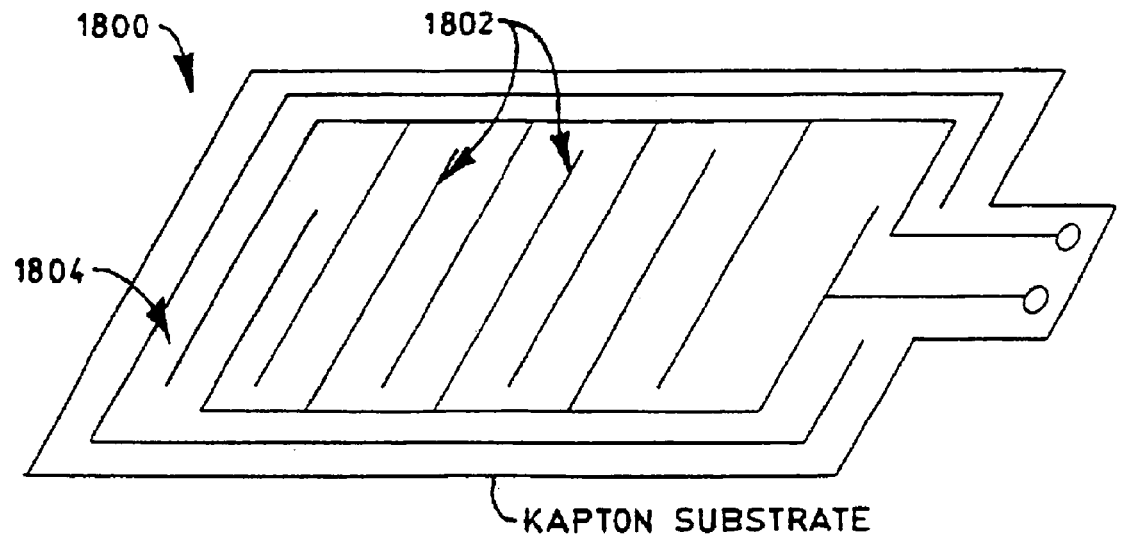
FIGS. 63-73 illustrate force sensing techniques and issues, in accord with the invention.
Figure 64:
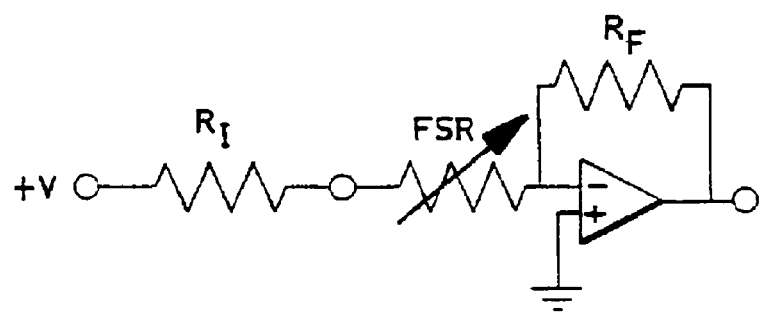

With a FSR (Force Sensing Resistor) one can detect the presence of a skier in the vehicle (for instance, in the bindings if positioned beneath the boot and above the binding), the skier's weight, and whether the skier is being supported by a surface or is "airborne". A typical FSR 1800 is sketched in FIG. 63. FSRs can be purchased from IEE Interlink for $2-$4 each in small quantities depending on the aperture size. These pads consist of interdigitated electrodes 1802 over a semi-conductive polymer ink 1804. The resistance between the electrodes 1802 decreases nonlinearly as a function of applied compressive load, and they exhibit high sensitivity. A PSA layer is generally applied to one side; a further encapsulant (say of polyurethane) is desirable for a harsh/wet environments. A typical FSR signal conditioning circuit is shown in FIG. 64 that provides a voltage indicative of the FSR's changing resistance. Unlike accelerometers or induced-strain sensors (such as the AMP PVDF sensors), FSRs sense static loads.

Figure 65:
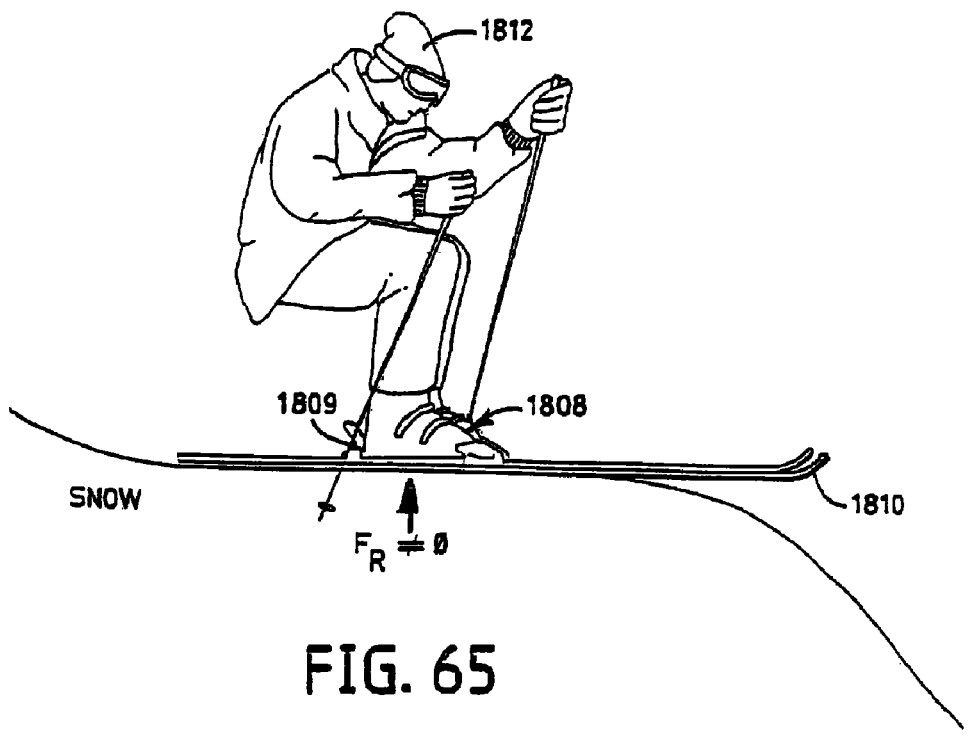
Figure 66:
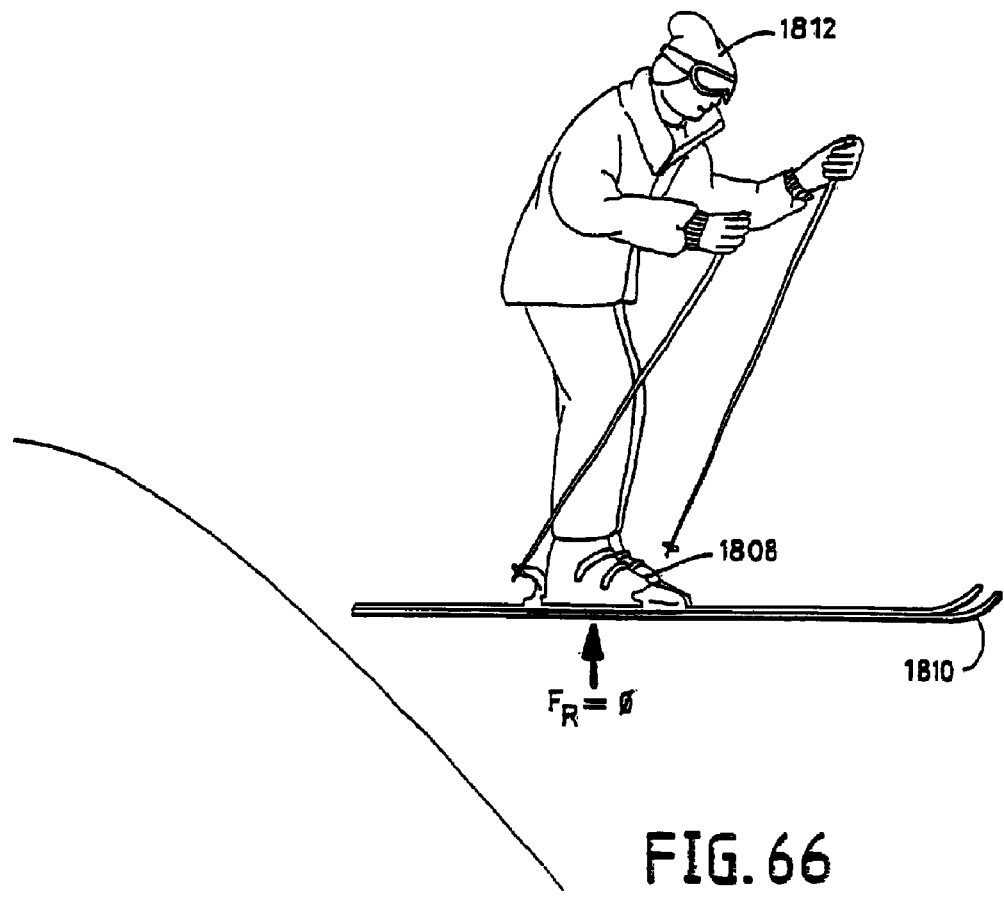
Figure 67:
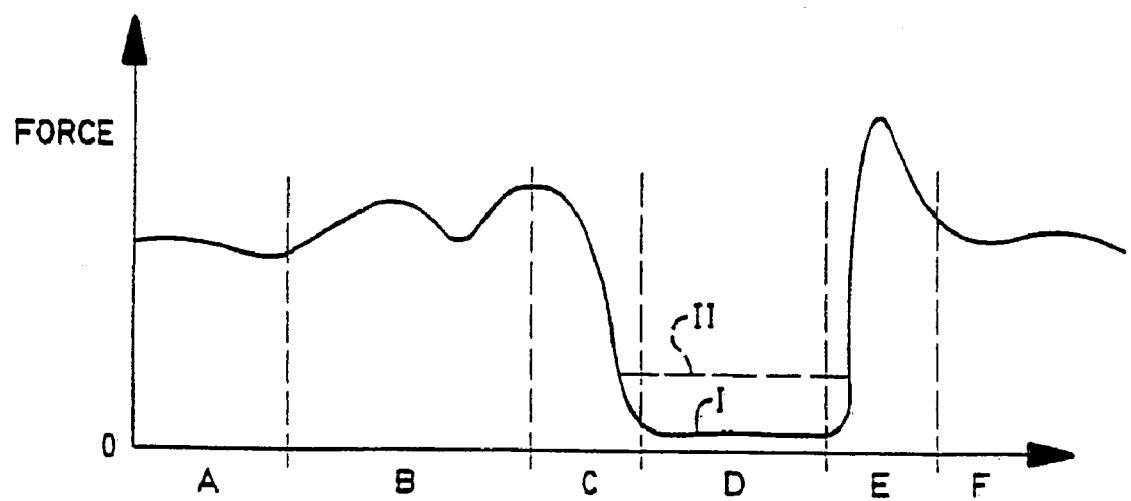

Consider FIGS. 65 and 66. An FSR described above is placed in the load path of the skier, either beneath the boot 1808, within the boot's heel 1809, within the ski/board, or beneath the ski/board 1810. Consequently, when the skier 1812 stands on the ski/board 1810, and when the ski/board 1810 is on the ground, there is a reaction force $F_R$ pushing up against the skier 1812. This will be sensed by the FSR, as shown in FIG. 67, region "A". When the skier 1812 is pushed by bumps and moguls this force will change, as shown in region "B", FIG. 67, owing to Newton's second law. When the skier/boarder 1812 leaves the ground, as shown in FIG. 66, then region "C" is realized and reaction force diminishes to zero as an easily-sensed transient. This too will be sensed by the FSR, as suggested in FIG. 67, region D of Trace I. Trace II of FIG. 67 is closer to zero force (if not actually equal zero) and corresponds to the case whereupon there is no residual compression of the FSR due to the clamping load of the binding, if the sensor is in the binding or boot heel (or due to residual mechanical stresses induced during manufacture if the sensor is embedded within the ski/board). Trace II, which shows a higher "residual" load, reflects when these residual stresses are present, and needs to be quantified if the transient amplitude change in region "C" is to be use as a trigger or gate to the airtime estimation. The skier/boarder 1812 becomes reacquainted with the supporting surface in region "E", as the reaction force may now actually peak owing to the compressional transient; this too is measured by the FSR in the load path. The skier/boarder 1812 returns to "normal" travel again in region "F".

The output of the FSR can in all likelihood be low-pass filtered at around 20 Hz, since the latency in estimating liftoff can be about 500 msec (i.e., a reasonable minimum airtime lower limit). Trigger generation is effected using only a comparator or similar analog thresholding electronics based upon signal amplitude, and perhaps slew rate or hysteresis (probably not necessary); and there is no need to measure spectral changes. Unfortunately, FSRs do not have significant bandwidth and thus can limit the measurable vehicle speed.

In the user of PVDFs (i.e., the piezo foils discussed above), certain care should be taken. First, they are only capable of measuring dynamic signals: they will not measure a static load, or a static displacement. For static measurements (such as inferring weight as described above) or very low frequency measurements (typically below 5 to 10 Hz), other sensors should be employed such as FSRs.

Figure 68:
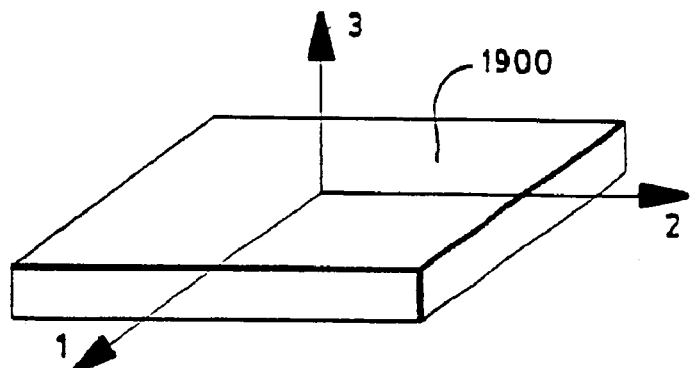

A second performance limitation of the PVDF is that these sensors are far more sensitive to induced in-plane strains than to compressional strains. These strain axes 1-3 are defined in FIG. 68, showing one piezo foil 1900. The in-plane strains are in the "1" and "2" directions, with the "1" direction being the "pull" direction for the PVDF (almost always the long axis for the AMP sensing strips) associated with the material's processing. The compressional strain is in the "3" direction. Note that the electromechanical constituitive constants relating an input strain to an output voltage measured across the thickness of the sensor (where the electrodes are always placed) are approximately an order of magnitude larger in the "1" direction than in the "3" direction; while the values in the "2" and "3" directions are approximately equal. This is an artifact of the fabrication methodology for so-called "uniaxial" PVDF. Consequently, this makes the AMP PVDF strips excellent dynamic strain gages.

Figure 69:
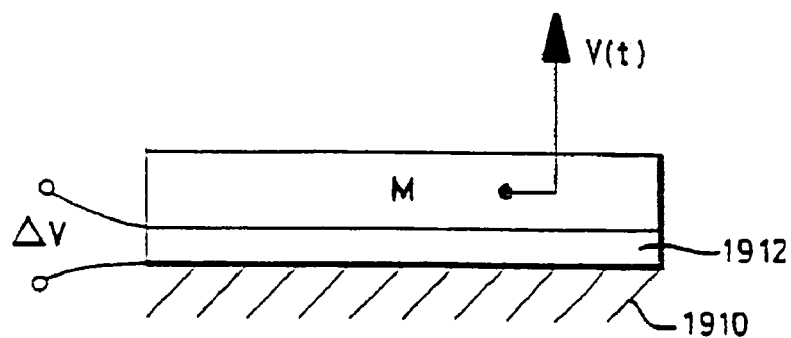

This enhanced strain performance is not a problem if the sensor strip is attached to a rigid, non-bending surface, as suggested above (e.g., the housing 32, FIG. 1A). In this configuration the piezo is rigidly glued to an inflexible surface 1910, FIG. 69, and a rigid mass M is attached to the top of the piezo 1912. Consequently, when the lower surface is vibrated, the mass M causes the piezo 1912 to compress owing to the inertial forces, leading to a voltage output ΔV across the sensor's thickness proportional to the vibration, which is essentially how an accelerometer works.

Figure 70:
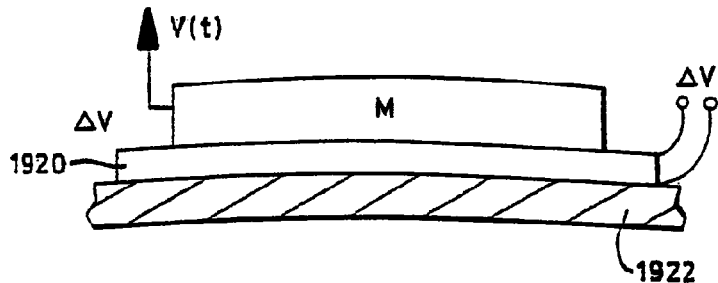

Consider a piezo strip 1920 attached to a flexible surface 1922, as suggested in FIG. 70. When the surface bends in response to an input vibration, this induces an output in the sensor ΔV proportional to the bending strain. The vibration need not accelerate the mass M in the vertical direction to induce this output; so, if the surface is a ski, and the ski flexes irrespective of whether or not the ski is accelerated vertically, you will measure an output that will typically swamp any signal due to vertical acceleration or vibration. In this situation, you are measuring the flexural response of the ski, and not the vertical vibration induced by the ski's passage over a rough surface. In order to measure this vertical vibration, one needs to deconvolve the ski's flexural dynamics, a significant challenge. Note also that the ski itself is acting as a filter, since it has natural modes of response much like a guitar string or drum head, and very much wants to respond at those frequencies. This will skew and perhaps dominate any measurement of the vibrational spectra.

Figure 71:
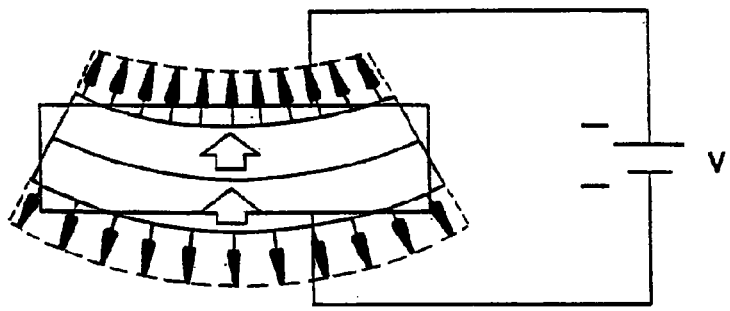
Figure 72:
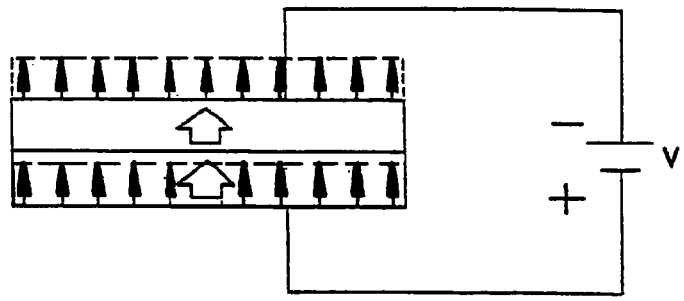

These problems are addressed in FIGS. 71 and 72. Consider a ski or snowboard having two PVDF sensors deposited on it, one atop the ski and one below (or any symmetric arrangement about the midline of the ski/board), registered spatially one above the other. These are laid up with their polarization axes aligned, as suggested by the arrows in FIGS. 71,72. In FIG. 71, the ski bends, and the top sensor sees a compressive strain, while the lower sees an extensive strain. Thus, charge will migrate to the outer surfaces of both piezos. If one measures the voltage potential across these two sensors the result will be (ideally) zero; the same is true for bending in the opposite direction, for higher-order modes, etc. In practice, the bending strain response is significantly diminished, with residual response due to mismatched sensors and positioning errors. One can think of this arrangement as providing "common mode rejection" for bending strains. In FIG. 72, if a compressive stress is applied as from a vertical acceleration of the ski owing to its passage over an irregular surface then a potential difference is induced over the outer layers of the sensor composite, and a voltage V is measured.

Figure 73:
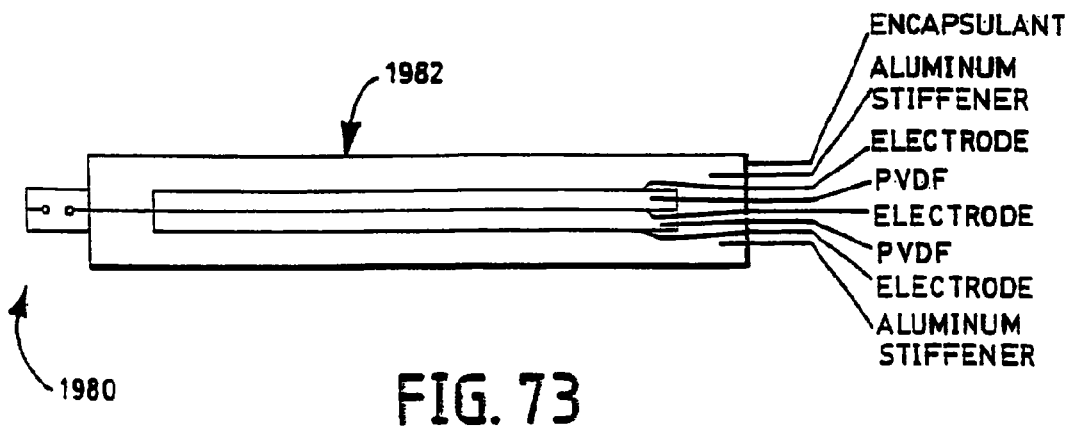

An alternate means of achieving an analogous result on one side of the vehicle is to build a sandwich of two PVDF layers, as shown in FIG. 73. Here, the polarization axes are aligned in opposition. Unlike the previous embodiment, this arrangement's voltage output is measured via the connections shown at the left side 1980 of the sensor 1982, which tap both the inner and outer electrodes of the piezo composite. This arrangement has proven to yield a superior acoustic receiver, and provides common mode rejection to electrical interference such as from radio transmitters.

For both embodiments of FIGS. 71/72 and 73, one can employ a voltage-follower circuit to drive long leads, if required.

Figure 74:
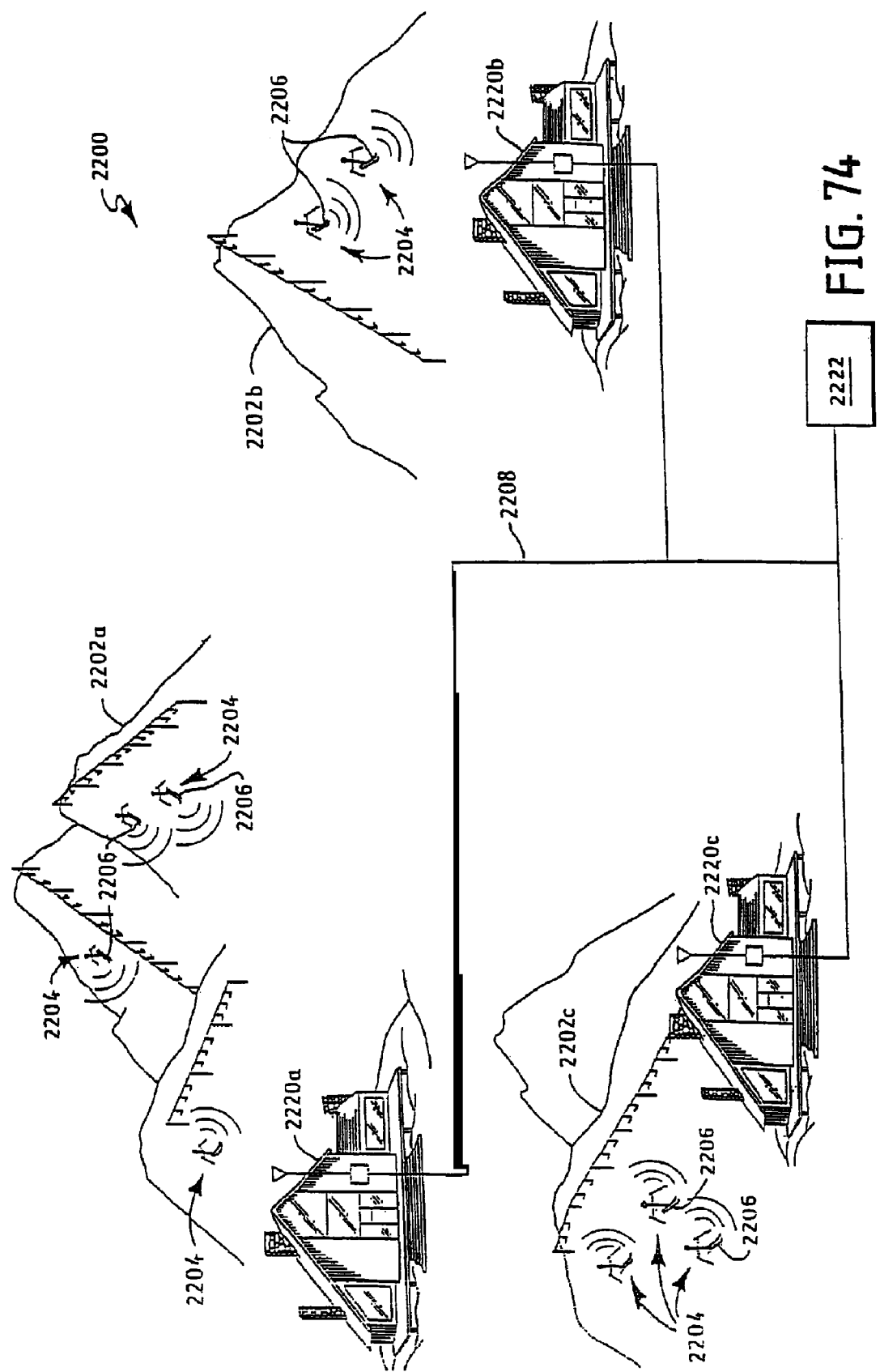
FIG. 74 shows a network game constructed according to the invention.
Figure 75:
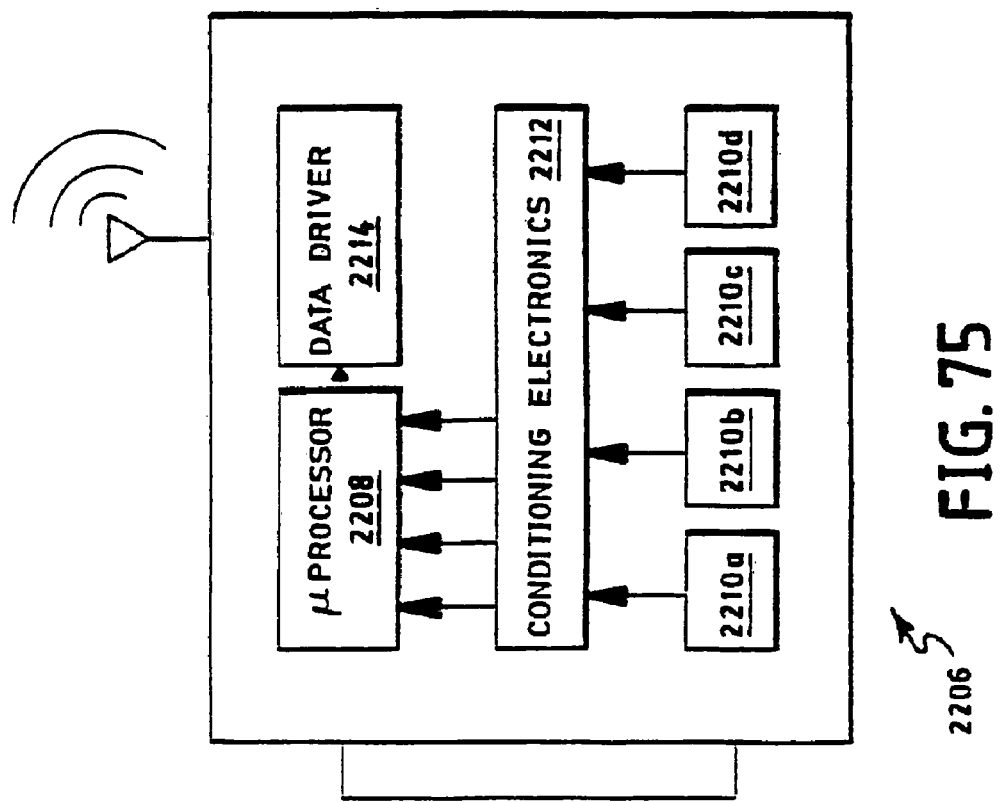
FIG. 75 describes further features of the game of FIG. 74.

FIG. 74 illustrates a gaming system 2200 which connects several mountains 2202a-2202c via a WAN or the Internet 2208. A plurality skier or snowboarder 2204 are on the mountains 2202; and each has a data transmitting device 2206 (the device is illustrated in FIG. 75); and each device 2206 includes functionality such as described herein to provide performance data. In particular, each device 2206 includes a microprocessor 2208 (or microcontroller or other intelligence sufficient to assist in acquiring data from connected transducers) and can include one or more of the following: airtime sensor 2210a, speed sensor 2210b, power sensor 2210c and drop distance sensor 2210d. If required, a battery drives the device 2206. The microprocessor 2208 collects data from one or more sensors 2210 (note that sensors 2210 can be simple transducers connected through conditioning electronics 2212), processes the data, and transmits the data to a data driver 2214, such as data section 22, FIG. 1A. The data driver 2214 communicates with receivers (e.g., the receiver 72, FIG. 1B) at each respective lodge 2220a-1220c so that the data is available on the Internet 2208. In this manner, data from any mountain is collected for comparison to other players on other mountains. A main database 2222 keeps and stores all data for access through the Internet 2208. For example, the database 2222 can include a WWW interface which all can access (if desired, or only if give access authority) to acquire and compare scores across the nation (or world).

Note that the game played by the system 2200 can be for airtime, speed, power, or drop distance, or a combination of one or more. Further, it should be understood that the medium of skiing is shown illustratively, and that other sports are easily accomplished in a similar system. By way of example, each person 2204 could be a mountain biker instead. Or, each mountain could be replaced by a lake or ocean and each person 2204 can be a windsurfer.

Figure 76:
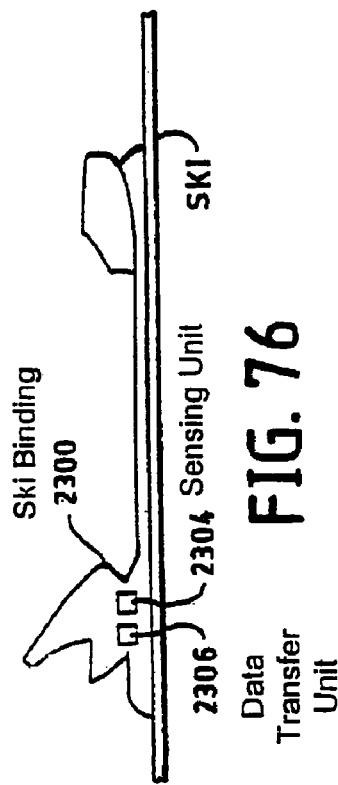
FIG. 76 shows a boot-binding sensor arrangement constructed according to the invention.
Figure 77:
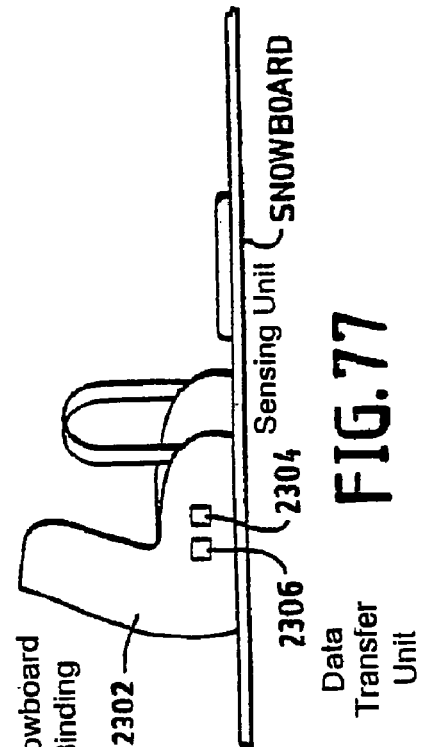
FIG. 77 shows a boot sensor arrangement constructed according to the invention.

Certain devices of the invention can also be incorporated into a boot binding, such as shown in FIGS. 76 and 77. In FIG. 76, a ski binding 2300 is shown; while in FIG. 77, a snowboarder binding 2302 is shown. In each case, a sensing unit 2304 such as described above is incorporated into the binding. The device 2304 can include, for example, an airtime device and/or a power sensor and/or a pitch-based speed sensor and/or an altimeter. A data transfer unit 2306 (e.g., a radio, inductive loop, IR transmitter) connects to the unit 2304 so that data (e.g., airtime, power, speed and drop distance) can be relayed to the user (or to a data unit or to the base station). For example, the user carries a sister data receive unit (not shown) that provides the user with the desired data. Note that data transfer unit can be an IR transmitting section and the receive data unit can be a datawatch, such as described above. The device 2304 includes power and other circuitry so as to operate and acquire the appropriate data, as described above.

The advantage of the design of FIG. 76 is that a sensing unit according to the invention is not mounted directly on the ski (or snowboard) and is further protected from the environment. Also, it is more practical to mounting to a board or ski. Without such packaging advantage, it is difficult, though not impossible, to package a sensing unit (such as an air meter or speed meter, described herein) onto a board with sufficiently small size and weight. Preferably, a device such as the device 1102 of FIG. 41 has only a depth of 0.300" or less, and an overall weight of less than ⅛ to ¼ pound. Such a size is preferred in order to fit the device into a recessed area on the board without excessive overhang or add-on weight. However, as in FIG. 77, this goal is relaxed somewhat.

Power can also be determined by other methods, in accord with the invention. For example, with an accelerometer pointed up, relative to the ski and perpendicular to the ground, when the user hits bumpy terrain, the accelerometer will have "peaks" and valleys. One technique for determining power is thus to count peaks past some predetermined threshold, such as shown in FIG. 78, which illustrates "5" peak signals which pass the threshold "k". The value "5" does not have to correspond to a real unit, such as g's. The value of k can be set experimentally such as through the data unit described above. k should be above 1 G, for example, which is a constant force. That is, when the accelerometer is not pointed along the gravity vector, it might read "0" and will read "1"—and neither event should effect the power calculation. Alternatively, an exact determination of g's can be made and provided by the sensor, and thus given to the user. However, this requires extensive processing and is not overly practical. The goal here is to display units that are common to all. For example, power units could extend from 0-10 (or 0-100) wherein, for example, a user with a 9 shows great exertion as compared to a user with a "1" reading (or alternatively, a 70 as compared to a 10 reading). It is thus important to make the power determination at appropriate intervals, or at a set integration time.

FIG. 79 shows a sensor 2499 such as described herein including a doppler module 2500. The beam 2502 from the module 2500 extends backwards, or forwards, on the ski (or snowboard) 2506 and about 45 degrees to the side. In this manner, the beam 2502 need not extend through the board, such as described above; but can instead broadly illuminate a region 2504 away from the ski 2506. Since the module 2500 is slightly above the board, it can illuminate the region 2504 without going through the board 2506. This greatly assists taking such measurements, for example, in the ultrasound region since ultrasound does not transmit through boards well. Similarly, for microwave, metal in the board can completely wipe out a signal return, effectively eliminating the speed measurement.

It should be noted that a power sensing unit can be made generically and simply on a wrist watch, as discussed above. Such a unit is useful for various sports, such as basketball, to monitor a user's aggressiveness in play. As shown in FIG. 80, such a unit in the form of a watch 2600 can provide data to a computer 2602 at the gaming site (FIG. 80 shows one user on a basketball court, for example; though the scene is equally applicable to other sports, e.g., soccer, football and hockey). The computer 2602 and watch 2600 have data transfer capability such as through RF signals, known to those in the art. During play, the user 2604 is effectively "monitored" so that the coach or owner can effectively gauge performance and aggressiveness. The device within the watch 2600 can include sensors such as described herein. The watch 2600 further includes batteries and required circuitry.

The unit 2600' could also be placed and/or sewn into a user's shorts, as shown in FIG. 81.

Certain sensing units of the invention require power. Often it is desirable to turn the power off when the unit is not in use, such as when the user is in a bar. In accord with the invention, a FET switch can be used for this purpose, such as known in the art. This saves battery life.

Power and/or speed can also be measured and assessed by measuring signal PSD.

Barometers and altimeters, in accord with the invention, preferably "logic" out data at the base and peak of a mountain, so that data is not stored and recorded in these regions. This is similar to logic out regions such as airtime above 30 seconds, which likely does not occur, or for less than 1 second (or 2 second) which resembles walking and which should be ignored.

Figure 82:
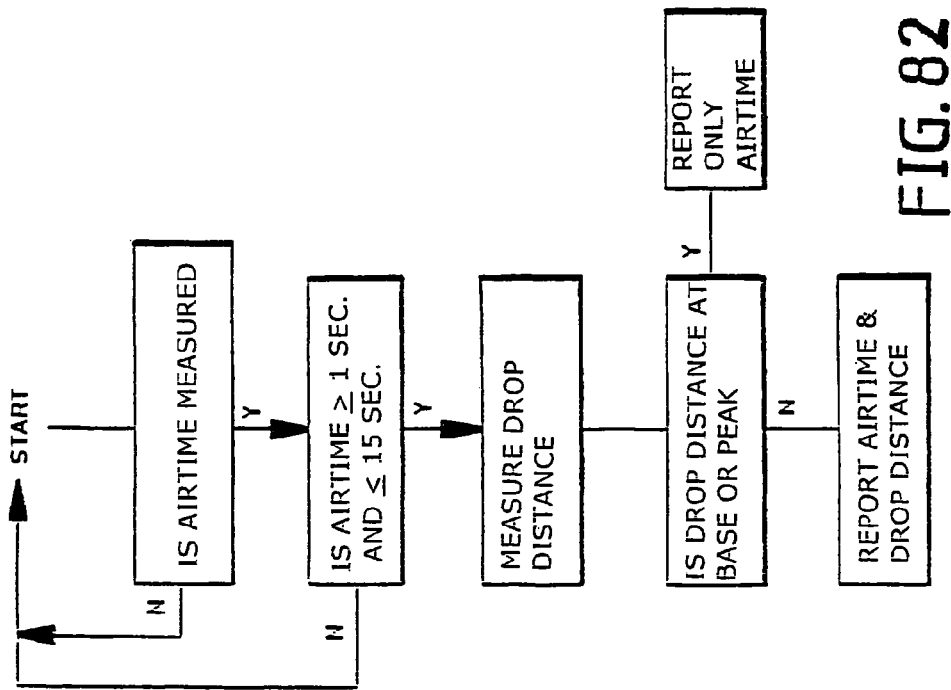
FIG. 82 shows a flow-chart illustrating drop distance logic in accord with the invention.

Note, if there is no airtime, often, the circuitry of the invention should operate to logic out drop distance too, such as shown in FIG. 82.

Figure 83:
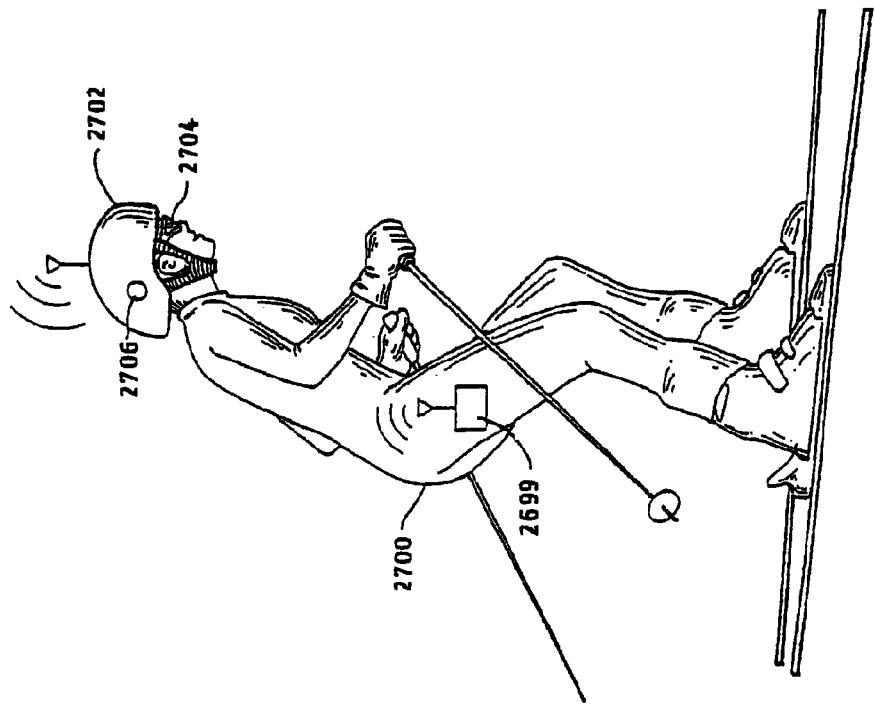
FIG. 83 shows a real-time performance system constructed according to the invention.

FIG. 83 illustrates one other embodiment wherein data from a sensor 2699 such as described herein (e.g., a sensor such as an airtime sensor) transmits data to a user 2700 at the user's helmet 2702. A heads-up display 2704 and/or a microphone 2706 can be used to relay performance data to the user 2700, for example by informing the user of "airtime". If the user is a speed skier, the data is useful to modify form since they do not wish airtime. A base station computer can also monitor the airtime data which can then be evaluated later. A buzz sent to the mic 2706 can similarly inform the user 1700. The heads-up display 2704 can take the form of sunglasses; and the helmet 2702 is not required.

Sensing units of the invention can be integrated within many sports implements, such as shown in FIGS. 84A-84H. Each implement of FIGS. 84A-84H includes a sensing unit 3000, described herein. The implements include, at least, ice skates, water skis 3004 (or wakeboards 3004), ski poles 3006, windsurfer 3008, surfboard 3010, tennis racquet 3012, skateboard 3014, roller blade 3016, and volleyball 3018. Other implements are within the scope of the invention.

Those skilled in the art should appreciate that changes can be made within the description above without departing from the scope of the invention.

The invention thus attains the objects set forth above, among those apparent from preceding description. Since certain changes may be made in the above apparatus and methods without departing from the scope of the invention, it is intended that all matter contained in the above description or shown in the accompanying drawing be interpreted as illustrative and not in a limiting sense.

It is also to be understood that the following claims are to cover all generic and specific features of the invention described herein, and all statements of the scope of the invention which, as a matter of language, might be said to fall there between.

What is claimed is:

1. A location measurement system, comprising:
a GPS receiver configured for attachment to a person and for determining earth location of the person;
at least one of a display and an audio feedback that is attachable to the person;
memory storing map data wherein the map data includes 3-D topographical information; and
a processor configured to
process the earth location and the map data to instruct display of a person's current location with a map on the display,
detect contact with ground based upon movement of the person over the ground,
determine vertical drop of the person based upon the movement of the person over the ground during at least one time interval in which lack of contact with the ground is detected followed by subsequent detection of contact with the ground; and
compare the vertical drop of the person to a vertical drop determined for another person;
wherein the comparison of the vertical drop of the person to the vertical drop determined for another person is configured for output to the at least one of the display and the audio feedback.

2. The system of claim 1, the GPS receiver, memory and processor being configured within a watch wherein the display is the display of the watch.

3. The system of claim 1, the GPS receiver further configured to determine speed of the person, the processor configured to instruct output of speed to the person on the at least one of the display and the audio feedback.

4. The system of claim 1, the GPS receiver configured to determine distance traveled of the person, the processor further configured to instruct output of distance traveled to the person on the at least one of the display and the audio feedback.

5. The system of claim 1, further comprising a vibrational sensor configured to determine the contact and the lack of contact with the ground.

6. A location determining system, comprising:
a housing configured for attachment to a person;
a GPS receiver configured with the housing for determining earth location;
memory configured with the housing and storing map data wherein the map data includes 3-D topographical information;
at least one of a display and an audio feedback configured for attachment to the person; and
a processor configured with the housing to process earth location and the map data to determine location of the person, to detect contact with ground based upon movement of the person over the ground, to determine a vertical drop of the person based upon movement of the person over ground during at least one time interval in which lack of contact with the ground is detected followed by subsequent detection of contact with the ground, and to instruct display of the person's location on a map, wherein the processor is further configured to compare the vertical drop of the person to a vertical drop of another person;
wherein the comparison of the vertical drop of the person to the vertical drop of the another person is output to the at least one of the display and the audio feedback.

7. The system of claim 6, wherein the location determining system comprises at least one display, and wherein the display is positioned proximate to or integral with the housing.

8. The system of claim 6, further comprising an altimeter for determining altitude of the housing.

9. The system of claim 8, wherein the location determining system comprises at least one display, and wherein the display includes a watch for displaying one or both of the person's location and the altitude.

10. The system of claim 6, the processor configured to determine speed associated with movement of the housing.

11. The system of claim 10, wherein the location determining system comprises at least one display and wherein the display includes a watch for displaying one or both of the person's location and the speed.

12. The system of claim 6, further comprising a wireless transmitter configured with the housing to transmit data indicative of location to a remote location.

13. A performance measurement system, comprising:
a first GPS receiver configured for attachment to a first person and for determining performance data for the first person, wherein the performance data of the first person comprises a vertical drop determined based upon movement of the first person over ground during at least one time interval in which lack of contact with the ground is detected followed by subsequent detection of contact with the ground;
a memory for storing performance data for a plurality of people, including at least the first person;
a processor coupled to the first GPS receiver, the processor configured to process the performance data for the first person and compare the performance data of the first person with performance data of at least one other person within the plurality of people; and
at least one of a display and an audio feedback for attachment to the first person;
wherein the comparison of the performance data of the first person with the performance data of the at least one other person is output to the at least one of the display and the audio feedback.

14. The performance measurement system recited in claim 13, wherein the performance data includes at least one of vertical drop, power, speed, drop distance, location, acceleration, and energy.

15. The performance measurement system recited in claim 13, wherein the memory is a server that is remote from the first GPS receiver.

16. The performance measurement system recited in claim 15, further comprising a second GPS receiver for attachment to a second person and for determining performance data for the second person, and a second at least one of a display and an audio feedback for attachment to the second person, and wherein the processor is further configured to process the performance data for the second person and compare the performance data of the second person with performance data of at least the first person; wherein the comparison of the performance data of the second person with performance data of at least the first person is output to the second at least one of the display and the audio feedback.

* * * * *